(12) United States Patent
Sakanaka et al.

(10) Patent No.: US 9,724,427 B2
(45) Date of Patent: Aug. 8, 2017

(54) ANTI-LY6E ANTIBODIES AND IMMUNOCONJUGATES AND METHODS OF USE

(71) Applicant: Genentech, Inc., South San Francisco, CA (US)

(72) Inventors: Chie Sakanaka, Tokyo (JP); Peter Chang, Greenbrae, CA (US)

(73) Assignee: Genentech, Inc., South San Francisco, CA (US)

( * ) Notice: Subject to any disclaimer, the term of this patent is extended or adjusted under 35 U.S.C. 154(b) by 161 days.

(21) Appl. No.: 14/119,835

(22) PCT Filed: May 20, 2013

(86) PCT No.: PCT/US2013/041848
§ 371 (c)(1),
(2) Date: Nov. 22, 2013

(87) PCT Pub. No.: WO2013/177055
PCT Pub. Date: Nov. 28, 2013

(65) Prior Publication Data
US 2016/0199508 A1 Jul. 14, 2016

Related U.S. Application Data

(60) Provisional application No. 61/649,775, filed on May 21, 2012.

(51) Int. Cl.
| | | |
|---|---|---|
| C07K 16/28 | (2006.01) | |
| A61K 47/48 | (2006.01) | |
| A61K 49/04 | (2006.01) | |
| C07K 16/30 | (2006.01) | |
| A61K 39/00 | (2006.01) | |

(52) U.S. Cl.
CPC .. *A61K 47/48561* (2013.01); *A61K 47/48384* (2013.01); *A61K 49/04* (2013.01); *C07K 16/28* (2013.01); *C07K 16/30* (2013.01); *C07K 16/303* (2013.01); *C07K 16/3015* (2013.01); *C07K 16/3023* (2013.01); *C07K 16/3069* (2013.01); *A61K 2039/505* (2013.01); *C07K 2317/24* (2013.01); *C07K 2317/33* (2013.01); *C07K 2317/76* (2013.01); *C07K 2317/92* (2013.01)

(58) Field of Classification Search
CPC ........ A61K 47/48384; A61K 47/48561; C07K 16/28; C07K 2317/24
USPC .......................... 424/181.1; 530/387.9, 391.9
See application file for complete search history.

(56) References Cited

U.S. PATENT DOCUMENTS

| | | | |
|---|---|---|---|
| 5,773,223 A | 6/1998 | Shyamala et al. | |
| 6,214,345 B1 | 4/2001 | Firestone et al. | |
| 7,303,749 B1 | 12/2007 | Chari et al. | |
| 7,387,772 B1 | 6/2008 | Hansen et al. | |
| 7,498,298 B2 | 3/2009 | Doronina et al. | |
| 7,521,541 B2 | 4/2009 | Eigenbrot et al. | |
| 7,601,354 B2 | 10/2009 | Chari et al. | |
| 7,659,241 B2 | 2/2010 | Senter et al. | |
| 7,745,394 B2 | 6/2010 | Doronina et al. | |
| 7,829,531 B2 | 11/2010 | Senter et al. | |
| 7,851,437 B2 | 12/2010 | Senter et al. | |
| 7,855,275 B2 | 12/2010 | Eigenbrot et al. | |
| 7,964,566 B2 | 6/2011 | Doronina et al. | |
| 7,964,567 B2 | 6/2011 | Doronina et al. | |
| 7,994,135 B2 | 8/2011 | Doronina et al. | |
| 8,088,387 B2 | 1/2012 | Steeves et al. | |
| 8,142,784 B2 | 3/2012 | Ebens et al. | |
| 8,198,417 B2 | 6/2012 | Steeves et al. | |
| 8,309,300 B2 | 11/2012 | Junutula et al. | |
| 8,557,780 B2 | 10/2013 | Doronina et al. | |
| 9,290,578 B2 * | 3/2016 | Asundi ............ | A61K 47/48384 |
| 2003/0092125 A1 | 5/2003 | Davis et al. | |
| 2006/0094676 A1 | 5/2006 | Lahav | |
| 2007/0269442 A1 | 11/2007 | Webber | |
| 2008/0075712 A1 | 3/2008 | Hattori | |
| 2011/0256157 A1 | 10/2011 | Howard et al. | |
| 2012/0148610 A1 | 6/2012 | Doronina et al. | |

FOREIGN PATENT DOCUMENTS

| | | |
|---|---|---|
| JP | 2005-503768 A | 2/2005 |
| JP | 2006-510735 A | 3/2006 |
| JP | 2006-515751 A | 6/2006 |
| JP | 2009-530645 A | 8/2009 |
| JP | 2011-528360 A | 11/2011 |
| KR | 10-2011-0040922 | 4/2011 |
| WO | 99/55842 | 11/1999 |
| WO | 02/082041 A2 | 10/2002 |
| WO | 2004016225 | 2/2004 |
| WO | 2004/045516 A2 | 6/2004 |
| WO | WO 2004/003019 * | 6/2004 |
| WO | 2005/068503 | 7/2005 |
| WO | 2005/081711 A2 | 9/2005 |
| WO | 2005/082023 | 9/2005 |
| WO | 2005/117986 A2 | 12/2005 |
| WO | 2006/034488 A2 | 3/2006 |

(Continued)

OTHER PUBLICATIONS

Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*

(Continued)

*Primary Examiner* — Lynn Bristol
(74) *Attorney, Agent, or Firm* — McNeill Baur PLLC

(57) ABSTRACT

The invention provides anti-Ly6E antibodies, immunoconjugates and methods of using the same.

40 Claims, 15 Drawing Sheets

(56) References Cited

FOREIGN PATENT DOCUMENTS

| WO | 2006/034488 A3 | 3/2006 |
|---|---|---|
| WO | 2006/060533 | 6/2006 |
| WO | 2007/064345 | 6/2007 |
| WO | 2007/100385 | 9/2007 |
| WO | 2007/109347 A2 | 9/2007 |
| WO | 2010/009124 | 1/2010 |
| WO | 2010/099273 | 9/2010 |
| WO | 2011/056983 | 5/2011 |
| WO | 2011/106297 | 9/2011 |
| WO | 2011/130598 A1 | 10/2011 |
| WO | 2011/156328 | 12/2011 |
| WO | 2012/074757 | 6/2012 |

OTHER PUBLICATIONS

Asundi et al., "An Antibody-Drug Conjugate Directed against Lymphocyte Antigen 6 Complex, Locus E (LY6E) Provides Robust Tumor Killing in a Wide Range of Solid Tumor Malignancies" Clinical Cancer Research 21(14):3252-3262 (Jul. 15, 2015).

Doronina et al., "Development of Potent Monoclonal Antibody Auristatin Conjugates for Cancer Therapy" Nature Biotechnology 21(7):778-784 (Jul. 2003).

Fleming et al., "Multiple Glycosylphosphatidylinositol-Anchored Ly-6 Molecules and Transmembrane Ly-6E Mediate Inhibition of IL-2 Production" Journal of Immunology 153:1955-1962 (1994).

LeClair et al., "Isolation of a murine Ly-6 cDNA reveals a new multigene family" EMBO J. 5(12):3227-3234 (1986).

* cited by examiner

FIG. 1

Light Chain, Kappa:

FIG. 4

Heavy Chain:

FIG. 5

Heavy Chain:

|  | Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
|  |  |  |  |  |  |  |  |  |  |  |  |  |  |  |  |  |  |  |  |  |  |  |  |  |  |  |  |  |  |  | CDR H1 | | | | | | | | | | | | | |
| SEQ ID NO:47 | VH3 consensus | E | V | Q | L | V | E | S | G | G | G | L | V | Q | P | G | G | S | L | R | L | S | C | A | A | S | G | F | T | F | S | S | Y | A | M | S | W | V | R | Q | A | P | G | K | G |
| SEQ ID NO:44 | xLy6E mu9B12 | Q | V | Q | L | K | E | S | G | P | G | L | V | A | P | S | Q | S | L | S | I | T | C | T | V | S | G | F | S | L | T | G | Y | S | V | N | W | V | R | Q | P | P | G | K | G |
| SEQ ID NO:43 | hu9B12 VH3 graft | E | V | Q | L | V | E | S | G | G | G | L | V | Q | P | G | G | S | L | R | L | S | C | A | A | S | G | F | S | L | T | G | Y | S | V | N | W | V | R | Q | A | P | G | K | G |

|  | Kabat number | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 82A | 82B | 82C | 83 | 84 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
|  |  |  |  |  |  |  | CDR H2 | | | | | | | | | | | | | | | | | | | | | | | | | | | | | | | | | | | | | |
| SEQ ID NO:47 | VH3 consensus | L | E | W | V | G | A | I | S | . | . | S | G | G | S | T | Y | Y | A | D | S | V | K | G | R | F | T | I | S | R | D | N | S | K | N | T | L | Y | L | Q | M | N | S | L |
| SEQ ID NO:44 | xLy6E mu9B12 | L | E | W | M | G | L | I | W | . | . | G | D | G | S | T | D | Y | N | S | A | L | K | S | R | L | S | I | S | R | D | N | S | K | S | Q | V | F | L | K | M | N | S | L |
| SEQ ID NO:43 | hu9B12 VH3 graft | L | E | W | V | G | M | I | W | . | . | G | D | G | S | T | D | Y | N | S | A | L | K | S | R | F | T | I | S | R | D | N | S | K | N | T | L | Y | L | Q | M | N | S | L |

|  | Kabat number | 85 | 86 | 87 | 88 | 89 | 90 | 91 | 92 | 93 | 94 | 95 | 96 | 97 | 98 | 99 | 100 | 100A | 100B | 100C | D | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|---|---|---|---|---|---|---|
|  |  |  |  |  |  |  |  |  |  |  |  | CDR H3 | | | | | | | | | | | | | | | | | | | | | | |
| SEQ ID NO:47 | VH3 consensus | R | A | E | D | T | A | V | Y | Y | C | A | R | . | . | . | . | . | . | . | . | . | . | W | G | Q | G | T | L | V | T | V | S | S |
| SEQ ID NO:44 | xLy6E mu9B12 | R | S | E | D | T | A | V | Y | Y | C | A | R | D | Y | Y | F | N | Y | A | S | W | F | P | Y | W | G | Q | G | T | T | V | T | V | S | S |
| SEQ ID NO:43 | hu9B12 VH3 graft | R | A | E | D | T | A | V | Y | Y | C | A | R | D | Y | Y | F | N | Y | A | S | W | F | A | Y | W | G | Q | G | T | T | V | T | V | S | S |

*FIG. 6*

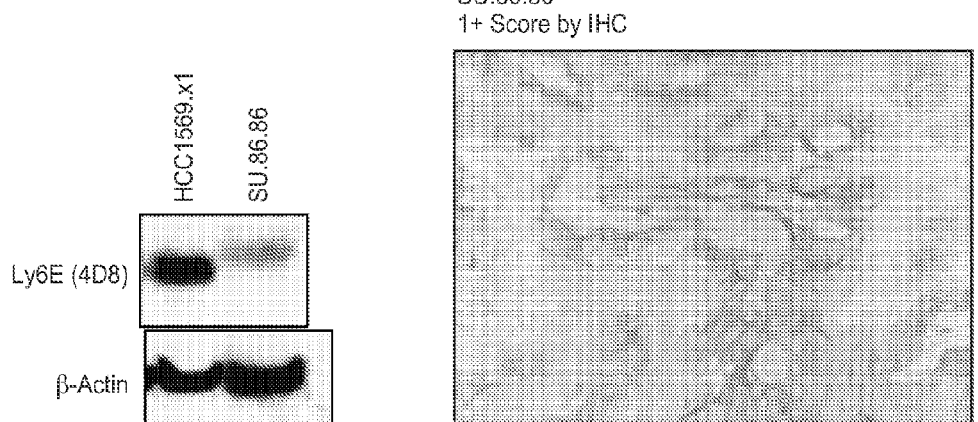
FIG. 8B  FIG. 8D
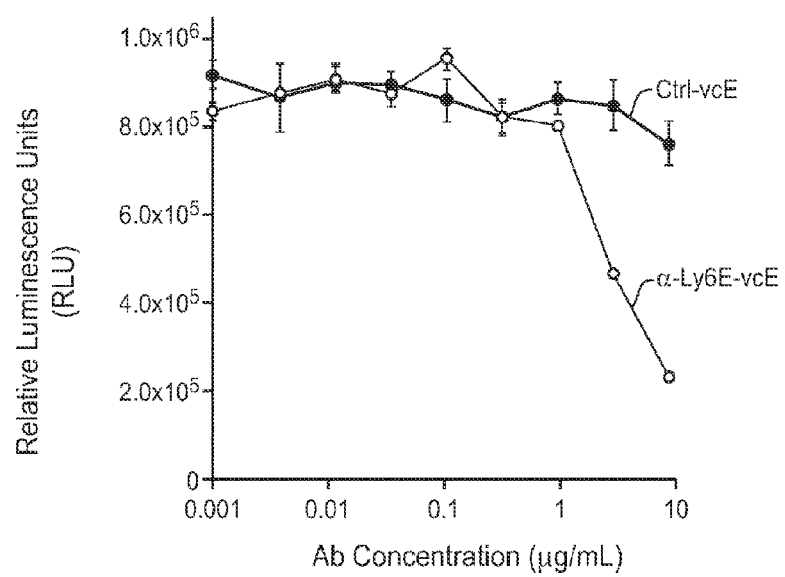
FIG. 8C

SEQUENCE LISTING

<160> NUMBER OF SEQ ID NOS: 56

<210> SEQ ID NO 1
<211> LENGTH: 131
<212> TYPE: PRT
<213> ORGANISM: Homo sapiens

<400> SEQUENCE: 1

Met Lys Ile Phe Leu Pro Val Leu Leu Ala Ala Leu Leu Gly Val
 1               5                  10                  15

Glu Arg Ala Ser Ser Leu Met Cys Phe Ser Cys Leu Asn Gln Lys
                20                  25                  30

Ser Asn Leu Tyr Cys Leu Lys Pro Thr Ile Cys Ser Asp Gln Asp
                35                  40                  45

Asn Tyr Cys Val Thr Val Ser Ala Ser Ala Gly Ile Gly Asn Leu
                50                  55                  60

Val Thr Phe Gly His Ser Leu Ser Lys Thr Cys Ser Pro Ala Cys
                65                  70                  75

Pro Ile Pro Glu Gly Val Asn Val Gly Val Ala Ser Met Gly Ile
                80                  85                  90

Ser Cys Cys Gln Ser Phe Leu Cys Asn Phe Ser Ala Ala Asp Gly
                95                  100                 105

Gly Leu Arg Ala Ser Val Thr Leu Leu Gly Ala Gly Leu Leu Leu
                110                 115                 120

Ser Leu Leu Pro Ala Leu Leu Arg Phe Gly Pro
                125                 130

<210> SEQ ID NO 2
<211> LENGTH: 131
<212> TYPE: PRT
<213> ORGANISM: Macaca fascicularis

<400> SEQUENCE: 2

Met Lys Ile Phe Leu Pro Val Leu Leu Ala Ala Leu Leu Gly Val
 1               5                  10                  15

Glu Arg Ala Ser Ser Leu Met Cys Phe Ser Cys Leu Asn Gln Lys
                20                  25                  30

Ser Asn Leu Tyr Cys Leu Lys Pro Thr Ile Cys Ser Asp Gln Asp
                35                  40                  45

Asn Tyr Cys Val Thr Val Ser Thr Ser Ala Gly Ile Gly Asn Leu
                50                  55                  60

Val Thr Phe Gly His Ser Leu Ser Lys Thr Cys Ser Pro Ala Cys
                65                  70                  75

Pro Leu Pro Glu Gly Ile Asn Val Gly Val Ala Ser Met Gly Ile
                80                  85                  90

Ser Cys Cys Gln Ser Phe Leu Cys Asn Phe Ser Ala Ala Asp Gly
                95                  100                 105

Gly Leu Arg Ala Ser Ala Thr Leu Leu Gly Ala Gly Leu Leu Leu
                110                 115                 120

Ser Leu Leu Pro Ala Leu Leu Arg Phe Gly Pro
                125                 130

<210> SEQ ID NO 3
<211> LENGTH: 107
<212> TYPE: PRT
<213> ORGANISM: Artificial sequence
<220> FEATURE:
<223> OTHER INFORMATION: Humanized

<400> SEQUENCE: 3

```
Asp Ile Gln Met Thr Gln Ser Pro Ser Ser Leu Ser Ala Ser Val
 1               5                  10                  15

Gly Asp Arg Val Thr Ile Thr Cys Ser Ala Ser Gln Gly Ile Ser
                20                  25                  30

Asn Tyr Leu Asn Trp Tyr Gln Gln Lys Pro Gly Lys Thr Val Lys
                35                  40                  45

Leu Leu Ile Tyr Tyr Thr Ser Asn Leu His Ser Gly Val Pro Ser
                50                  55                  60

Arg Phe Ser Gly Ser Gly Ser Gly Thr Asp Tyr Thr Leu Thr Ile
 65                  70                  75

Ser Ser Leu Gln Pro Glu Asp Phe Ala Thr Tyr Tyr Cys Gln Gln
                80                  85                  90

Tyr Ser Glu Leu Pro Trp Thr Phe Gly Gln Gly Thr Lys Val Glu
                95                  100                 105

Ile Lys
```

<210> SEQ ID NO 4
<211> LENGTH: 107
<212> TYPE: PRT
<213> ORGANISM: Artificial sequence
<220> FEATURE:
<223> OTHER INFORMATION: Chimeric

<400> SEQUENCE: 4

```
Asp Ile Gln Met Thr Gln Thr Thr Ser Ser Leu Ser Ala Ser Leu
 1               5                  10                  15

Gly Asp Arg Val Thr Ile Ser Cys Ser Ala Ser Gln Gly Ile Ser
                20                  25                  30

Asn Tyr Leu Asn Trp Tyr Gln Gln Lys Pro Asp Gly Thr Val Lys
                35                  40                  45

Leu Leu Ile Tyr Tyr Thr Ser Asn Leu His Ser Gly Val Pro Ser
                50                  55                  60

Arg Phe Ser Gly Ser Gly Ser Gly Thr Asp Tyr Ser Leu Thr Ile
 65                  70                  75

Ser Asn Leu Glu Pro Glu Asp Ile Ala Thr Tyr Tyr Cys Gln Gln
                80                  85                  90

Tyr Ser Glu Leu Pro Trp Thr Phe Gly Gly Gly Thr Lys Val Glu
                95                  100                 105

Ile Lys
```

<210> SEQ ID NO 5
<211> LENGTH: 120
<212> TYPE: PRT
<213> ORGANISM: Artificial sequence
<220> FEATURE:
<223> OTHER INFORMATION: Humanized

<400> SEQUENCE: 5

```
Glu Val Gln Leu Val Glu Ser Gly Pro Ala Leu Val Lys Pro Thr
 1               5                  10                  15

Gln Thr Leu Thr Leu Thr Cys Thr Val Ser Gly Phe Ser Leu Thr
                20                  25                  30

Gly Tyr Ser Val Asn Trp Ile Arg Gln Pro Pro Gly Lys Ala Leu
                35                  40                  45

Glu Trp Leu Gly Met Ile Trp Gly Asp Gly Ser Thr Asp Tyr Asn
```

```
                     50                  55                  60

Ser Ala Leu Lys Ser Arg Leu Thr Ile Ser Lys Asp Thr Ser Lys
                 65                  70                  75

Asn Gln Val Val Leu Thr Met Thr Asn Met Asp Pro Val Asp Thr
                 80                  85                  90

Ala Thr Tyr Tyr Cys Ala Arg Asp Tyr Tyr Phe Asn Tyr Ala Ser
                 95                 100                 105

Trp Phe Ala Tyr Trp Gly Gln Gly Thr Leu Val Thr Val Ser Ser
                110                 115                 120

<210> SEQ ID NO 6
<211> LENGTH: 120
<212> TYPE: PRT
<213> ORGANISM: Artificial sequence
<220> FEATURE:
<223> OTHER INFORMATION: Chimeric

<400> SEQUENCE: 6

Gln Val Gln Leu Lys Glu Ser Gly Pro Gly Leu Val Ala Pro Ser
  1               5                  10                  15

Gln Ser Leu Ser Leu Thr Cys Thr Val Ser Gly Phe Ser Leu Thr
                 20                  25                  30

Gly Tyr Ser Val Asn Trp Val Arg Gln Pro Pro Gly Lys Gly Leu
                 35                  40                  45

Glu Trp Leu Gly Met Ile Trp Gly Asp Gly Ser Thr Asp Tyr Asn
                 50                  55                  60

Ser Ala Leu Lys Ser Arg Leu Thr Ile Ser Lys Asp Asn Ser Lys
                 65                  70                  75

Ser Gln Val Phe Leu Lys Met Asn Ser Leu Gln Thr Asp Asp Thr
                 80                  85                  90

Ala Arg Tyr Tyr Cys Ala Arg Asp Tyr Tyr Phe Asn Tyr Ala Ser
                 95                 100                 105

Trp Phe Ala Tyr Trp Gly Pro Gly Thr Leu Val Thr Val Ser Ala
                110                 115                 120

<210> SEQ ID NO 7
<211> LENGTH: 11
<212> TYPE: PRT
<213> ORGANISM: Artificial sequence
<220> FEATURE:
<223> OTHER INFORMATION: Humanized

<400> SEQUENCE: 7

Ser Ala Ser Gln Gly Ile Ser Asn Tyr Leu Asn
  1               5                  10

<210> SEQ ID NO 8
<211> LENGTH: 7
<212> TYPE: PRT
<213> ORGANISM: Artificial sequence
<220> FEATURE:
<223> OTHER INFORMATION: Humanized

<400> SEQUENCE: 8

Tyr Thr Ser Asn Leu His Ser
              5

<210> SEQ ID NO 9
<211> LENGTH: 9
<212> TYPE: PRT
<213> ORGANISM: Artificial sequence
```

```
<220> FEATURE:
<223> OTHER INFORMATION: Humanized

<400> SEQUENCE: 9

Gln Gln Tyr Ser Glu Leu Pro Trp Thr
                  5

<210> SEQ ID NO 10
<211> LENGTH: 10
<212> TYPE: PRT
<213> ORGANISM: Artificial sequence
<220> FEATURE:
<223> OTHER INFORMATION: Humanized

<400> SEQUENCE: 10

Gly Phe Ser Leu Thr Gly Tyr Ser Val Asn
                  5                  10

<210> SEQ ID NO 11
<211> LENGTH: 16
<212> TYPE: PRT
<213> ORGANISM: Artificial sequence
<220> FEATURE:
<223> OTHER INFORMATION: Humanized

<400> SEQUENCE: 11

Met Ile Trp Gly Asp Gly Ser Thr Asp Tyr Asn Ser Ala Leu Lys
  1                5                 10                 15
Ser

<210> SEQ ID NO 12
<211> LENGTH: 12
<212> TYPE: PRT
<213> ORGANISM: Artificial sequence
<220> FEATURE:
<223> OTHER INFORMATION: Humanized

<400> SEQUENCE: 12

Asp Tyr Tyr Phe Asn Tyr Ala Ser Trp Phe Ala Tyr
                  5                  10

<210> SEQ ID NO 13
<211> LENGTH: 11
<212> TYPE: PRT
<213> ORGANISM: Artificial sequence
<220> FEATURE:
<223> OTHER INFORMATION: Chimeric

<400> SEQUENCE: 13

Ser Ala Ser Gln Gly Ile Ser Asn Tyr Leu Asn
                  5                  10

<210> SEQ ID NO 14
<211> LENGTH: 7
<212> TYPE: PRT
<213> ORGANISM: Artificial sequence
<220> FEATURE:
<223> OTHER INFORMATION: Chimeric

<400> SEQUENCE: 14

Tyr Thr Ser Asn Leu His Ser
                  5

<210> SEQ ID NO 15
<211> LENGTH: 9
<212> TYPE: PRT
```

```
<213> ORGANISM: Artificial sequence
<220> FEATURE:
<223> OTHER INFORMATION: Chimeric

<400> SEQUENCE: 15

Gln Gln Tyr Ser Glu Leu Pro Trp Thr
                5

<210> SEQ ID NO 16
<211> LENGTH: 10
<212> TYPE: PRT
<213> ORGANISM: Artificial sequence
<220> FEATURE:
<223> OTHER INFORMATION: Chimeric

<400> SEQUENCE: 16

Gly Phe Ser Leu Thr Gly Tyr Ser Val Asn
                5                   10

<210> SEQ ID NO 17
<211> LENGTH: 16
<212> TYPE: PRT
<213> ORGANISM: Artificial sequence
<220> FEATURE:
<223> OTHER INFORMATION: Chimeric

<400> SEQUENCE: 17

Met Ile Trp Gly Asp Gly Ser Thr Asp Tyr Asn Ser Ala Leu Lys
 1               5                  10                  15

Ser

<210> SEQ ID NO 18
<211> LENGTH: 12
<212> TYPE: PRT
<213> ORGANISM: Artificial sequence
<220> FEATURE:
<223> OTHER INFORMATION: Chimeric

<400> SEQUENCE: 18

Asp Tyr Tyr Phe Asn Tyr Ala Ser Trp Phe Ala Tyr
                5                   10

<210> SEQ ID NO 19
<211> LENGTH: 23
<212> TYPE: PRT
<213> ORGANISM: Artificial sequence
<220> FEATURE:
<223> OTHER INFORMATION: Humanized

<400> SEQUENCE: 19

Asp Ile Gln Met Thr Gln Ser Pro Ser Ser Leu Ser Ala Ser Val
 1               5                  10                  15

Gly Asp Arg Val Thr Ile Thr Cys
                20

<210> SEQ ID NO 20
<211> LENGTH: 15
<212> TYPE: PRT
<213> ORGANISM: Artificial sequence
<220> FEATURE:
<223> OTHER INFORMATION: Humanized

<400> SEQUENCE: 20

Trp Tyr Gln Gln Lys Pro Gly Lys Thr Val Lys Leu Leu Ile Tyr
 1               5                  10                  15
```

<210> SEQ ID NO 21
<211> LENGTH: 32
<212> TYPE: PRT
<213> ORGANISM: Artificial sequence
<220> FEATURE:
<223> OTHER INFORMATION: Humanized.

<400> SEQUENCE: 21

Gly Val Pro Ser Arg Phe Ser Gly Ser Gly Ser Gly Thr Asp Tyr
1               5                   10                  15

Thr Leu Thr Ile Ser Ser Leu Gln Pro Glu Asp Phe Ala Thr Tyr
                20                  25                  30

Tyr Cys

<210> SEQ ID NO 22
<211> LENGTH: 10
<212> TYPE: PRT
<213> ORGANISM: Artificial sequence
<220> FEATURE:
<223> OTHER INFORMATION: Humanized

<400> SEQUENCE: 22

Phe Gly Gln Gly Thr Lys Val Glu Ile Lys
1               5                   10

<210> SEQ ID NO 23
<211> LENGTH: 25
<212> TYPE: PRT
<213> ORGANISM: Artificial sequence
<220> FEATURE:
<223> OTHER INFORMATION: Humanized.

<400> SEQUENCE: 23

Glu Val Gln Leu Val Glu Ser Gly Pro Ala Leu Val Lys Pro Thr
1               5                   10                  15

Gln Thr Leu Thr Leu Thr Cys Thr Val Ser
                20                  25

<210> SEQ ID NO 24
<211> LENGTH: 14
<212> TYPE: PRT
<213> ORGANISM: Artificial sequence
<220> FEATURE:
<223> OTHER INFORMATION: Humanized.

<400> SEQUENCE: 24

Trp Ile Arg Gln Pro Pro Gly Lys Ala Leu Glu Trp Leu Gly
1               5                   10

<210> SEQ ID NO 25
<211> LENGTH: 32
<212> TYPE: PRT
<213> ORGANISM: Artificial sequence
<220> FEATURE:
<223> OTHER INFORMATION: Humanized

<400> SEQUENCE: 25

Arg Leu Thr Ile Ser Lys Asp Thr Ser Lys Asn Gln Val Val Leu
1               5                   10                  15

Thr Met Thr Asn Met Asp Pro Val Asp Thr Ala Thr Tyr Tyr Cys
                20                  25                  30

Ala Arg

```
<210> SEQ ID NO 26
<211> LENGTH: 11
<212> TYPE: PRT
<213> ORGANISM: Artificial sequence
<220> FEATURE:
<223> OTHER INFORMATION: Humanized

<400> SEQUENCE: 26

Trp Gly Gln Gly Thr Leu Val Thr Val Ser Ser
 1               5                  10

<210> SEQ ID NO 27
<211> LENGTH: 23
<212> TYPE: PRT
<213> ORGANISM: Artificial sequence
<220> FEATURE:
<223> OTHER INFORMATION: Chimeric

<400> SEQUENCE: 27

Asp Ile Gln Met Thr Gln Thr Thr Ser Ser Leu Ser Ala Ser Leu
 1               5                  10                  15

Gly Asp Arg Val Thr Ile Ser Cys
                 20

<210> SEQ ID NO 28
<211> LENGTH: 15
<212> TYPE: PRT
<213> ORGANISM: Artificial sequence
<220> FEATURE:
<223> OTHER INFORMATION: Chimeric

<400> SEQUENCE: 28

Trp Tyr Gln Gln Lys Pro Asp Gly Thr Val Lys Leu Leu Ile Tyr
 1               5                  10                  15

<210> SEQ ID NO 29
<211> LENGTH: 32
<212> TYPE: PRT
<213> ORGANISM: Artificial sequence
<220> FEATURE:
<223> OTHER INFORMATION: Chimeric

<400> SEQUENCE: 29

Gly Val Pro Ser Arg Phe Ser Gly Ser Gly Ser Gly Thr Asp Tyr
 1               5                  10                  15

Ser Leu Thr Ile Ser Asn Leu Glu Pro Glu Asp Ile Ala Thr Tyr
                 20                  25                  30

Tyr Cys

<210> SEQ ID NO 30
<211> LENGTH: 10
<212> TYPE: PRT
<213> ORGANISM: Artificial sequence
<220> FEATURE:
<223> OTHER INFORMATION: Chimeric

<400> SEQUENCE: 30

Phe Gly Gly Gly Thr Lys Val Glu Ile Lys
 1               5                  10

<210> SEQ ID NO 31
<211> LENGTH: 25
<212> TYPE: PRT
<213> ORGANISM: Artificial sequence
<220> FEATURE:
<223> OTHER INFORMATION: Chimeric
```

<400> SEQUENCE: 31

Gln Val Gln Leu Lys Glu Ser Gly Pro Gly Leu Val Ala Pro Ser
1               5                   10                  15

Gln Ser Leu Ser Leu Thr Cys Thr Val Ser
            20                  25

<210> SEQ ID NO 32
<211> LENGTH: 14
<212> TYPE: PRT
<213> ORGANISM: Artificial sequence
<220> FEATURE:
<223> OTHER INFORMATION: Chimeric

<400> SEQUENCE: 32

Trp Val Arg Gln Pro Pro Gly Lys Gly Leu Glu Trp Leu Gly
1               5                   10

<210> SEQ ID NO 33
<211> LENGTH: 32
<212> TYPE: PRT
<213> ORGANISM: Artificial sequence
<220> FEATURE:
<223> OTHER INFORMATION: Chimeric

<400> SEQUENCE: 33

Arg Leu Thr Ile Ser Lys Asp Asn Ser Lys Ser Gln Val Phe Leu
1               5                   10                  15

Lys Met Asn Ser Leu Gln Thr Asp Asp Thr Ala Arg Tyr Tyr Cys
            20                  25                  30

Ala Arg

<210> SEQ ID NO 34
<211> LENGTH: 11
<212> TYPE: PRT
<213> ORGANISM: Artificial sequence
<220> FEATURE:
<223> OTHER INFORMATION: Chimeric

<400> SEQUENCE: 34

Trp Gly Pro Gly Thr Leu Val Thr Val Ser Ala
1               5                   10

<210> SEQ ID NO 35
<211> LENGTH: 131
<212> TYPE: PRT
<213> ORGANISM: Macaca mulatta

<400> SEQUENCE: 35

Met Lys Ile Phe Leu Pro Val Leu Leu Ala Ala Leu Leu Gly Val
1               5                   10                  15

Glu Arg Ala Ser Ser Leu Met Cys Phe Ser Cys Leu Asn Gln Lys
            20                  25                  30

Ser Asn Leu Tyr Cys Leu Lys Pro Thr Ile Cys Ser Asp Gln Asp
                35                  40                  45

Asn Tyr Cys Val Thr Val Ser Thr Ser Ala Gly Ile Gly Asn Leu
                50                  55                  60

Val Thr Phe Gly His Ser Leu Ser Lys Thr Cys Ser Pro Ala Cys
                65                  70                  75

Pro Leu Pro Glu Gly Ile Asn Val Gly Val Ala Ser Met Gly Ile
                80                  85                  90

-continued

```
Ser Cys Cys Gln Ser Phe Leu Cys Asn Phe Ser Ala Ala Asp Gly
                95                 100                 105

Gly Leu Arg Ala Ser Ala Thr Leu Leu Gly Ala Gly Leu Leu Leu
            110                 115                 120

Ser Leu Leu Pro Ala Leu Leu Arg Phe Gly Pro
            125                 130

<210> SEQ ID NO 36
<211> LENGTH: 136
<212> TYPE: PRT
<213> ORGANISM: Mus musculus

<400> SEQUENCE: 36

Met Ser Ala Thr Ser Asn Met Arg Val Phe Leu Pro Val Leu Leu
 1               5                  10                  15

Ala Ala Leu Leu Gly Met Glu Gln Val His Ser Leu Met Cys Phe
            20                  25                  30

Ser Cys Thr Asp Gln Lys Asn Asn Ile Asn Cys Leu Trp Pro Val
            35                  40                  45

Ser Cys Gln Glu Lys Asp His Tyr Cys Ile Thr Leu Ser Ala Ala
            50                  55                  60

Ala Gly Phe Gly Asn Val Asn Leu Gly Tyr Thr Leu Asn Lys Gly
            65                  70                  75

Cys Ser Pro Ile Cys Pro Ser Glu Asn Val Asn Leu Asn Leu Gly
            80                  85                  90

Val Ala Ser Val Asn Ser Tyr Cys Cys Gln Ser Ser Phe Cys Asn
            95                  100                 105

Phe Ser Ala Ala Gly Leu Gly Leu Arg Ala Ser Ile Pro Leu Leu
            110                 115                 120

Gly Leu Gly Leu Leu Ser Leu Leu Ala Leu Leu Gln Leu Ser
            125                 130                 135

Pro

<210> SEQ ID NO 37
<211> LENGTH: 136
<212> TYPE: PRT
<213> ORGANISM: Rattus norvegicus

<400> SEQUENCE: 37

Met Ser Ala Ala Ser Ser Met Arg Val Phe Leu Pro Val Leu Leu
 1               5                  10                  15

Ala Ala Leu Leu Gly Val Glu Gln Val His Ser Leu Met Cys Phe
            20                  25                  30

Ser Cys Thr Asp Gln Lys Asn Asn Ile Asn Cys Leu Trp Pro Val
            35                  40                  45

Ser Cys Ser Ser Thr Asp Asn Tyr Cys Ile Thr Leu Ser Ala Ala
            50                  55                  60

Ala Gly Phe Gly Asn Val Asn Leu Gly Tyr Thr Leu Asn Lys Gly
            65                  70                  75

Cys Ser Pro Thr Cys Pro Arg Glu Asn Ile Asn Ile Asn Leu Gly
            80                  85                  90

Val Ala Ser Val Asn Ser Tyr Cys Cys Gln Ser Ser Phe Cys Asn
            95                  100                 105

Phe Ser Thr Ala Gly Leu Gly Leu Arg Ala Ser Ile Pro Leu Leu
            110                 115                 120

Gly Leu Gly Leu Leu Leu Ser Leu Leu Ala Val Leu Arg Leu Ser
```

-continued

```
                125                 130                 135
Pro

<210> SEQ ID NO 38
<211> LENGTH: 111
<212> TYPE: PRT
<213> ORGANISM: Homo sapiens

<400> SEQUENCE: 38

Leu Met Cys Phe Ser Cys Leu Asn Gln Lys Ser Asn Leu Tyr Cys
  1               5                  10                  15

Leu Lys Pro Thr Ile Cys Ser Asp Gln Asp Asn Tyr Cys Val Thr
                 20                  25                  30

Val Ser Ala Ser Ala Gly Ile Gly Asn Leu Val Thr Phe Gly His
                 35                  40                  45

Ser Leu Ser Lys Thr Cys Ser Pro Ala Cys Pro Ile Pro Glu Gly
                 50                  55                  60

Val Asn Val Gly Val Ala Ser Met Gly Ile Ser Cys Cys Gln Ser
                 65                  70                  75

Phe Leu Cys Asn Phe Ser Ala Ala Asp Gly Gly Leu Arg Ala Ser
                 80                  85                  90

Val Thr Leu Leu Gly Ala Gly Leu Leu Leu Ser Leu Leu Pro Ala
                 95                 100                 105

Leu Leu Arg Phe Gly Pro
                110

<210> SEQ ID NO 39
<211> LENGTH: 111
<212> TYPE: PRT
<213> ORGANISM: Macaca fascicularis

<400> SEQUENCE: 39

Leu Met Cys Phe Ser Cys Leu Asn Gln Lys Ser Asn Leu Tyr Cys
  1               5                  10                  15

Leu Lys Pro Thr Ile Cys Ser Asp Gln Asp Asn Tyr Cys Val Thr
                 20                  25                  30

Val Ser Thr Ser Ala Gly Ile Gly Asn Leu Val Thr Phe Gly His
                 35                  40                  45

Ser Leu Ser Lys Thr Cys Ser Pro Ala Cys Pro Leu Pro Glu Gly
                 50                  55                  60

Ile Asn Val Gly Val Ala Ser Met Gly Ile Ser Cys Cys Gln Ser
                 65                  70                  75

Phe Leu Cys Asn Phe Ser Ala Ala Asp Gly Gly Leu Arg Ala Ser
                 80                  85                  90

Ala Thr Leu Leu Gly Ala Gly Leu Leu Leu Ser Leu Leu Pro Ala
                 95                 100                 105

Leu Leu Arg Phe Gly Pro
                110

<210> SEQ ID NO 40
<211> LENGTH: 111
<212> TYPE: PRT
<213> ORGANISM: Macaca mulatta

<400> SEQUENCE: 40

Leu Met Cys Phe Ser Cys Leu Asn Gln Lys Ser Asn Leu Tyr Cys
  1               5                  10                  15
```

Leu Lys Pro Thr Ile Cys Ser Asp Gln Asp Asn Tyr Cys Val Thr
                20                  25                  30

Val Ser Thr Ser Ala Gly Ile Gly Asn Leu Val Thr Phe Gly His
            35                  40                  45

Ser Leu Ser Lys Thr Cys Ser Pro Ala Cys Pro Leu Pro Glu Gly
            50                  55                  60

Ile Asn Val Gly Val Ala Ser Met Gly Ile Ser Cys Cys Gln Ser
            65                  70                  75

Phe Leu Cys Asn Phe Ser Ala Ala Asp Gly Gly Leu Arg Ala Ser
            80                  85                  90

Ala Thr Leu Leu Gly Ala Gly Leu Leu Leu Ser Leu Leu Pro Ala
            95                  100                 105

Leu Leu Arg Phe Gly Pro
                110

<210> SEQ ID NO 41
<211> LENGTH: 110
<212> TYPE: PRT
<213> ORGANISM: Mus musculus

<400> SEQUENCE: 41

Leu Met Cys Phe Ser Cys Thr Asp Gln Lys Asn Asn Ile Asn Cys
 1               5                  10                  15

Leu Trp Pro Val Ser Cys Gln Glu Lys Asp His Tyr Cys Ile Thr
                20                  25                  30

Leu Ser Ala Ala Gly Phe Gly Asn Val Asn Leu Gly Tyr Thr
            35                  40                  45

Leu Asn Lys Gly Cys Ser Pro Ile Cys Pro Ser Glu Asn Val Asn
            50                  55                  60

Leu Asn Leu Gly Val Ala Ser Val Asn Ser Tyr Cys Cys Gln Ser
            65                  70                  75

Ser Phe Cys Asn Phe Ser Ala Ala Gly Leu Gly Leu Arg Ala Ser
            80                  85                  90

Ile Pro Leu Leu Gly Leu Gly Leu Leu Leu Ser Leu Leu Ala Leu
            95                  100                 105

Leu Gln Leu Ser Pro
                110

<210> SEQ ID NO 42
<211> LENGTH: 110
<212> TYPE: PRT
<213> ORGANISM: Rattus norvegicus

<400> SEQUENCE: 42

Leu Met Cys Phe Ser Cys Thr Asp Gln Lys Asn Asn Ile Asn Cys
 1               5                  10                  15

Leu Trp Pro Val Ser Cys Ser Ser Thr Asp Asn Tyr Cys Ile Thr
                20                  25                  30

Leu Ser Ala Ala Gly Phe Gly Asn Val Asn Leu Gly Tyr Thr
            35                  40                  45

Leu Asn Lys Gly Cys Ser Pro Thr Cys Pro Arg Glu Asn Ile Asn
            50                  55                  60

Ile Asn Leu Gly Val Ala Ser Val Asn Ser Tyr Cys Cys Gln Ser
            65                  70                  75

Ser Phe Cys Asn Phe Ser Thr Ala Gly Leu Gly Leu Arg Ala Ser
            80                  85                  90

Ile Pro Leu Leu Gly Leu Gly Leu Leu Ser Leu Leu Ala Val
                95                 100                105

Leu Arg Leu Ser Pro
            110

<210> SEQ ID NO 43
<211> LENGTH: 120
<212> TYPE: PRT
<213> ORGANISM: Artificial sequence
<220> FEATURE:
<223> OTHER INFORMATION: Humanized

<400> SEQUENCE: 43

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Ser Leu Thr
                20                  25                  30

Gly Tyr Ser Val Asn Trp Val Arg Gln Ala Pro Gly Lys Gly Leu
                35                  40                  45

Glu Trp Val Gly Met Ile Trp Gly Asp Gly Ser Thr Asp Tyr Asn
                50                  55                  60

Ser Ala Leu Lys Ser Arg Phe Thr Ile Ser Arg Asp Asn Ser Lys
                65                  70                  75

Asn Thr Leu Tyr Leu Gln Met Asn Ser Leu Arg Ala Glu Asp Thr
                80                  85                  90

Ala Val Tyr Tyr Cys Ala Arg Asp Tyr Tyr Phe Asn Tyr Ala Ser
                95                  100                 105

Trp Phe Ala Tyr Trp Gly Gln Gly Thr Leu Val Thr Val Ser Ser
                110                 115                 120

<210> SEQ ID NO 44
<211> LENGTH: 120
<212> TYPE: PRT
<213> ORGANISM: Artificial sequence
<220> FEATURE:
<223> OTHER INFORMATION: Chimeric

<400> SEQUENCE: 44

Gln Val Gln Leu Lys Glu Ser Gly Pro Gly Leu Val Ala Pro Ser
 1               5                  10                  15

Gln Ser Leu Ser Leu Thr Cys Thr Val Ser Gly Phe Ser Leu Thr
                20                  25                  30

Gly Tyr Ser Val Asn Trp Val Arg Gln Pro Pro Gly Lys Gly Leu
                35                  40                  45

Glu Trp Leu Gly Met Ile Trp Gly Asp Gly Ser Thr Asp Tyr Asn
                50                  55                  60

Ser Ala Leu Lys Ser Arg Leu Thr Ile Ser Lys Asp Asn Ser Lys
                65                  70                  75

Ser Gln Val Phe Leu Lys Met Asn Ser Leu Gln Thr Asp Asp Thr
                80                  85                  90

Ala Arg Tyr Tyr Cys Ala Arg Asp Tyr Tyr Phe Asn Tyr Ala Ser
                95                  100                 105

Trp Phe Ala Tyr Trp Gly Pro Gly Thr Leu Val Thr Val Ser Ala
                110                 115                 120

<210> SEQ ID NO 45
<211> LENGTH: 107
<212> TYPE: PRT
<213> ORGANISM: Homo sapiens -continued

<400> SEQUENCE: 45

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Ser
                20                  25                  30

Ser Tyr Leu Ala Trp Tyr Gln Gln Lys Pro Gly Lys Ala Pro Lys
                35                  40                  45

Leu Leu Ile Tyr Ala Ala Ser Ser Leu Gln Ser Gly Val Pro Ser
                50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
                80                  85                  90

Tyr Tyr Ser Tyr Pro Phe Thr Phe Gly Gln Gly Thr Lys Val Glu
                95                  100                 105

Ile Lys

<210> SEQ ID NO 46
<211> LENGTH: 118
<212> TYPE: PRT
<213> ORGANISM: Homo sapiens

<400> SEQUENCE: 46

Glu Val Gln Leu Val Glu Ser Gly Pro Ala Leu Val Lys Pro Thr
1               5                   10                  15

Gln Thr Leu Thr Leu Thr Cys Thr Phe Ser Gly Phe Ser Leu Ser
                20                  25                  30

Thr Ser Gly Val Gly Val Ser Trp Ile Arg Gln Pro Pro Gly Lys
                35                  40                  45

Ala Leu Glu Trp Leu Ala Leu Ile Asp Trp Asn Asp Asp Lys Arg
                50                  55                  60

Tyr Ser Thr Ser Leu Lys Ser Arg Leu Thr Ile Ser Lys Asp Thr
65                  70                  75

Ser Lys Asn Gln Val Val Leu Thr Met Thr Asn Met Asp Pro Val
                80                  85                  90

Asp Thr Ala Thr Tyr Tyr Cys Ala Arg Asp Thr Ala Ala Tyr Phe
                95                  100                 105

Asp Tyr Trp Gly Gln Gly Thr Leu Val Thr Val Ser Ser
                110                 115

<210> SEQ ID NO 47
<211> LENGTH: 112
<212> TYPE: PRT
<213> ORGANISM: Homo sapiens

<400> SEQUENCE: 47

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser
                20                  25                  30

Ser Tyr Ala Met Ser Trp Val Arg Gln Ala Pro Gly Lys Gly Leu
                35                  40                  45

Glu Trp Val Gly Ala Ile Ser Ser Ser Gly Ser Ser Thr Tyr Tyr
    50                  55                  60

Ala Asp Ser Val Lys Gly Arg Phe Thr Ile Ser Arg Asp Asn Ser
65                  70                  75

Lys Asn Thr Leu Tyr Leu Gln Met Asn Ser Leu Arg Ala Glu Asp
            80                  85                  90

Thr Ala Val Tyr Tyr Cys Ala Arg Phe Asp Tyr Trp Gly Gln Gly
                95                 100                 105

Thr Leu Val Thr Val Ser Ser
            110

<210> SEQ ID NO 48
<211> LENGTH: 21
<212> TYPE: DNA
<213> ORGANISM: Homo sapiens

<400> SEQUENCE: 48
gtgcctgatc tgtgcccttg g                                           21

<210> SEQ ID NO 49
<211> LENGTH: 20
<212> TYPE: DNA
<213> ORGANISM: Homo sapiens

<400> SEQUENCE: 49
cccggaagtg gcagaaaccc                                             20

<210> SEQ ID NO 50
<211> LENGTH: 423
<212> TYPE: DNA
<213> ORGANISM: Homo sapiens

<400> SEQUENCE: 50
gtgcctgatc tgtgcccttg gtcccaggtc aggcccaccc cctgcacctc            50
cacctgcccc agcccctgcc tctgcccaag tgggccagct gccctcactt            100
ctggggtgga tgatgtgacc ttccttgggg gactgcggaa gggacgaggg            150
ttccctggag tcttacggtc aacatcaga ccaagtccca tggacatgct             200
gacagggtcc ccagggagac cgtgtcagta gggatgtgtg cctggctgtg            250
tacgtgggtg tgcagtgcac gtgagagcac gtggcggctt ctgggggcca            300
tgtttgggga gggaggtgtg ccagcagcct ggagagcctc agtccctgta            350 gcccctgcc ctggcacagc tgcatgcact tcaagggcag cctttgggggg           400 ttggggtttc tgccacttcc ggg                                         423

<210> SEQ ID NO 51
<211> LENGTH: 19
<212> TYPE: DNA
<213> ORGANISM: Homo sapiens

<400> SEQUENCE: 51
agcggattct catggaaca                                              19

<210> SEQ ID NO 52
<211> LENGTH: 18
<212> TYPE: DNA
<213> ORGANISM: Homo sapiens

```
<400> SEQUENCE: 52
ctggtcagcc aggagctt                                                    18

<210> SEQ ID NO 53
<211> LENGTH: 24
<212> TYPE: DNA
<213> ORGANISM: Homo sapiens

<400> SEQUENCE: 53
tccacaagct gaaggcagac aagg                                             24

<210> SEQ ID NO 54
<211> LENGTH: 19
<212> TYPE: DNA
<213> ORGANISM: Homo sapiens

<400> SEQUENCE: 54
agaaggcgtc aatgttggt                                                   19

<210> SEQ ID NO 55
<211> LENGTH: 21
<212> TYPE: DNA
<213> ORGANISM: Homo sapiens

<400> SEQUENCE: 55
cactgaaatt gcacagaaag c                                                21

<210> SEQ ID NO 56
<211> LENGTH: 21
<212> TYPE: DNA
<213> ORGANISM: Homo sapiens

<400> SEQUENCE: 56
ttccatgggc atcagctgct g                                                21
```

ANTI-LY6E ANTIBODIES AND IMMUNOCONJUGATES AND METHODS OF USE

CROSS REFERENCE TO RELATED APPLICATIONS

This application is a 35 USC 371 of International Patent Application No. PCT/US2013/041848, filed May 20, 2013; which claims priority benefit to U.S. Provisional 61/649,775 filed May 21, 2012, the contents of each of which are hereby incorporated herein by reference in their entireties.

FIELD OF THE INVENTION

The present invention relates to anti-Ly6E antibodies and immunoconjugates and methods of using the same.

BACKGROUND

Lymphocyte antigen 6 complex, locus E (Ly6E), also known as retinoic acid induced gene E (RIG-E) and stem cell antigen 2 (SCA-2). It is a GPI linked, 131 amino acid length, ~8.4 kDa protein of unknown function with no known binding partners. It was initially identified as a transcript expressed in immature thymocyte, thymic medullary epithelial cells in mice. *RIG-E, a human homolog of the murine Ly-6 family, is induced by retinoic acid during the differentiation of acute promyelocytic leukemia cell*. Mao M., Yu M., Tong J.-H., Ye J., Zhu J., Huang Q.-H., Fu G., Yu L., Zhao S.-Y., Waxman S., Lanotte M., Wang Z.-Y., Tan J.-Z., Chan S.-J., Chen Z. Proc. Natl. Acad. Sci. U.S.A. 93:5910-5914 (1996).

There is a need in the art for agents that target Ly6E for the diagnosis and treatment of Ly6E-associated conditions, such as cancer. The invention fulfills that need and provides other benefits.

SUMMARY OF THE INVENTION

The invention provides anti-Ly6E antibodies, immunoconjugates and methods of using the same.

In some embodiments, an isolated antibody that binds to Ly6E is provided. In other embodiments the antibody that binds to Ly6E binds to an epitope within amino acids 21-131 of SEQ ID NO:1. In another embodiment, such an antibody binds Ly6E with an affinity of ≤4 nM as measured by scatchard analysis. In another embodiment, such an antibody binds Ly6E with an affinity of ≤7 nM as measured by surface plasmon resonance (SPR). In yet another embodiment, such an antibody is used as a medicament.

In one embodiment, an antibody that binds to an epitope within amino acids 21-131 of SEQ ID NO:1 binds with an affinity of ≤4 nM as measured by scatchard analysis, or binds Ly6E with an affinity of ≤7 nM as measured by SPR is a monoclonal antibody. In another embodiment, such an antibody is a human, humanized, or chimeric antibody.

In one embodiment, an antibody that binds to an epitope within amino acids 21-131 of SEQ ID NO:1 binds with an affinity of ≤4 nM as measured by scatchard analysis, and is internalized in a Ly6E-expressing cell upon binding to said epitope within amino acids 21-131 of SEQ ID NO:1. In another embodiment, an antibody that binds to an epitope within amino acids 21-131 of SEQ ID NO:1 binds Ly6E with an affinity of ≤7 nM as measured by SPR and is internalized in a Ly6E-expressing cell upon binding to said epitope within amino acids 21-131 of SEQ ID NO:1.

In one embodiment, an antibody that binds to an epitope within amino acids 21-131 of SEQ ID NO:1 binds with an affinity of ≤4 nM as measured by scatchard analysis or binds Ly6E with an affinity of ≤7 nM as measured by SPR, wherein the antibody comprises (a) HVR-H3 comprising the amino acid sequence of SEQ ID NO:12, (b) HVR-L3 comprising the amino acid sequence of SEQ ID NO:9, and (c) HVR-H2 comprising the amino acid sequence of SEQ ID NO:11. In another embodiment, such an antibody comprises (a) HVR-H1 comprising the amino acid sequence of SEQ ID NO:10, (b) HVR-H2 comprising the amino acid sequence of SEQ ID NO:11, and (c) HVR-H3 comprising the amino acid sequence of SEQ ID NO:12. In yet another embodiment, the antibody described above further comprises (a) HVR-L1 comprising the amino acid sequence of SEQ ID NO:7; (b) HVR-L2 comprising the amino acid sequence of SEQ ID NO:8; and (c) HVR-L3 comprising the amino acid sequence of SEQ ID NO:9. In yet another embodiment, such an antibody comprises (a) HVR-L1 comprising the amino acid sequence of SEQ ID NO:7; (b) HVR-L2 comprising the amino acid sequence of SEQ ID NO:8; and (c) HVR-L3 comprising the amino acid sequence of SEQ ID NO:9.

In one embodiment, for an antibody comprising (a) HVR-H1 comprising the amino acid sequence of SEQ ID NO:10, (b) HVR-H2 comprising the amino acid sequence of SEQ ID NO:11, and (c) HVR-H3 comprising the amino acid sequence of SEQ ID NO:12 and (d) HVR-H1 comprising the amino acid sequence of SEQ ID NO:10, (e) HVR-H2 comprising the amino acid sequence of SEQ ID NO:11, and (f) HVR-H3 comprising the amino acid sequence of SEQ ID NO:12, it further comprises a light chain variable domain framework FR2 sequence of SEQ ID NO:20 or light chain variable domain framework FR3 of SEQ ID NO:21 or heavy chain variable domain framework FR1 or SEQ ID NO:23, or heavy chain variable domain framework FR2 of SEQ ID NO:24.

In one embodiment, an antibody that binds to an epitope within amino acids 21-131 of SEQ ID NO:1 binds with an affinity of ≤4 nM as measured by scatchard analysis or binds Ly6E with an affinity of ≤7 nM as measured by SPR, and comprises (a) a VH sequence having at least 95% sequence identity to the amino acid sequence of SEQ ID NO:5; (b) a VL sequence having at least 95% sequence identity to the amino acid sequence of SEQ ID NO:3; or (c) a VH sequence as in (a) and a VL sequence as in (b). In another embodiment, such an antibody comprises a VH sequence of SEQ ID NO:5. In yet another embodiment, such an antibody further comprises a VL sequence of SEQ ID NO:3.

In one embodiment, an antibody that binds to an epitope within amino acids 21-131 of SEQ ID NO:1 binds with an affinity of ≤4 nM as measured by scatchard analysis, comprises a VH sequence of SEQ ID NO:5 and a VL sequence of SEQ ID NO:3. In another embodiment, an antibody that binds to an epitope within amino acids 21-131 of SEQ ID NO:1 binds with an affinity of ≤7 nM as measured by SPR, comprises a VH sequence of SEQ ID NO:5 and a VL sequence of SEQ ID NO:3.

In one embodiment, an antibody that binds to an epitope within amino acids 21-131 of SEQ ID NO:1 binds with an affinity of ≤4 nM as measured by scatchard analysis, which is an IgG1, IgG2a or IgG2b. In one embodiment, an antibody that binds to an epitope within amino acids 21-131 of SEQ ID NO:1 binds with an affinity of ≤7 nM as measured by SPR, which is an IgG1, IgG2a or IgG2b.

In one embodiment, isolated nucleic acids encoding an antibody as described herein is provided. In another embodiment, a host cell comprising such an isolated nucleic acid is also provided. In yet another embodiment, a method of producing an antibody comprising culturing the host cell comprising an isolated nucleic acid as described herein so that the antibody is produced is also provided.

In one embodiment, an immunoconjugate comprising an antibody as described herein and a cytotoxic agent is provided. In another embodiment, such an immunoconjugate has the formula Ab-(L-D)p, wherein: (a) Ab is an antibody as described herein; (b) L is a linker; (c) D is a drug selected from a maytansinoid, an auristatin, a calicheamicin, a pyrrolobenzodiazepine, and a nemorubicin derivative; and (d) p ranges from 1-8. In some embodiments, such an immunoconjugate has D as an auristatin. In other embodiments, such an immunoconjugate has D having formula $D_E$:

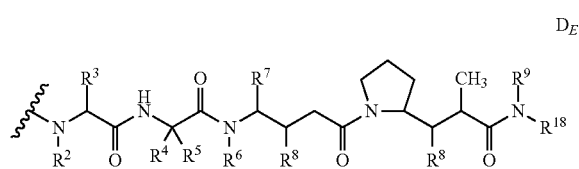

wherein $R^2$ and $R^6$ are each methyl, $R^3$ and $R^4$ are each isopropyl, $R^5$ is H, $R^7$ is sec-butyl, each $R^8$ is independently selected from $CH_3$, $O-CH_3$, OH, and H; $R^9$ is H; and $R^{18}$ is $-C(R^8)_2-C(R^8)_2$-aryl.

In other embodiments, an immunoconjugate described herein, has as its drug, MMAE having the structure:

In one embodiment, the immunoconjugate described herein, has D as a pyrrolobenzodiazepine of Formula A:

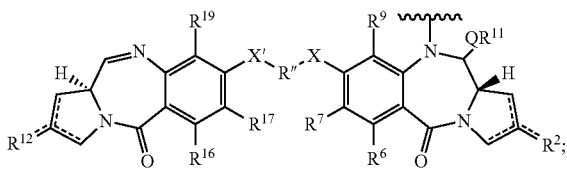

wherein the dotted lines indicate the optional presence of a double bond between C1 and C2 or C2 and C3; $R^2$ is independently selected from H, OH, =O, $=CH_2$, CN, R, OR, $=CH-R^D$, $=C(R^D)_2$, $O-SO_2-R$, $CO_2R$ and COR, and optionally further selected from halo or dihalo, wherein $R^D$ is independently selected from R, $CO_2R$, COR, CHO, $CO_2H$, and halo; $R^6$ and $R^9$ are independently selected from H, R, OH, OR, SH, SR, $NH_2$, NHR, NRR', $NO_2$, $Me_3Sn$ and halo; $R^7$ is independently selected from H, R, OH, OR, SH, SR, $NH_2$, NHR, NRR', $NO_2$, $Me_3Sn$ and halo; Q is independently selected from O, S and NH; $R^{11}$ is either H, or R or, where Q is O, $SO_3M$, where M is a metal cation; R and R' are each independently selected from optionally substituted $C_{1-8}$ alkyl, $C_{3-8}$ heterocyclyl and $C_{5-20}$ aryl groups, and optionally in relation to the group NRR', R and R' together with the nitrogen atom to which they are attached form an optionally substituted 4-, 5-, 6- or 7-membered heterocyclic ring; $R^{12}$, $R^{16}$, $R^{19}$ and $R^{17}$ are as defined for $R^2$, $R^6$, $R^9$ and $R^7$ respectively; R" is a $C_{3-12}$ alkylene group, which chain may be interrupted by one or more heteroatoms and/or aromatic rings that are optionally substituted; and X and X' are independently selected from O, S and N(H). In some embodiments, the immunoconjugate as described herein, D has the structure:

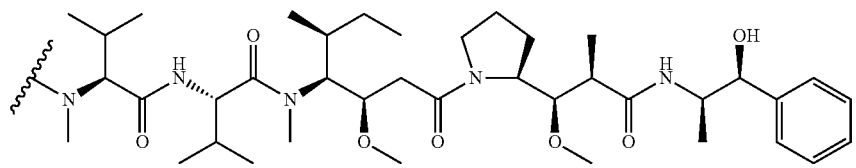

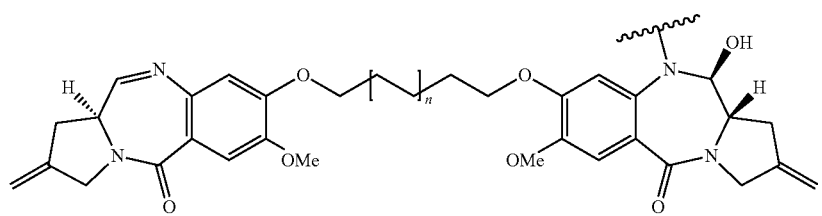

wherein n is 0 or 1.

In one embodiment, the immunoconjugate as described herein, D is a nemorubicin derivative. In another embodiment, D has a structure selected from:

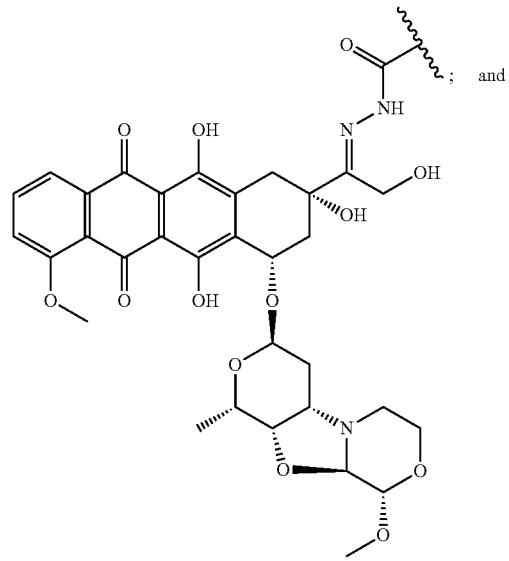

; and

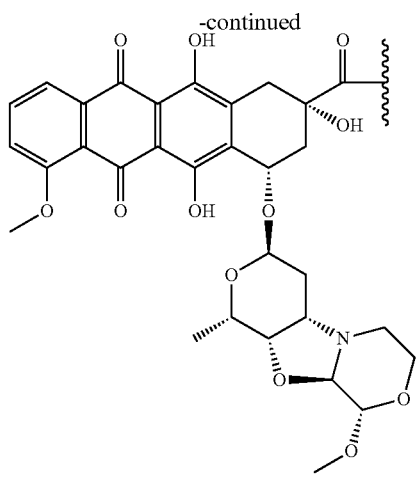

In one embodiment, an immunoconjugate as described herein comprises a linker that is cleavable by a protease. In other embodiments, the linker comprises a val-cit dipeptide or a Phe-Lys dipeptide. In yet another embodiment, an immunoconjugate comprises a linker that is acid-labile. In other embodiments, the linker comprises hydrazone.

In one embodiment, an immunoconjugate has a formula selected from:

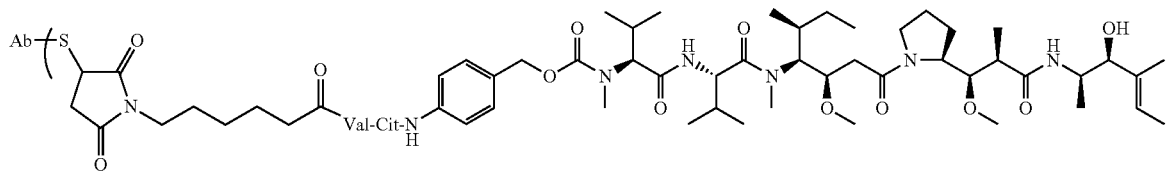

wherein S is a sulfur atom;

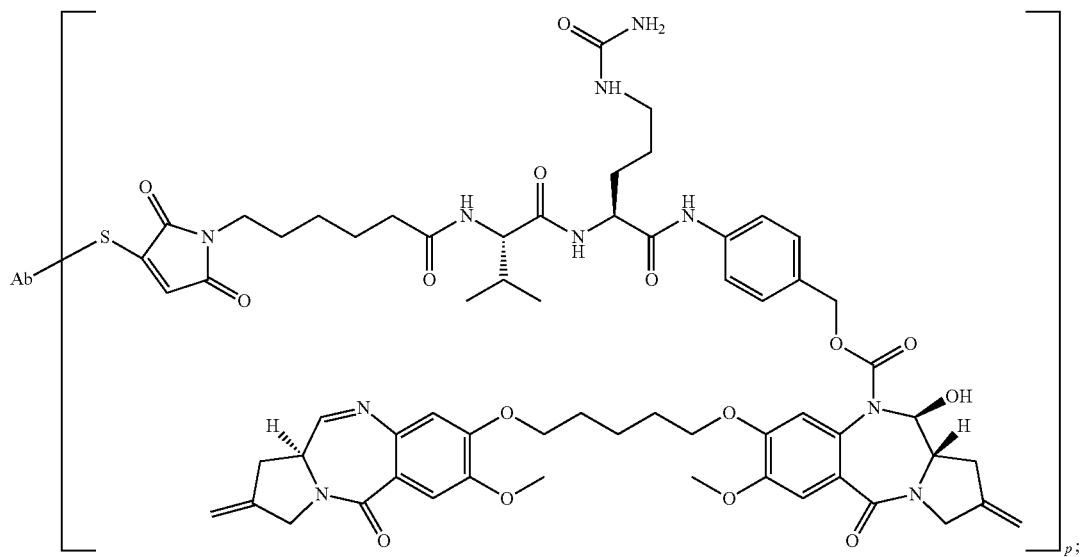
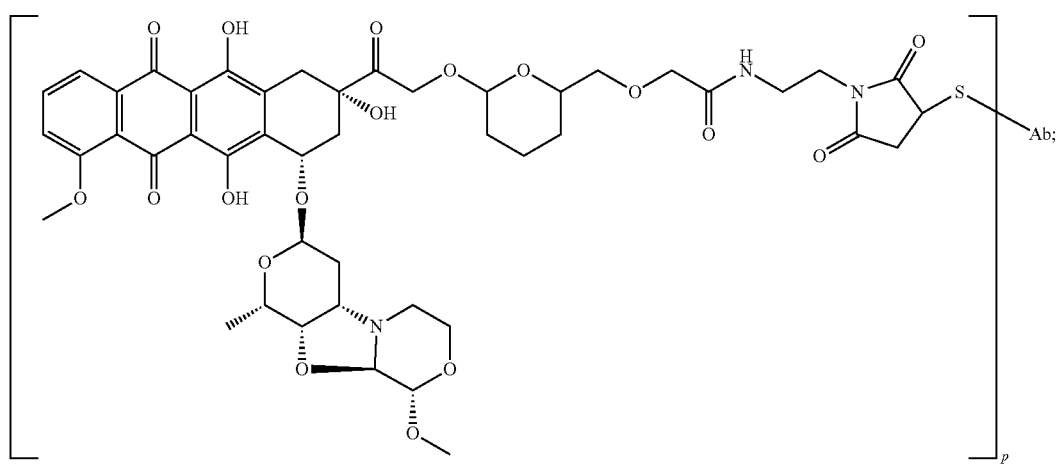
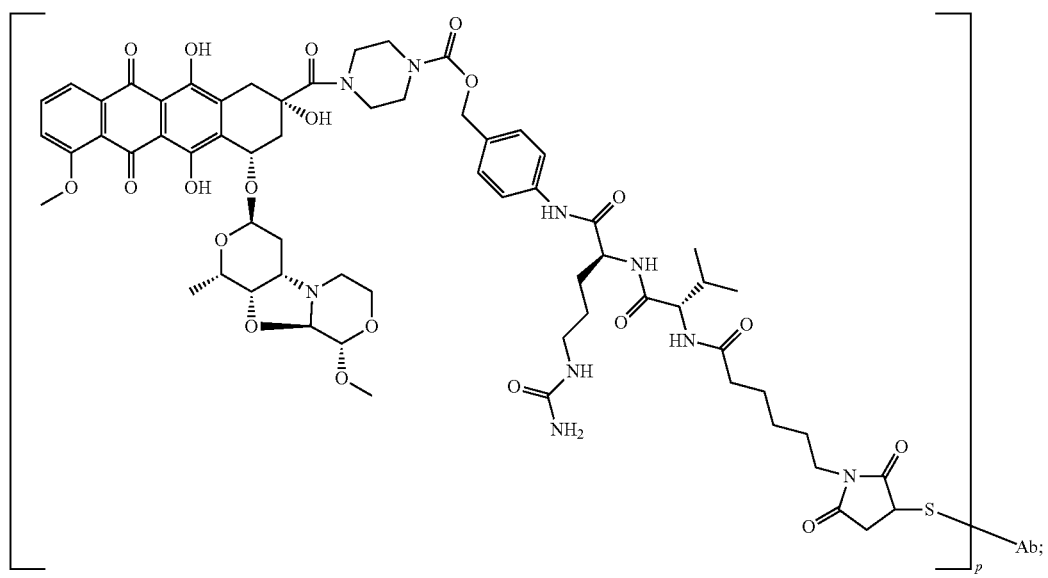

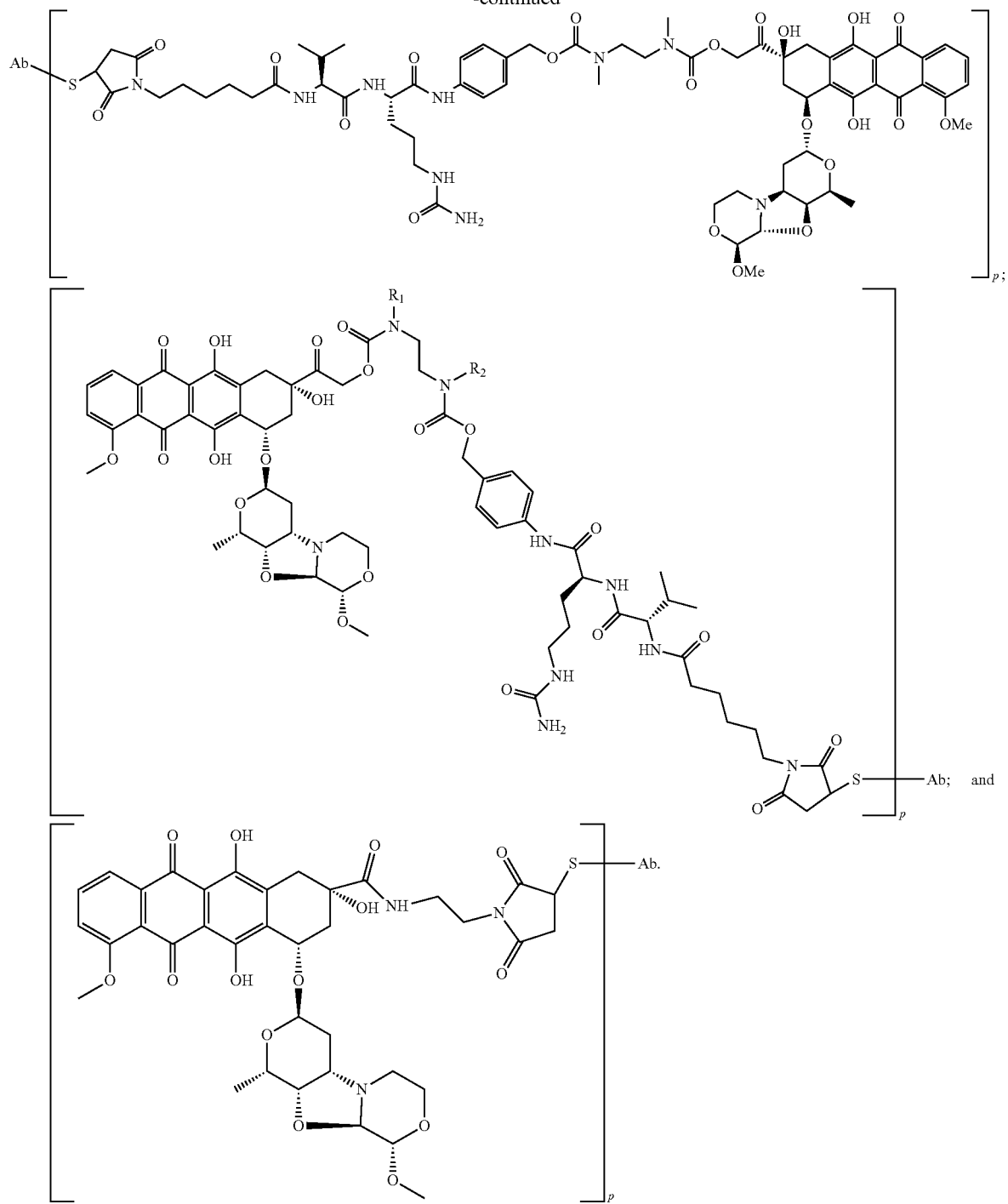

In some embodiments, p ranges from 2-5.

In one embodiment, an immunoconjugate of the invention as described herein comprises an antibody comprising (a) HVR-H1 comprising the amino acid sequence of SEQ ID NO:10, (b) HVR-H2 comprising the amino acid sequence of SEQ ID NO:11, (c) HVR-H3 comprising the amino acid sequence of SEQ ID NO:12, (d) HVR-L1 comprising the amino acid sequence of SEQ ID NO:7; (e) HVR-L2 comprising the amino acid sequence of SEQ ID NO:8; and (f) HVR-L3 comprising the amino acid sequence of SEQ ID NO:9. In another embodiment, an immunoconjugate of the invention as described herein comprises a VH sequence of SEQ ID NO:5 and a VL sequence of SEQ ID NO:3.

In one embodiment, a pharmaceutical formulation comprising the immunoconjugate of the invention as described herein and a pharmaceutically acceptable carrier is provided. In some embodiments, a pharmaceutical formulation further comprises an additional therapeutic agent. In some embodiments, the additional therapeutic agent is a chemotherapeutic agent, such as, for example, a platinum complex.

In one embodiment, methods of treating an individual having a Ly6E-positive cancer are provided. In some embodiments, such methods comprise administering a pharmaceutical formulation comprising an immunoconjugate of the invention as described herein comprising an antibody that binds Ly6E, e.g., as described herein. In other embodiments, the Ly6E-positive cancer is selected from breast cancer, pancreatic cancer, colon cancer, colorectal cancer, melanoma, ovarian cancer, non-small cell lung cancer, or gastric cancer. In some embodiments, a method of the invention comprises administering an additional therapeutic agent to the individual. In some embodiments, the additional therapeutic agent is a chemotherapeutic agent, such as, for example, a platinum complex.

In some embodiments, methods of inhibiting proliferation of a Ly6E-positive cell are provided. In one embodiment, such methods comprise exposing a Ly6E-positive cell to an immunoconjugate of the invention as described herein comprising an antibody that binds Ly6E under conditions permissive for binding of the immunoconjugate to Ly6E on the surface of the cell. In some embodiments, an antibody that binds Ly6E is an antibody as described herein. In some embodiments, proliferation of the Ly6E-positive cell is thereby inhibited. In some embodiments, the cell is a breast cancer cell, pancreatic cancer cell, colon cancer cell, colorectal cancer cell, melanoma cell, ovarian cancer cell, non-small cell lung cancer cell, or gastric cancer cell.

In one embodiment, an antibody that binds Ly6E as described herein is conjugated to a label. In some embodiments, such a label is a positron emitter. In some embodiments, the positron emitter is $^{89}$Zr.

In some embodiments, a method of detecting human Ly6E in a biological sample is provided. In some embodiments, such a method comprises contacting the biological sample with an anti-Ly6E antibody under conditions permissive for binding of the anti-Ly6E antibody to a naturally occurring human Ly6E, and detecting whether a complex is formed between the anti-Ly6E antibody and a naturally occurring human Ly6E in the biological sample. In some embodiments, an anti-Ly6E antibody is an antibody described herein. In some embodiments, the biological sample is a breast cancer sample, pancreatic cancer sample, colon cancer sample, colorectal cancer sample, melanoma sample, ovarian cancer sample, non-small cell lung cancer sample, or gastric cancer sample.

In one embodiment, a method for detecting a Ly6E-positive cancer is provided. In such embodiments, a method comprises (i) administering a labeled anti-Ly6E antibody to a subject having or suspected of having a Ly6E-positive cancer, and (ii) detecting the labeled anti-Ly6E antibody in the subject, wherein detection of the labeled anti-Ly6E antibody indicates a Ly6E-positive cancer in the subject. In some embodiments, an anti-Ly6E antibody is an antibody described herein. In other embodiments, the Ly6E-positive cancer is selected from breast cancer, pancreatic cancer, colon cancer, colorectal cancer, melanoma, ovarian cancer, non-small cell lung cancer, or gastric cancer. In one embodiment of the method described herein, an antibody that binds Ly6E as described herein is conjugated to a label. In some embodiments, such a label is a positron emitter. In some embodiments, the positron emitter is $^{89}$Zr.

In some embodiments, an isolated antibody that binds to Ly6E is provided for use as a medicament. In other embodiments the antibody that binds to Ly6E binds to an epitope within amino acids 21-131 of SEQ ID NO:1. In another embodiment, such an antibody binds Ly6E with an affinity of ≤4 nM as measured by scatchard analysis. In another embodiment, such an antibody binds Ly6E with an affinity of ≤7 nM as measured by SPR. In yet another embodiment, such an antibody is used for treating a Ly6E-positive cancer. In some embodiments, such an antibody is used for inhibiting the proliferation of a Ly6E-positive cancer cell. In some embodiments, the Ly6E-positive cancer cell is a breast cancer cell, pancreatic cancer cell, colon cancer cell, colorectal cancer cell, melanoma cell, ovarian cancer cell, non-small cell lung cancer cell, or gastric cancer cell. In some embodiments, use of such an antibody as described herein is used in the manufacture of a medicament. In another embodiment, such use is for a medicament for the treatment of a Ly6E-positive cancer. In yet another embodiment, such use is for inhibiting the proliferation of a Ly6E-positive cancer cell. In some embodiments, the Ly6E-positive cancer cell is a breast cancer cell, pancreatic cancer cell, colon cancer cell, colorectal cancer cell, melanoma cell, ovarian cancer cell, non-small cell lung cancer cell, or gastric cancer cell.

BRIEF DESCRIPTION OF THE FIGURES

Figure 1:
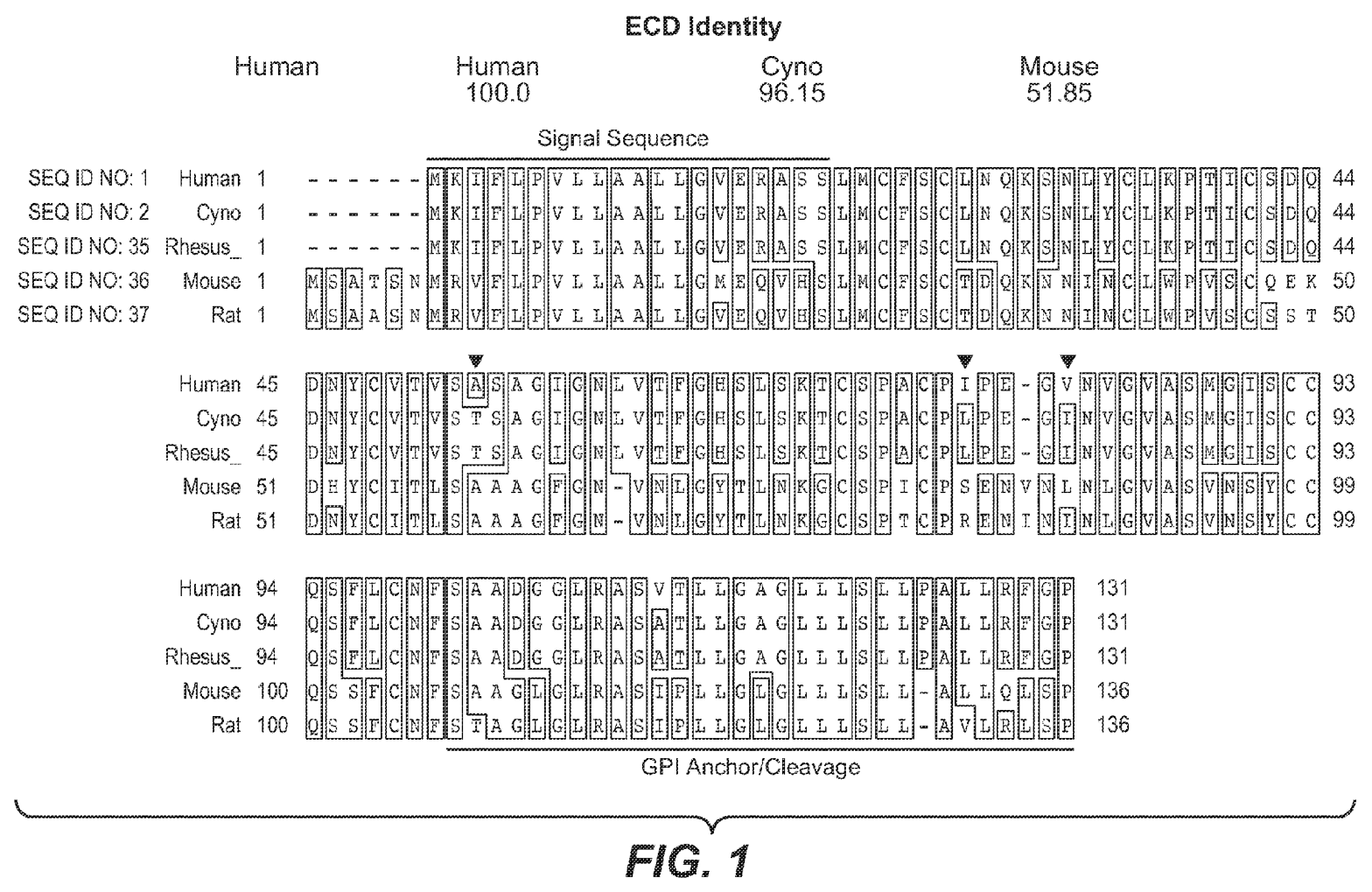

FIG. 1 shows a sequence alignment comparing the sequences of Ly6E orthologs from human (SEQ ID NO: 1), Cynomolgus monkey (SEQ ID NO: 2), Rhesus (SEQ ID NO: 35), mouse (SEQ ID NO: 36), and rat species (SEQ ID NO: 37). The percent identity at the amino acid level between these sequences in the extracellular domain (ECD) is shown to be ~96% between human and cynomolgus monkey Ly6E and ~52% between human and rat Ly6E.

FIG. 4 shows the light chain variable domain sequence alignment of a humanized anti-Ly6E antibody (hu9B12.v12) as compared to a chimeric anti-Ly6E antibody (xLy6E mu9B12) and a human kappa I consensus sequence (Kappa I consensus). Amino acid positions that differ from the human consensus frameworks are shaded in grey. Regions that were transferred to generate the CDR graft are boxed. Positions are numbered according to Kabat.

FIG. 5 shows the heavy chain variable domain sequence alignment of a humanized anti-Ly6E antibody (hu9B12.v12) as compared to a chimeric anti-Ly6E antibody (xLy6E mu9B12) and a human VH$_2$ consensus sequence (VH2 consensus). Amino acid positions that differ from the human consensus frameworks are shaded in grey. Regions that were transferred to generate the CDR graft are boxed. Positions are numbered according to Kabat.

FIG. 6 shows the heavy chain variable domain sequence alignment of a humanized anti-Ly6E antibody (hu9B12.v12) as compared to a chimeric anti-Ly6E antibody (xLy6E mu9B12) and a human VH$_3$ consensus sequence (VH3 consensus). Amino acid positions that differ from the human consensus frameworks are shaded in grey. Regions that were transferred to generate the CDR graft are boxed. Positions are numbered according to Kabat.

DETAILED DESCRIPTION OF EMBODIMENTS OF THE INVENTION

I. Definitions

Figure 2:
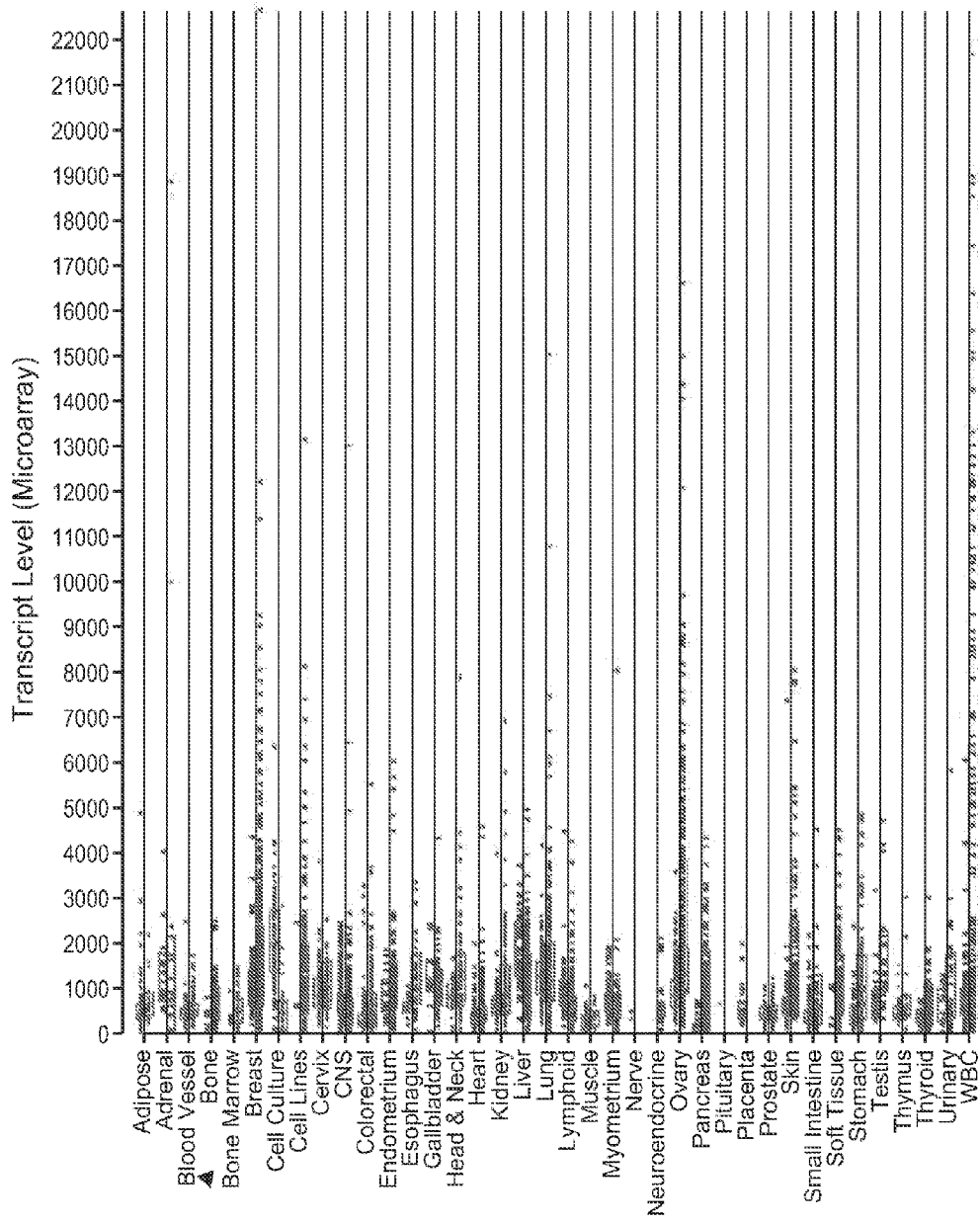
FIG. 2 shows a Genelogic profile of Ly6E mRNA expression as further described in Example 1. Measurements were carried out on the Affymetrix U133P chip and are expressed as scaled average differences in Ly6E expression in human tissues. Each dot represents a normal (green), tumor (red), or diseased non-tumor (blue) human tissue specimen. Rectangles encompass the 25 to 75 percentile range for each distribution. WBC=white blood cells. Over-expression of Ly6E is seen in breast, pancreatic, colorectal, lung, melanoma and ovarian cancers, among others.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-Ly6E antibody" and "an antibody that binds to Ly6E" refer to an antibody that is capable of binding Ly6E with sufficient affinity such that the antibody is useful as a diagnostic and/or therapeutic agent in targeting Ly6E. In one embodiment, the extent of binding of an anti-Ly6E antibody to an unrelated, non-Ly6E protein is less than about 10% of the binding of the antibody to Ly6E as measured, e.g., by a radioimmunoassay (RIA) or by scatchard analysis or by surface plasmon resonance, such as, for example, Biacore. In certain embodiments, an antibody that binds to Ly6E has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-Ly6E antibody binds to an epitope of Ly6E that is conserved among Ly6E from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

The term "antibody drug conjugate" (ADC) as used herein is equivalent to the term "immunoconjugate".

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include a cancer that over-expresses Ly6E, which may include, for example, breast cancer and/or metastatic breast cancer, including Her2 negative breast cancers and/or triple negative breast cancers, pancreatic cancer, colon cancer, colorectal cancer, melanoma, ovarian cancer, non-small cell lung cancer (either squamous and/or non-squamous), gastric cancer, squamous cell cancer, small-cell lung cancer, adenocarcinoma of the lung, squamous carcinoma of the lung, cancer of the peritoneum, hepatocellular cancer, gastrointestinal cancer, glioma, cervical cancer, liver cancer, bladder cancer, hepatoma, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The term "chimeric" antibody refers to an antibody in which a portion of the heavy and/or light chain is derived from a particular source or species, while the remainder of the heavy and/or light chain is derived from a different source or species.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "epitope" refers to the particular site on an antigen molecule to which an antibody binds.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent. An immunoconjugate is equivalent to the term "antibody drug conjugate" (ADC).

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-Ly6E antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "Ly6E," as used herein, refers to any native, mature Ly6E which results from processing of a Ly6E precursor protein in a cell. The term includes Ly6E from any vertebrate source, including mammals such as primates (e.g. humans and cynomolgus or rhesus monkeys) and rodents (e.g., mice and rats), unless otherwise indicated. The term also includes naturally occurring variants of Ly6E, e.g., splice variants or allelic variants. The amino acid sequence of an exemplary human Ly6E precursor protein, with signal sequence (amino acids 1-20=signal sequence) is shown in SEQ ID NO: 1. The amino acid sequence of an exemplary mature human Ly6E is shown in SEQ ID NO: 38. The sequence for amino acids 1-131 of an exemplary cynomolgous monkey Ly6E is shown in SEQ ID NO: 2. The amino acid sequence of an exemplary mature cynomologous Ly6E is shown in SEQ ID NO: 39. The amino acid sequence for an exemplary rat Ly6E precursor (with signal sequence, amino acids 1-26) and mature sequences are shown in SEQ ID NOs: 37 and 42, respectively. The amino acid sequences for exemplary mouse Ly6E precursor (with signal sequence, amino acids 1-26) and mature sequences are shown in SEQ ID NOs: 36 and 41, respectively.

The term "Ly6E-positive cancer" refers to a cancer comprising cells that express Ly6E on their surface. For the purposes of determining whether a cell expresses Ly6E on the surface, Ly6E mRNA expression is considered to correlate to Ly6E expression on the cell surface. In some embodiments, expression of Ly6E mRNA is determined by a method selected from in situ hybridization and RT-PCR (including quantitative RT-PCR). Alternatively, expression of Ly6E on the cell surface can be determined, for example, using antibodies to Ly6E in a method such as immunohistochemistry, FACS, etc. In some embodiments, a Ly6E-positive cancer means a breast cancer, metastatic breast cancer, including Her2 negative breast cancers and/or triple negative breast cancers, pancreatic cancer, colon cancer, colorectal cancer, melanoma, ovarian cancer, non-small cell lung cancer (either squamous and/or non-squamous), or gastric cancer, each of which that exhibits a high level of Ly6E expression.

The term "Ly6E-positive cell" refers to a cancer cell that expresses Ly6E on its surface.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

A "platinum complex" as used herein refers to anti-cancer chemotherapy drugs such as, for example, but not limited to, cisplatin, oxaliplatin, carboplatin, iproplatin, satraplatin, CI-973, AZ0473, DWA2114R, nedaplatin, and sprioplatin, which exert efficacy against tumors based on their ability to covalently bind to DNA.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007)). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

"Alkyl" is $C_1$-$C_{18}$ hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$).

The term "$C_1$-$C_8$ alkyl," as used herein refers to a straight chain or branched, saturated or unsaturated hydrocarbon having from 1 to 8 carbon atoms. Representative "$C_1$-$C_8$ alkyl" groups include, but are not limited to, -methyl, -ethyl, -n-propyl, -n-butyl, -n-pentyl, -n-hexyl, -n-heptyl, -n-octyl, -n-nonyl and -n-decyl; while branched $C_1$-$C_8$ alkyls include, but are not limited to, -isopropyl, -sec-butyl, -isobutyl, -tert-butyl, -isopentyl, 2-methylbutyl, unsaturated $C_1$-$C_8$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl, -3-methyl-1 butynyl. A $C_1$-$C_8$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —$SO_3$R', —S(O)$_2$R', —S(O)R', —OH, -halogen, —$N_3$, —$NH_2$, —NH(R'), —N(R')$_2$ and —CN; where each R' is independently selected from H, —$C_1$-$C_8$ alkyl and aryl.

The term "$C_1$-$C_{12}$ alkyl," as used herein refers to a straight chain or branched, saturated or unsaturated hydrocarbon having from 1 to 12 carbon atoms. A $C_1$-$C_{12}$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —$SO_3$R', —S(O)$_2$R', —S(O)R', —OH, -halogen, —$N_3$, —$NH_2$, —NH(R'), —N(R')$_2$ and —CN; where each R' is independently selected from H, —$C_1$-$C_8$ alkyl and aryl.

The term "$C_1$-$C_6$ alkyl," as used herein refers to a straight chain or branched, saturated or unsaturated hydrocarbon having from 1 to 6 carbon atoms. Representative "$C_1$-$C_6$ alkyl" groups include, but are not limited to, -methyl, -ethyl, -n-propyl, -n-butyl, -n-pentyl, -and n-hexyl; while branched $C_1$-$C_6$ alkyls include, but are not limited to, -isopropyl, -sec-butyl, -isobutyl, -tert-butyl, -isopentyl, and 2-methylbutyl; unsaturated $C_1$-$C_6$ alkyls include, but are not limited to, -vinyl, -allyl, -1-butenyl, -2-butenyl, and -isobutylenyl, -1-pentenyl, -2-pentenyl, -3-methyl-1-butenyl, 2-methyl-2-butenyl, -2,3-dimethyl-2-butenyl, 1-hexyl, 2-hexyl, and 3-hexyl. A $C_1$-$C_6$ alkyl group can be unsubstituted or substituted with one or more groups, as described above for $C_1$-$C_8$ alkyl group.

The term "$C_1$-$C_4$ alkyl," as used herein refers to a straight chain or branched, saturated or unsaturated hydrocarbon having from 1 to 4 carbon atoms. Representative "$C_1$-$C_4$ alkyl" groups include, but are not limited to, -methyl, -ethyl, -n-propyl, -n-butyl; while branched $C_1$-$C_4$ alkyls include, but are not limited to, -isopropyl, -sec-butyl, -isobutyl, -tert-butyl; unsaturated $C_1$-$C_4$ alkyls include, but are not limited to, -vinyl, -allyl, -1-butenyl, -2-butenyl, and -isobutylenyl. A $C_1$-$C_4$ alkyl group can be unsubstituted or substituted with one or more groups, as described above for $C_1$-$C_8$ alkyl group.

"Alkoxy" is an alkyl group singly bonded to an oxygen. Exemplary alkoxy groups include, but are not limited to, methoxy (—$OCH_3$) and ethoxy (—$OCH_2CH_3$). A "$C_1$-$C_5$ alkoxy" is an alkoxy group with 1 to 5 carbon atoms. Alkoxy groups may can be unsubstituted or substituted with one or more groups, as described above for alkyl groups.

"Alkenyl" is $C_2$-$C_{18}$ hydrocarbon containing normal, secondary, tertiary or cyclic carbon atoms with at least one site of unsaturation, i.e. a carbon-carbon, $sp^2$ double bond. Examples include, but are not limited to: ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$). A "$C_2$-$C_8$ alkenyl" is a hydrocarbon containing 2 to 8 normal, secondary, tertiary or cyclic carbon atoms with at least one site of unsaturation, i.e. a carbon-carbon, $sp^2$ double bond.

"Alkynyl" is $C_2$-$C_{18}$ hydrocarbon containing normal, secondary, tertiary or cyclic carbon atoms with at least one site of unsaturation, i.e. a carbon-carbon, sp triple bond. Examples include, but are not limited to: acetylenic (—C≡CH) and propargyl (—$CH_2$C≡CH). A "$C_2$-$C_8$ alkynyl" is a hydrocarbon containing 2 to 8 normal, secondary, tertiary or cyclic carbon atoms with at least one site of unsaturation, i.e. a carbon-carbon, sp triple bond.

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—$CH_2$—) 1,2-ethyl (—$CH_2CH_2$—), 1,3-propyl (—$CH_2CH_2CH_2$—), 1,4-butyl (—$CH_2CH_2CH_2CH_2$—), and the like.

A "$C_1$-$C_{10}$ alkylene" is a straight chain, saturated hydrocarbon group of the formula —$(CH_2)_{1-10}$—. Examples of a $C_1$-$C_{10}$ alkylene include methylene, ethylene, propylene, butylene, pentylene, hexylene, heptylene, ocytylene, nonylene and decalene.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene (—C≡C—), propargyl (—$CH_2$C≡C—), and 4-pentynyl (—$CH_2CH_2CH_2$C≡C—).

"Aryl" refers to a carbocyclic aromatic group. Examples of aryl groups include, but are not limited to, phenyl, naphthyl and anthracenyl. A carbocyclic aromatic group or a heterocyclic aromatic group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —S(O)$_2$R', —S(O)R', —OH, -halogen, —$N_3$, —$NH_2$, —NH(R'), —N(R')$_2$ and —CN; wherein each R' is independently selected from H, —$C_1$-$C_8$ alkyl and aryl.

A "$C_5$-$C_{20}$ aryl" is an aryl group with 5 to 20 carbon atoms in the carbocyclic aromatic rings. Examples of $C_5$-$C_{20}$ aryl groups include, but are not limited to, phenyl, naphthyl and anthracenyl. A $C_5$-$C_{20}$ aryl group can be substituted or unsubstituted as described above for aryl groups. A "$C_5$-$C_{14}$ aryl" is an aryl group with 5 to 14 carbon atoms in the carbocyclic aromatic rings. Examples of $C_5$-$C_{14}$ aryl groups include, but are not limited to, phenyl, naphthyl and anthracenyl. A $C_5$-$C_{14}$ aryl group can be substituted or unsubstituted as described above for aryl groups.

An "arylene" is an aryl group which has two covalent bonds and can be in the ortho, meta, or para configurations as shown in the following structures:

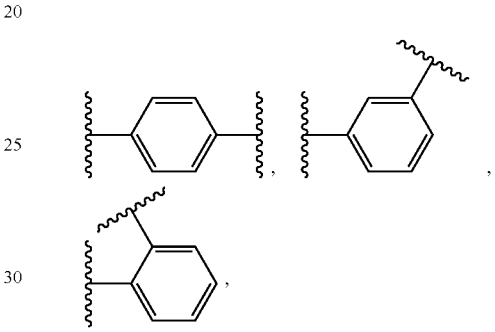

in which the phenyl group can be unsubstituted or substituted with up to four groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —S(O)$_2$R', —S(O)R', —OH, -halogen, —$N_3$, —$NH_2$, —NH(R'), —N(R')$_2$ and —CN; wherein each R' is independently selected from H, —$C_1$-$C_8$ alkyl and aryl.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms.

"Heteroarylalkyl" refers to an acyclic alkyl radical in which one of the hydrogen atoms bonded to a carbon atom, typically a terminal or $sp^3$ carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g. the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo [4,5], [5,5], [5,6], or [6,6] system.

"Substituted alkyl," "substituted aryl," and "substituted arylalkyl" mean alkyl, aryl, and arylalkyl respectively, in which one or more hydrogen atoms are each independently replaced with a substituent. Typical substituents include, but are not limited to, —X, —R, —O⁻, —OR, —SR, —S⁻, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NR$_2$, —SO$_3^-$, —SO$_3$H, —S(=O)$_2$R, —OS(=O)$_2$OR, —S(=O)$_2$NR, —S(=O)R, —OP(=O)(OR)$_2$, —P(=O)(OR)$_2$, —PO$^-_3$, —PO$_3$H$_2$, —C(=O)R, —C(=O)X, —C(=S)R, —CO$_2$R, —CO$_2^-$, —C(=S)OR, —C(=O)SR, —C(=S)SR, —C(=O)NR$_2$, —C(=S)NR$_2$, —C(=NR)NR$_2$, where each X is independently a halogen: F, Cl, Br, or I; and each R is independently —H, C$_2$-C$_{18}$ alkyl, C$_6$-C$_{20}$ aryl, C$_3$-C$_{14}$ heterocycle, protecting group or prodrug moiety. Alkylene, alkenylene, and alkynylene groups as described above may also be similarly substituted.

"Heteroaryl" and "heterocycle" refer to a ring system in which one or more ring atoms is a heteroatom, e.g. nitrogen, oxygen, and sulfur. The heterocycle radical comprises 3 to 20 carbon atoms and 1 to 3 heteroatoms selected from N, O, P, and S. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system.

Exemplary heterocycles are described, e.g., in Paquette, Leo A., "Principles of Modern Heterocyclic Chemistry" (W.A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

A "C$_3$-C$_8$ heterocycle" refers to an aromatic or non-aromatic C$_3$-C$_8$ carbocycle in which one to four of the ring carbon atoms are independently replaced with a heteroatom from the group consisting of O, S and N. Representative examples of a C$_3$-C$_8$ heterocycle include, but are not limited to, benzofuranyl, benzothiophene, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A C$_3$-C$_8$ heterocycle can be unsubstituted or substituted with up to seven groups including, but not limited to, —C$_1$-C$_8$ alkyl, —O—(C$_1$-C$_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —C$_1$-C$_8$ alkyl and aryl.

"C$_3$-C$_8$ heterocyclo" refers to a C$_3$-C$_8$ heterocycle group defined above wherein one of the heterocycle group's hydrogen atoms is replaced with a bond. A C$_3$-C$_8$ heterocyclo can be unsubstituted or substituted with up to six groups including, but not limited to, —C$_1$-C$_8$ alkyl, —O—(C$_1$-C$_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —C$_1$-C$_8$ alkyl and aryl.

A "C$_3$-C$_{20}$ heterocycle" refers to an aromatic or non-aromatic C$_3$-C$_8$ carbocycle in which one to four of the ring carbon atoms are independently replaced with a heteroatom from the group consisting of O, S and N. A C$_3$-C$_{20}$ heterocycle can be unsubstituted or substituted with up to seven groups including, but not limited to, —C$_1$-C$_8$ alkyl, —O— (C$_1$-C$_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH (R'), —N(R')$_2$ and —CN; wherein each R' is independently selected from H, —C$_1$-C$_8$ alkyl and aryl.

"C$_3$-C$_{20}$ heterocyclo" refers to a C$_3$-C$_{20}$ heterocycle group defined above wherein one of the heterocycle group's hydrogen atoms is replaced with a bond.

"Carbocycle" means a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl.

A "$C_3$-$C_8$ carbocycle" is a 3-, 4-, 5-, 6-, 7- or 8-membered saturated or unsaturated non-aromatic carbocyclic ring. Representative $C_3$-$C_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. A $C_3$-$C_8$ carbocycle group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; where each R' is independently selected from H, —$C_1$-$C_8$ alkyl and aryl.

A "$C_3$-$C_8$ carbocyclo" refers to a $C_3$-$C_8$ carbocycle group defined above wherein one of the carbocycle groups' hydrogen atoms is replaced with a bond.

"Linker" refers to a chemical moiety comprising a covalent bond or a chain of atoms that covalently attaches an antibody to a drug moiety. In various embodiments, linkers include a divalent radical such as an alkyldiyl, an aryldiyl, a heteroaryldiyl, moieties such as: —(CR$_2$)$_n$O(CR$_2$)—, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide. In various embodiments, linkers can comprise one or more amino acid residues, such as valine, phenylalanine, lysine, and homolysine.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

"Leaving group" refers to a functional group that can be substituted by another functional group. Certain leaving groups are well known in the art, and examples include, but are not limited to, a halide (e.g., chloride, bromide, iodide), methanesulfonyl (mesyl), p-toluenesulfonyl (tosyl), trifluoromethylsulfonyl (triflate), and trifluoromethylsulfonate.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include, but are not limited to, acetyl, trifluoroacetyl, t-butoxycarbonyl (BOC), benzyloxycarbonyl (CBZ) and 9-fluorenylmethylenoxycarbonyl (Fmoc). For a general description of protecting groups and their use, see T. W. Greene, Protective Groups in Organic Synthesis, John Wiley & Sons, New York, 1991, or a later edition.

II. Compositions and Methods

In one aspect, the invention is based, in part, on antibodies that bind to LY6E and immunoconjugates comprising such antibodies. Antibodies and immunoconjugates of the invention are useful, e.g., for the diagnosis or treatment of LY6E-positive cancers.

A. Exemplary Anti-Ly6E Antibodies

In some embodiments, the invention provides isolated antibodies that bind to LY6E. In certain embodiments, an anti-LY6E antibody has at least one or more of the following characteristics, in any combination:
(a) binds to an epitope within amino acids 21-131 of SEQ ID NO: 1; and
(b) binds Ly6E with an affinity of ≤7 nM, or ≤6 nM, or ≤5 nM, or ≤4 nM, or ≤3 nM, or ≤2 nM, or ≤1 nM, and optionally ≥0.0001 nM, or ≥0.001 nM, or ≥0.01 nM as measured by either SPR or scatchard analysis.

Figure 4:
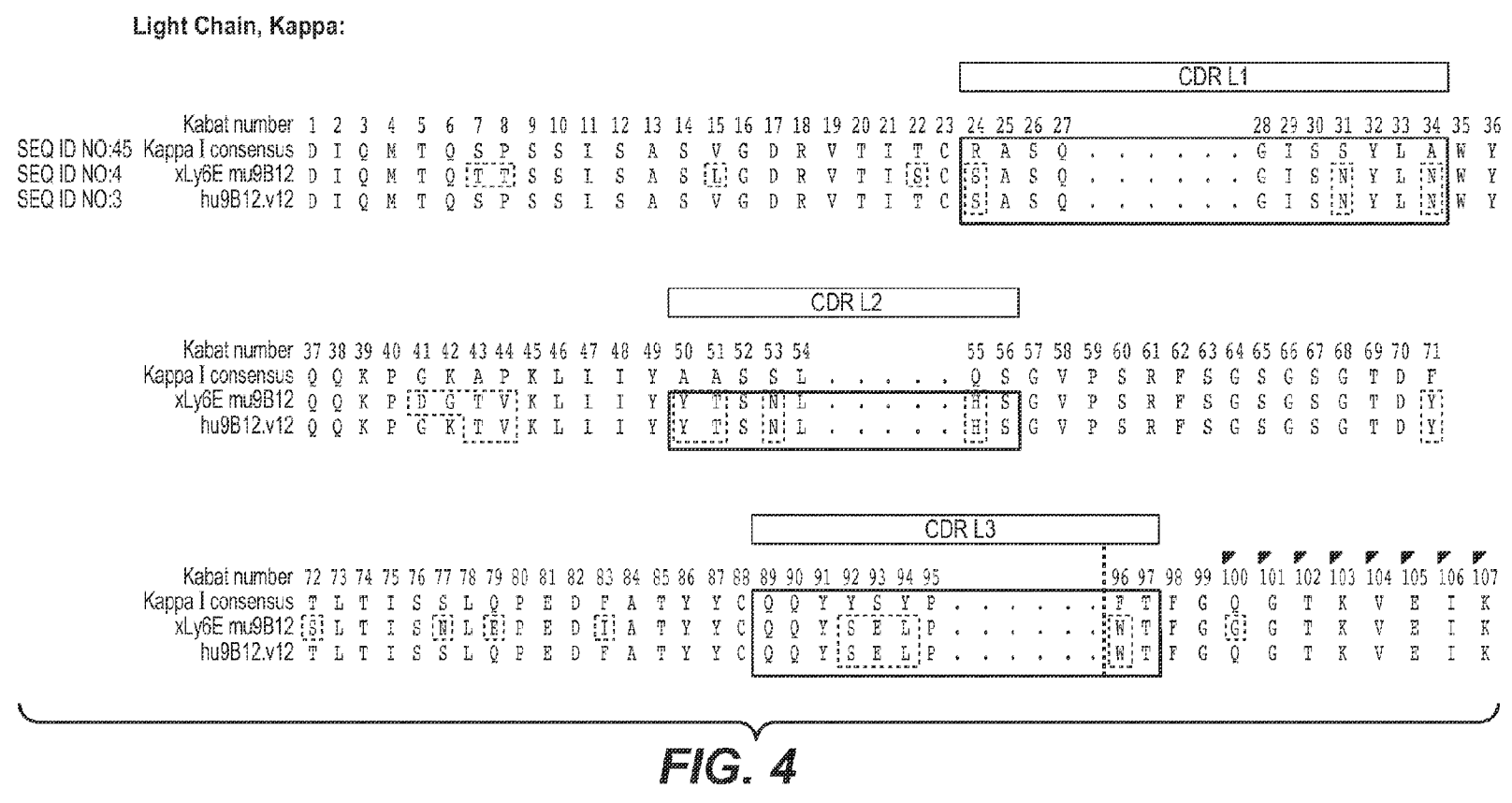
Figure 5:
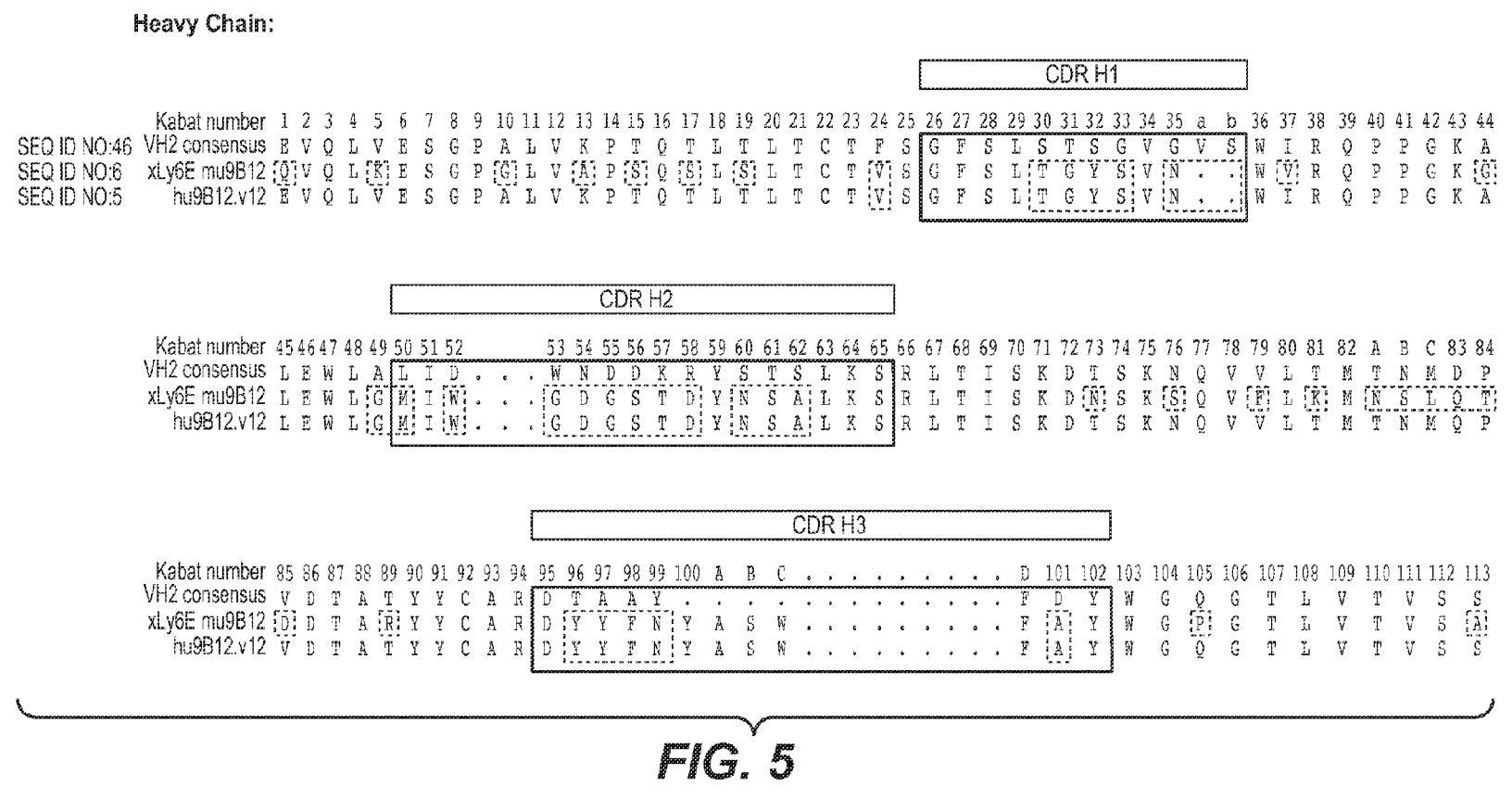

A nonlimiting exemplary antibody of the invention is the murine 9B12 as shown in FIGS. 4-6 and humanized variants thereof, such as, for example, hu9B12.v12, as shown in FIGS. 4-6. In some embodiments, Ly6E is human Ly6E. In some embodiments, Ly6E is selected from human, cynomolgus monkey, rhesus monkey, mouse or rat Ly6E.

In some embodiments, an anti-Ly6E antibody binds to an epitope within amino acids 21-131 of SEQ ID NO: 1. In some such embodiments, the anti-Ly6E antibody binds Ly6E with an affinity of ≤7 nM, or ≤6 nM, or ≤5 nM, or ≤4 nM, or ≤3 nM, or ≤2 nM, or ≤1 nM, and optionally ≥0.0001 nM, or ≥0.001 nM, or ≥0.01 nM as measured by either SPR or scatchard analysis. A nonlimiting exemplary antibody of the invention is the murine 9B12 as shown in FIGS. 4-6 and humanized variants thereof, such as, for example, hu9B12.v12, as shown in FIGS. 4-6. In some embodiments, Ly6E is human Ly6E. In some embodiments, Ly6E is human Ly6E or cynomolgus monkey Ly6E.

In one aspect, the invention provides an anti-Ly6E antibody comprising at least one, two, three, four, five, or six HVRs selected from (a) HVR-H1 comprising the amino acid sequence of SEQ ID NO: 10; (b) HVR-H2 comprising the amino acid sequence of SEQ ID NO: 11; (c) HVR-H3 comprising the amino acid sequence of SEQ ID NO:12; (d) HVR-L1 comprising the amino acid sequence of SEQ ID NO:7; (e) HVR-L2 comprising the amino acid sequence of SEQ ID NO:8; and (f) HVR-L3 comprising the amino acid sequence of SEQ ID NO:9.

In one aspect, the invention provides an antibody comprising at least one, at least two, or all three VH HVR sequences selected from (a) HVR-H1 comprising the amino acid sequence of SEQ ID NO: 10; (b) HVR-H2 comprising the amino acid sequence of SEQ ID NO: 11; and (c) HVR-H3 comprising the amino acid sequence of SEQ ID NO:12. In one embodiment, the antibody comprises HVR-H3 comprising the amino acid sequence of SEQ ID NO:12. In another embodiment, the antibody comprises HVR-H3 comprising the amino acid sequence of SEQ ID NO:12 and HVR-L3 comprising the amino acid sequence of SEQ ID NO:9. In a further embodiment, the antibody comprises HVR-H3 comprising the amino acid sequence of SEQ ID NO:12, HVR-L3 comprising the amino acid sequence of SEQ ID NO:9, and HVR-H2 comprising the amino acid sequence of SEQ ID NO: 11. In a further embodiment, the antibody comprises (a) HVR-H1 comprising the amino acid sequence of SEQ ID NO: 10; (b) HVR-H2 comprising the amino acid sequence of SEQ ID NO: 11; and (c) HVR-H3 comprising the amino acid sequence of SEQ ID NO:12.

In another aspect, the invention provides an antibody comprising at least one, at least two, or all three VL HVR sequences selected from (a) HVR-L1 comprising the amino acid sequence of SEQ ID NO:7; (b) HVR-L2 comprising the amino acid sequence of SEQ ID NO:8; and (c) HVR-L3 comprising the amino acid sequence of SEQ ID NO:9. In one embodiment, the antibody comprises (a) HVR-L1 comprising the amino acid sequence of SEQ ID NO:7; (b) HVR-L2 comprising the amino acid sequence of SEQ ID NO:8; and (c) HVR-L3 comprising the amino acid sequence of SEQ ID NO:9.

In another aspect, an antibody of the invention comprises (a) a VH domain comprising at least one, at least two, or all three VH HVR sequences selected from (i) HVR-H1 comprising the amino acid sequence of SEQ ID NO: 10, (ii) HVR-H2 comprising the amino acid sequence of SEQ ID NO: 11, and (iii) HVR-H3 comprising an amino acid sequence selected from SEQ ID NO:12; and (b) a VL domain comprising at least one, at least two, or all three VL HVR sequences selected from (i) HVR-L1 comprising the amino acid sequence of SEQ ID NO:7, (ii) HVR-L2 comprising the amino acid sequence of SEQ ID NO:8, and (c) HVR-L3 comprising the amino acid sequence of SEQ ID NO:9.

In another aspect, the invention provides an antibody comprising (a) HVR-H1 comprising the amino acid sequence of SEQ ID NO: 10; (b) HVR-H2 comprising the amino acid sequence of SEQ ID NO:11; (c) HVR-H3 comprising the amino acid sequence of SEQ ID NO:12; (d) HVR-L1 comprising the amino acid sequence of SEQ ID NO:7; (e) HVR-L2 comprising the amino acid sequence of SEQ ID NO:8; and (f) HVR-L3 comprising an amino acid sequence selected from SEQ ID NO:9.

In certain embodiments, any one or more amino acids of an anti-Ly6E antibody as provided above are substituted at the following HVR positions:

In any of the above embodiments, an anti-Ly6E antibody is humanized. In one embodiment, an anti-Ly6E antibody comprises HVRs as in any of the above embodiments, and further comprises an acceptor human framework, e.g. a human immunoglobulin framework or a human consensus framework. In another embodiment, an anti-Ly6E antibody comprises HVRs as in any of the above embodiments, and it further comprises a light chain variable domain framework FR2 sequence of SEQ ID NO:20 or light chain variable domain framework FR3 of SEQ ID NO:21 or heavy chain variable domain framework FR1 or SEQ ID NO:23, or heavy chain variable domain framework FR2 of SEQ ID NO:24.

In another aspect, an anti-Ly6E antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:5. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-Ly6E antibody comprising that sequence retains the ability to bind to Ly6E. In certain embodiments, a total of 1 to 10 amino acids have been substituted, inserted and/or deleted in SEQ ID NO:5. In certain embodiments, substitutions, insertions, or deletions occur in regions outside the HVRs (i.e., in the FRs). Optionally, the anti-Ly6E antibody comprises the VH sequence in SEQ ID NO:5, including post-translational modifications of that sequence. In a particular embodiment, the VH comprises one, two or three HVRs selected from: (a) HVR-H1 comprising the amino acid sequence of SEQ ID NO: 10, (b) HVR-H2 comprising the amino acid sequence of SEQ ID NO: 11, and (c) HVR-H3 comprising the amino acid sequence of SEQ ID NO:12.

In another aspect, an anti-Ly6E antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:3. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-Ly6E antibody comprising that sequence retains the ability to bind to Ly6E. In certain embodiments, a total of 1 to 10 amino acids have been substituted, inserted and/or deleted in SEQ ID NO:3. In certain embodiments, the substitutions, insertions, or deletions occur in regions outside the HVRs (i.e., in the FRs). Optionally, the anti-Ly6E antibody comprises the VL sequence in SEQ ID NO:3, including post-translational modifications of that sequence. In a particular embodiment, the VL comprises one, two or three HVRs selected from (a) HVR-L1 comprising the amino acid sequence of SEQ ID NO:7; (b) HVR-L2 comprising the amino acid sequence of SEQ ID NO:8; and (c) HVR-L3 comprising the amino acid sequence of SEQ ID NO:9.

In another aspect, an anti-Ly6E antibody is provided, wherein the antibody comprises a VH as in any of the embodiments provided above, and a VL as in any of the embodiments provided above. In one embodiment, the antibody comprises the VH and VL sequences in SEQ ID NO:5 and SEQ ID NO:3, respectively, including post-translational modifications of those sequences.

In a further aspect, the invention provides an antibody that binds to the same epitope as an anti-Ly6E antibody provided herein. For example, in certain embodiments, an antibody is provided that binds to the same epitope as an anti-Ly6E antibody comprising a VH sequence of SEQ ID NO:5 and a VL sequence of SEQ ID NO:3. In certain embodiments, an antibody is provided that binds to an epitope within a fragment of Ly6E consisting of amino acids 21-131 of SEQ ID NO:1.

In a further aspect of the invention, an anti-Ly6E antibody according to any of the above embodiments is a monoclonal antibody, including a chimeric, humanized or human antibody. In one embodiment, an anti-Ly6E antibody is an antibody fragment, e.g., a Fv, Fab, Fab', scFv, diabody, or F(ab')$_2$ fragment. In another embodiment, the antibody is a full length antibody, e.g., an intact IgG1 antibody or other antibody class or isotype as defined herein.

In a further aspect, an anti-Ly6E antibody according to any of the above embodiments may incorporate any of the features, singly or in combination, as described in Sections 1-7 below.

Assays

To determine whether an anti-LY6E antibody "binds to an epitope within amino acids 21-131 of SEQ ID NO: 1 Ly6E polypeptides with N- and C-terminal deletions are expressed in 293 cells and binding of the antibody to the truncated polypeptides is tested by FACS, wherein a substantial reduction (≥70% reduction) or elimination of binding of the antibody to a truncated polypeptide relative to binding to full-length Ly6E expressed in 293 cells indicates that the antibody does not bind to that truncated polypeptide.

Whether an anti-Ly6E antibody "binds with an affinity of ≤6 nM, or ≤5 nM, or ≤4 nM, or ≤3 nM, or ≤2 nM, or ≤1 nM," is determined according to a scatchard analysis as described herein in Example 4. Alternatively, an anti-Ly6E antibody affinity can be determined according to, for example, a BIAcore assay. Specifically, Kd is measured using surface plasmon resonance assays using a BIACORE®-3000 (BIAcore, Inc., Piscataway, N.J.). BIAcore™ research grade CM5 chips are activated with 1-ethyl-3-(3-dimethylaminopropyl) carbodiimide (EDC) and N-hydroxysuccinimide (NHS) reagents according to the supplier's instructions. Goat anti-human Fc IgGs are coupled to the chips to achieve approximately 10,000 response units (RU) in each flow cell. Unreacted coupling groups are blocked with 1M ethanolamine. For kinetics measurements, anti-Ly6E antibodies are captured to achieve approximately 300 RU. Two-fold serial dilutions of human Ly6E (for example, amino acids 21-131 fused to His-Fc expressed in a baculovirus system, or amino acids 21-131 fused to Fc expressed from CHO cells; 125 nM to 0.49 nM) are injected in HBS-P buffer (0.01M HEPES pH 7.4, 0.15M NaCl, 0.005% surfactant P20) at 25° C. with a flow rate of 30 μl/min. Association rates ($k_{on}$) and dissociation rates ($k_{off}$) are calculated using a 1:1 Langmuir binding model (BIAcore™ Evaluation Software version 3.2). The equilibrium dissociation constant (Kd) is calculated as the ratio $k_{off}/k_{on}$. If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco® spectrophotometer (ThermoSpectronic) with a stirred cuvette.

In any of the above embodiments, an anti-Ly6E antibody is humanized. In one embodiment, an anti-Ly6E antibody comprises HVRs as in any of the above embodiments, and further comprises a human acceptor framework, e.g. a human immunoglobulin framework or a human consensus framework. In certain embodiments, the human acceptor framework is the human VL kappa IV consensus (VL$_{KIV}$) framework and/or the VH framework VH$_1$.

In a further aspect of the invention, an anti-Ly6E antibody according to any of the above embodiments is a monoclonal antibody, including a chimeric, humanized or human antibody. In one embodiment, an anti-Ly6E antibody is an antibody fragment, e.g., a Fv, Fab, Fab', scFv, diabody, or F(ab')$_2$ fragment. In another embodiment, the antibody is a substantially full length antibody, e.g., an IgG1 antibody or other antibody class or isotype as defined herein.

In a further aspect, an anti-Ly6E antibody according to any of the above embodiments may incorporate any of the features, singly or in combination, as described in Sections 1-7 below.

In a further aspect of the invention, an anti-Ly6E antibody according to any of the above embodiments is a monoclonal antibody, including a human antibody. In one embodiment, an anti-Ly6E antibody is an antibody fragment, e.g., a Fv, Fab, Fab', scFv, diabody, or F(ab')$_2$ fragment. In another embodiment, the antibody is a substantially full length antibody, e.g., an IgG2a antibody or other antibody class or isotype as defined herein.

In a further aspect, an anti-Ly6E antibody according to any of the above embodiments may incorporate any of the features, singly or in combination, as described in Sections 1-7 below.

1. Antibody Affinity

In certain embodiments, an antibody provided herein has a dissociation constant (Kd) of ≤1 μM, ≤100 nM, ≤10 nM, ≤1 nM, ≤0.1 nM, ≤0.01 nM, or ≤0.001 nM, and optionally is ≥$10^{-13}$ M. (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using scatchard analysis, as described in Example 4. According to another embodiment, Kd is measured using surface plasmon resonance assays using a BIACORE®-2000 or a BIA-CORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds 106 $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthiin, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications*, pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue*, 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for LY6E and the other is for any other antigen. In certain embodiments, one of the binding specificities is for LY6E and the other is for CD3. See, e.g., U.S. Pat. No. 5,821,337. In certain embodiments, bispecific antibodies may bind to two different epitopes of Ly6E. Bispecific antibodies may also be used to localize cytotoxic agents to cells which express Ly6E. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to Ly6E as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis.

Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the $CH_2$ domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-LY6E antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-LY6E antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-LY6E antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in *Mather, Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Anti-LY6E antibodies provided herein may be identified, screened for, or characterized for their physical/chemical properties and/or biological activities by various assays known in the art.

In one aspect, an antibody of the invention is tested for its antigen binding activity, e.g., by known methods such as ELISA, BIACore®, FACS, or Western blot.

In another aspect, competition assays may be used to identify an antibody that competes with any of the antibodies described herein for binding to LY6E. In certain embodiments, such a competing antibody binds to the same epitope (e.g., a linear or a conformational epitope) that is bound by an antibody described herein. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized LY6E is incubated in a solution comprising a first labeled antibody that binds to LY6E (e.g., any of the antibodies described herein) and a second unlabeled antibody that is being tested for its ability to compete with the first antibody for binding to LY6E. The second antibody may be present in a hybridoma supernatant. As a control, immobilized LY6E is incubated in a solution comprising the first labeled antibody but not the second unlabeled antibody. After incubation under conditions permissive for binding of the first antibody to LY6E, excess unbound antibody is removed, and the amount of label associated with immobilized LY6E is measured. If the amount of label associated with immobilized LY6E is substantially reduced in the test sample relative to the control sample, then that indicates that the second antibody is competing with the first antibody for binding to LY6E. See Harlow and Lane (1988) *Antibodies: A Laboratory Manual* ch. 14 (Cold Spring Harbor Laboratory, Cold Spring Harbor, N.Y.).

D. Immunoconjugates

The invention also provides immunoconjugates comprising an anti-LY6E antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes (i.e., a radioconjugate).

Immunoconjugates allow for the targeted delivery of a drug moiety to a tumor, and, in some embodiments intracellular accumulation therein, where systemic administration of unconjugated drugs may result in unacceptable levels of toxicity to normal cells (Polakis P. (2005) *Current Opinion in Pharmacology* 5:382-387).

Antibody-drug conjugates (ADC) are targeted chemotherapeutic molecules which combine properties of both antibodies and cytotoxic drugs by targeting potent cytotoxic drugs to antigen-expressing tumor cells (Teicher, B. A. (2009) *Current Cancer Drug Targets* 9:982-1004), thereby enhancing the therapeutic index by maximizing efficacy and minimizing off-target toxicity (Carter, P. J. and Senter P. D. (2008) *The Cancer Jour.* 14(3):154-169; Chari, R. V. (2008) *Acc. Chem. Res.* 41:98-107.

The ADC compounds of the invention include those with anticancer activity. In some embodiments, the ADC compounds include an antibody conjugated, i.e. covalently attached, to the drug moiety. In some embodiments, the antibody is covalently attached to the drug moiety through a linker. The antibody-drug conjugates (ADC) of the invention selectively deliver an effective dose of a drug to tumor tissue whereby greater selectivity, i.e. a lower efficacious dose, may be achieved while increasing the therapeutic index ("therapeutic window").

The drug moiety (D) of the antibody-drug conjugates (ADC) may include any compound, moiety or group that has a cytotoxic or cytostatic effect. Drug moieties may impart their cytotoxic and cytostatic effects by mechanisms including but not limited to tubulin binding, DNA binding or intercalation, and inhibition of RNA polymerase, protein synthesis, and/or topoisomerase. Exemplary drug moieties include, but are not limited to, a maytansinoid, dolastatin, auristatin, calicheamicin, pyrrolobenzodiazepine (PBD), nemorubicin and its derivatives, PNU-159682, anthracycline, duocarmycin, vinca alkaloid, taxane, trichothecene, CC1065, camptothecin, elinafide, and stereoisomers, isosteres, analogs, and derivatives thereof that have cytotoxic activity. Nonlimiting examples of such immunoconjugates are discussed in further detail below.

1. Exemplary Antibody-Drug Conjugates

An exemplary embodiment of an antibody-drug conjugate (ADC) compound comprises an antibody (Ab) which targets a tumor cell, a drug moiety (D), and a linker moiety (L) that attaches Ab to D. In some embodiments, the antibody is attached to the linker moiety (L) through one or more amino acid residues, such as lysine and/or cysteine.

An exemplary ADC has Formula I:

Formula I where p is 1 to about 20. In some embodiments, the number of drug moieties that can be conjugated to an antibody is limited by the number of free cysteine residues. In some embodiments, free cysteine residues are introduced into the antibody amino acid sequence by the methods described herein. Exemplary ADC of Formula I include, but are not limited to, antibodies that have 1, 2, 3, or 4 engineered cysteine amino acids (Lyon, R. et al (2012) *Methods in Enzym.* 502:123-138). In some embodiments, one or more free cysteine residues are already present in an antibody, without the use of engineering, in which case the existing free cysteine residues may be used to conjugate the antibody to a drug. In some embodiments, an antibody is exposed to reducing conditions prior to conjugation of the antibody in order to generate one or more free cysteine residues.

a) Exemplary Linkers

A "Linker" (L) is a bifunctional or multifunctional moiety that can be used to link one or more drug moieties (D) to an antibody (Ab) to form an antibody-drug conjugate (ADC) of Formula I. In some embodiments, antibody-drug conjugates (ADC) can be prepared using a Linker having reactive functionalities for covalently attaching to the drug and to the antibody. For example, in some embodiments, a cysteine thiol of an antibody (Ab) can form a bond with a reactive functional group of a linker or a drug-linker intermediate to make an ADC.

In one aspect, a linker has a functionality that is capable of reacting with a free cysteine present on an antibody to form a covalent bond. Nonlimiting exemplary such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al (2004), *Bioconjugate Chemistry* 15(4):765-773, and the Examples herein.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary such reactive functionalities include, but are not limited to, hydrazide, oxime, amino, hydrazine, thiosemicarbazone, hydrazine carboxylate, and arylhydrazide.

A linker may comprise one or more linker components. Exemplary linker components include 6-maleimidocaproyl ("MC"), maleimidopropanoyl ("MP"), valine-citrulline ("val-cit" or "vc"), alanine-phenylalanine ("ala-phe"), p-aminobenzyloxycarbonyl (a "PAB"), N-Succinimidyl 4-(2-pyridylthio) pentanoate ("SPP"), and 4-(N-maleimidomethyl) cyclohexane-1 carboxylate ("MCC"). Various linker components are known in the art, some of which are described below.

A linker may be a "cleavable linker," facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., Cancer Research 52:127-131 (1992); U.S. Pat. No. 5,208,020).

In certain embodiments, a linker has the following Formula II:

-A$_a$-W$_w$-Y$_y$-      Formula II wherein A is a "stretcher unit", and a is an integer from 0 to 1; W is an "amino acid unit", and w is an integer from 0 to 12; Y is a "spacer unit", and y is 0, 1, or 2; and Ab, D, and p are defined as above for Formula I. Exemplary embodiments of such linkers are described in U.S. Pat. No. 7,498,298, which is expressly incorporated herein by reference.

In some embodiments, a linker component comprises a "stretcher unit" that links an antibody to another linker component or to a drug moiety. Nonlimiting exemplary stretcher units are shown below (wherein the wavy line indicates sites of covalent attachment to an antibody, drug, or additional linker components):

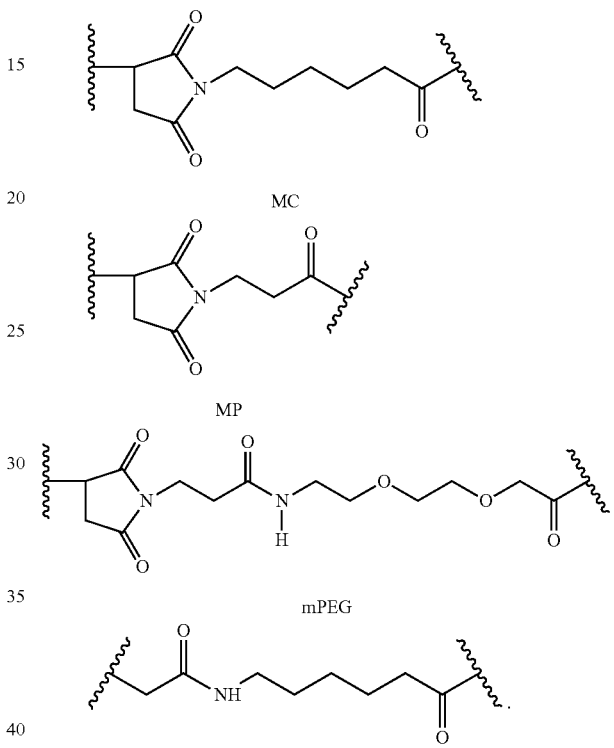

In some embodiments, a linker component comprises an "amino acid unit". In some such embodiments, the amino acid unit allows for cleavage of the linker by a protease, thereby facilitating release of the drug from the immunoconjugate upon exposure to intracellular proteases, such as lysosomal enzymes (Doronina et al. (2003) *Nat. Biotechnol.* 21:778-784). Exemplary amino acid units include, but are not limited to, dipeptides, tripeptides, tetrapeptides, and pentapeptides. Exemplary dipeptides include, but are not limited to, valine-citrulline (vc or val-cit), alanine-phenylalanine (af or ala-phe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit) and glycine-glycine-glycine (gly-gly-gly). An amino acid unit may comprise amino acid residues that occur naturally and/or minor amino acids and/or non-naturally occurring amino acid analogs, such as citrulline. Amino acid units can be designed and optimized for enzymatic cleavage by a particular enzyme, for example, a tumor-associated protease, cathepsin B, C and D, or a plasmin protease.

In some embodiments, a linker component comprises a "spacer" unit that links the antibody to a drug moiety, either directly or through a stretcher unit and/or an amino acid unit.

A spacer unit may be "self-immolative" or a "non-self-immolative." A "non-self-immolative" spacer unit is one in which part or all of the spacer unit remains bound to the drug moiety upon cleavage of the ADC. Examples of non-self-immolative spacer units include, but are not limited to, a glycine spacer unit and a glycine-glycine spacer unit. In some embodiments, enzymatic cleavage of an ADC containing a glycine-glycine spacer unit by a tumor-cell associated protease results in release of a glycine-glycine-drug moiety from the remainder of the ADC. In some such embodiments, the glycine-glycine-drug moiety is subjected to a hydrolysis step in the tumor cell, thus cleaving the glycine-glycine spacer unit from the drug moiety.

A "self-immolative" spacer unit allows for release of the drug moiety. In certain embodiments, a spacer unit of a linker comprises a p-aminobenzyl unit. In some such embodiments, a p-aminobenzyl alcohol is attached to an amino acid unit via an amide bond, and a carbamate, methylcarbamate, or carbonate is made between the benzyl alcohol and the drug (Hamann et al. (2005) Expert Opin. Ther. Patents (2005) 15:1087-1103). In some embodiments, the spacer unit is p-aminobenzyloxycarbonyl (PAB). In some embodiments, an ADC comprising a self-immolative linker has the structure:

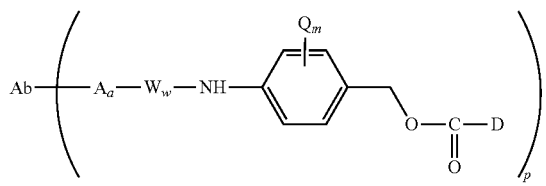

wherein Q is —$C_1$-$C_8$ alkyl, —O—($C_1$-$C_8$ alkyl), -halogen, -nitro, or -cyano; m is an integer ranging from 0 to 4; and p ranges from 1 to about 20. In some embodiments, p ranges from 1 to 10, 1 to 7, 1 to 5, or 1 to 4.

Other examples of self-immolative spacers include, but are not limited to, aromatic compounds that are electronically similar to the PAB group, such as 2-aminoimidazol-5-methanol derivatives (U.S. Pat. No. 7,375,078; Hay et al. (1999) Bioorg. Med. Chem. Lett. 9:2237) and ortho- or para-aminobenzylacetals. In some embodiments, spacers can be used that undergo cyclization upon amide bond hydrolysis, such as substituted and unsubstituted 4-aminobutyric acid amides (Rodrigues et al (1995) Chemistry Biology 2:223), appropriately substituted bicyclo[2.2.1] and bicyclo[2.2.2] ring systems (Storm et al (1972) J. Amer. Chem. Soc. 94:5815) and 2-aminophenylpropionic acid amides (Amsberry, et al (1990) J. Org. Chem. 55:5867). Linkage of a drug to the α-carbon of a glycine residue is another example of a self-immolative spacer that may be useful in ADC (Kingsbury et al (1984) J. Med. Chem. 27:1447).

In some embodiments, linker L may be a dendritic type linker for covalent attachment of more than one drug moiety to an antibody through a branching, multifunctional linker moiety (Sun et al (2002) Bioorganic & Medicinal Chemistry Letters 12:2213-2215; Sun et al (2003) Bioorganic & Medicinal Chemistry 11:1761-1768). Dendritic linkers can increase the molar ratio of drug to antibody, i.e. loading, which is related to the potency of the ADC. Thus, where an antibody bears only one reactive cysteine thiol group, a multitude of drug moieties may be attached through a dendritic linker.

Nonlimiting exemplary linkers are shown below in the context of an ADC of Formula I:

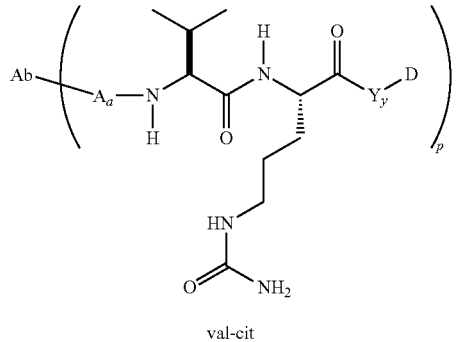

val-cit

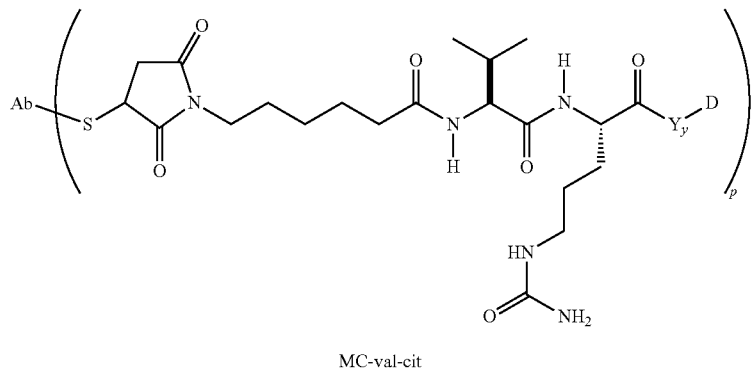

MC-val-cit

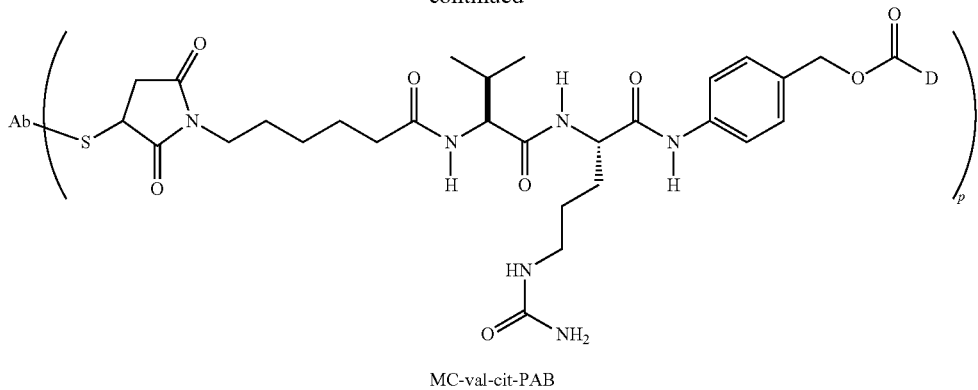

MC-val-cit-PAB

Further nonlimiting exemplary ADCs include the structures:

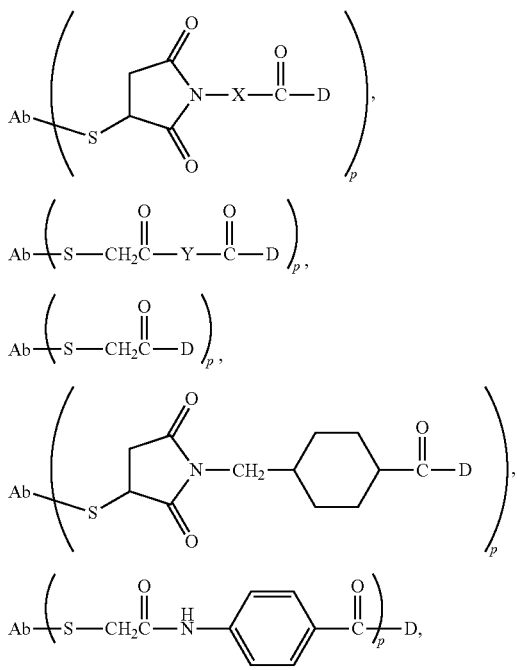

where X is:

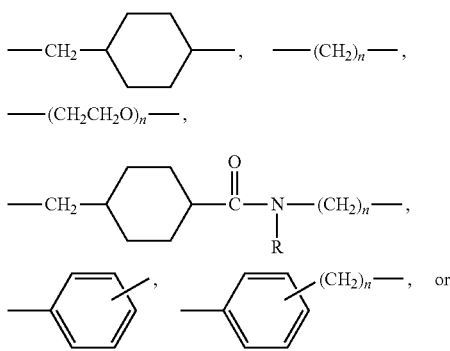

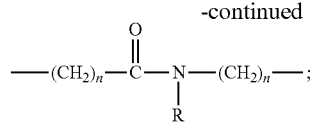

Y is:

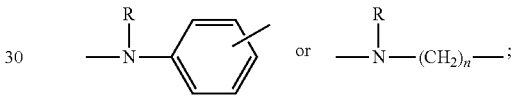

each R is independently H or $C_1$-$C_6$ alkyl; and n is 1 to 12.

Typically, peptide-type linkers can be prepared by forming a peptide bond between two or more amino acids and/or peptide fragments. Such peptide bonds can be prepared, for example, according to a liquid phase synthesis method (e.g., E. Schröder and K. Lübke (1965) "The Peptides", volume 1, pp 76-136, Academic Press).

In some embodiments, a linker is substituted with groups that modulate solubility and/or reactivity. As a nonlimiting example, a charged substituent such as sulfonate (—$SO_3$—) or ammonium may increase water solubility of the linker reagent and facilitate the coupling reaction of the linker reagent with the antibody and/or the drug moiety, or facilitate the coupling reaction of Ab-L (antibody-linker intermediate) with D, or D-L (drug-linker intermediate) with Ab, depending on the synthetic route employed to prepare the ADC. In some embodiments, a portion of the linker is coupled to the antibody and a portion of the linker is coupled to the drug, and then the Ab-(linker portion)$^a$ is coupled to drug-(linker portion)$^b$ to form the ADC of Formula I. In some such embodiments, the antibody comprises more than one (linker portion)$^a$ substituents, such that more than one drug is coupled to the antibody in the ADC of Formula I.

The compounds of the invention expressly contemplate, but are not limited to, ADC prepared with the following linker reagents: bis-maleimido-trioxyethylene glycol (BMPEO), N-(β-maleimidopropyloxy)-N-hydroxy succinimide ester (BMPS), N-(ε-maleimidocaproyloxy) succinimide ester (EMCS), N-[γ-maleimidobutyryloxy]succinimide ester (GMBS), 1,6-hexane-bis-vinylsulfone (HBVS), succinimidyl 4-(N-maleimidomethyl)cyclohexane-1-carboxy-(6-amidocaproate) (LC-SMCC), m-maleimidobenzoyl-N-hydroxysuccinimide ester (MBS), 4-(4-N-Maleimidophenyl)butyric acid hydrazide (MPBH), succinimidyl 3-(bromoacetamido)propionate (SBAP), succinimidyl iodoacetate (SIA), succinimidyl (4-iodoacetyl) aminobenzoate (SIAB), N-succinimidyl-3-(2-pyridyldithio)propionate (SPDP), N-succinimidyl-4-(2-pyridylthio)pentanoate (SPP), succinimidyl 4-(N-maleimidomethyl)cyclohexane-1-carboxylate (SMCC), succinimidyl 4-(p-maleimidophenyl)butyrate (SMPB), succinimidyl 6-[(beta-maleimidopropionamido)hexanoate](SMPH), iminothiolane (IT), sulfo-EMCS, sulfo-GMBS, sulfo-KMUS, sulfo-MBS, sulfo-SIAB, sulfo-SMCC, and sulfo-SMPB, and succinimidyl-(4-vinylsulfone)benzoate (SVSB), and including bis-maleimide reagents: dithiobismaleimidoethane (DTME), 1,4-Bismaleimidobutane (BMB), 1,4 Bismaleimidyl-2,3-dihydroxybutane (BMDB), bismaleimidohexane (BMH), bismaleimidoethane (BMOE), BM(PEG)$_2$ (shown below), and BM(PEG)$_3$ (shown below); bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). In some embodiments, bis-maleimide reagents allow the attachment of the thiol group of a cysteine in the antibody to a thiol-containing drug moiety, linker, or linker-drug intermediate. Other functional groups that are reactive with thiol groups include, but are not limited to, iodoacetamide, bromoacetamide, vinyl pyridine, disulfide, pyridyl disulfide, isocyanate, and isothiocyanate.

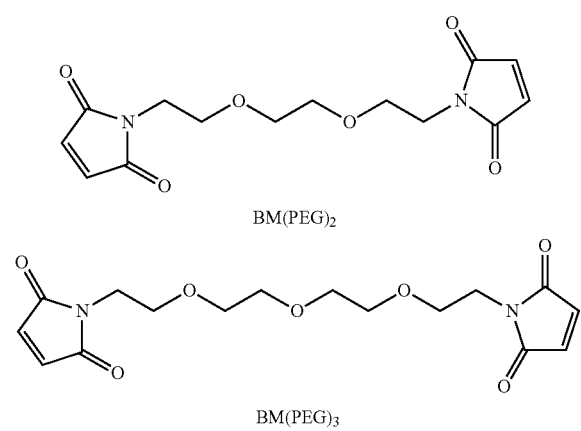

BM(PEG)$_2$

BM(PEG)$_3$

Certain useful linker reagents can be obtained from various commercial sources, such as Pierce Biotechnology, Inc. (Rockford, Ill.), Molecular Biosciences Inc. (Boulder, Colo.), or synthesized in accordance with procedures described in the art; for example, in Toki et al (2002) *J. Org. Chem.* 67:1866-1872; Dubowchik, et al. (1997) *Tetrahedron Letters*, 38:5257-60; Walker, M. A. (1995) *J. Org. Chem.* 60:5352-5355; Frisch et al (1996) *Bioconjugate Chem.* 7:180-186; U.S. Pat. No. 6,214,345; WO 02/088172; US 2003130189; US2003096743; WO 03/026577; WO 03/043583; and WO 04/032828.

Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., WO94/11026.

b) Exemplary Drug Moieties
(1) Maytansine and Maytansinoids
In some embodiments, an immunoconjugate comprises an antibody conjugated to one or more maytansinoid molecules. Maytansinoids are derivatives of maytansine, and are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinoids are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody-drug conjugates because they are: (i) relatively accessible to prepare by fermentation or chemical modification or derivatization of fermentation products, (ii) amenable to derivatization with functional groups suitable for conjugation through non-disulfide linkers to antibodies, (iii) stable in plasma, and (iv) effective against a variety of tumor cell lines.

Certain maytansinoids suitable for use as maytansinoid drug moieties are known in the art and can be isolated from natural sources according to known methods or produced using genetic engineering techniques (see, e.g., Yu et al (2002) PNAS 99:7968-7973). Maytansinoids may also be prepared synthetically according to known methods.

Exemplary maytansinoid drug moieties include, but are not limited to, those having a modified aromatic ring, such as: C-19-dechloro (U.S. Pat. No. 4,256,746) (prepared, for example, by lithium aluminum hydride reduction of ansamytocin P2); C-20-hydroxy (or C-20-demethyl)+/−C-19-dechloro (U.S. Pat. Nos. 4,361,650 and 4,307,016) (prepared, for example, by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared, for example, by acylation using acyl chlorides), and those having modifications at other positions of the aromatic ring.

Exemplary maytansinoid drug moieties also include those having modifications such as: C-9-SH (U.S. Pat. No. 4,424,219) (prepared, for example, by the reaction of maytansinol with H$_2$S or P$_2$S5); C-14-alkoxymethyl(demethoxy/CH$_2$OR) (U.S. Pat. No. 4,331,598); C-14-hydroxymethyl or acyloxymethyl (CH$_2$OH or CH$_2$OAc) (U.S. Pat. No. 4,450,254) (prepared, for example, from *Nocardia*); C-15-hydroxy/acyloxy (U.S. Pat. No. 4,364,866) (prepared, for example, by the conversion of maytansinol by *Streptomyces*); C-15-methoxy (U.S. Pat. Nos. 4,313,946 and 4,315,929) (for example, isolated from *Trewia nudlflora*); C-18-N-demethyl (U.S. Pat. Nos. 4,362,663 and 4,322,348) (prepared, for example, by the demethylation of maytansinol by *Streptomyces*); and 4,5-deoxy (U.S. Pat. No. 4,371,533) (prepared, for example, by the titanium trichloride/LAH reduction of maytansinol).

Many positions on maytansinoid compounds are useful as the linkage position. For example, an ester linkage may be formed by reaction with a hydroxyl group using conventional coupling techniques. In some embodiments, the reaction may occur at the C-3 position having a hydroxyl group, the C-14 position modified with hydroxymethyl, the C-15 position modified with a hydroxyl group, and the C-20 position having a hydroxyl group. In some embodiments, the linkage is formed at the C-3 position of maytansinol or a maytansinol analogue.

Maytansinoid drug moieties include those having the structure:

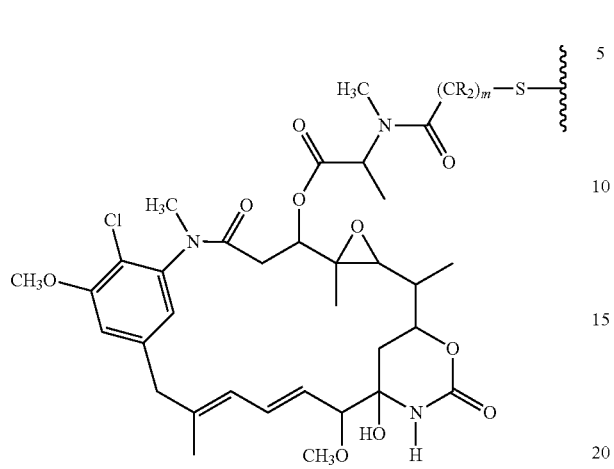

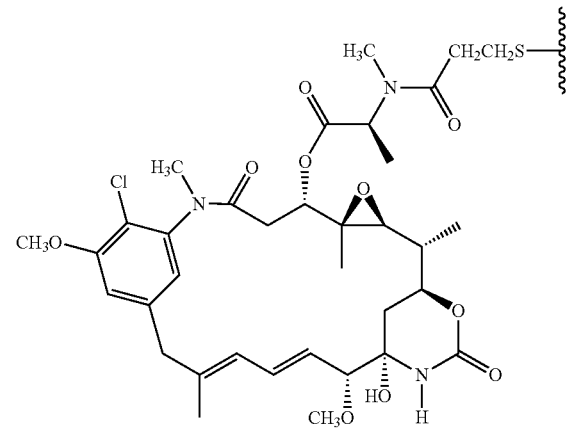

where the wavy line indicates the covalent attachment of the sulfur atom of the maytansinoid drug moiety to a linker of an ADC. Each R may independently be H or a $C_1$-$C_6$ alkyl. The alkylene chain attaching the amide group to the sulfur atom may be methanyl, ethanyl, or propyl, i.e., m is 1, 2, or 3 (U.S. 633410; U.S. Pat. No. 5,208,020; Chari et al (1992) Cancer Res. 52:127-131; Liu et al (1996) Proc. Natl. Acad. Sci USA 93:8618-8623).

All stereoisomers of the maytansinoid drug moiety are contemplated for the ADC of the invention, i.e. any combination of R and S configurations at the chiral carbons (U.S. Pat. No. 7,276,497; U.S. Pat. No. 6,913,748; U.S. Pat. No. 6,441,163; U.S. 633410 (RE39151); U.S. Pat. No. 5,208,020; Widdison et al (2006) J. Med. Chem. 49:4392-4408, which are incorporated by reference in their entirety). In some embodiments, the maytansinoid drug moiety has the following stereochemistry:

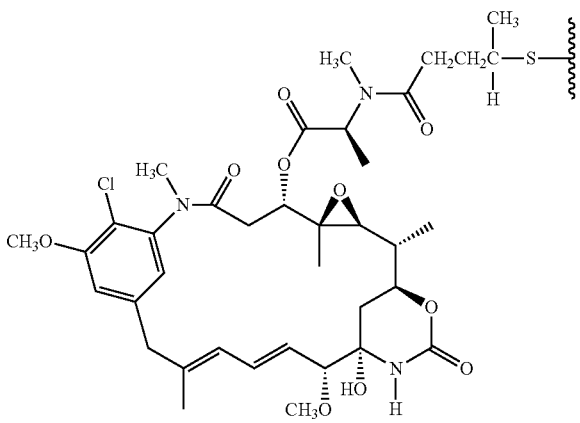

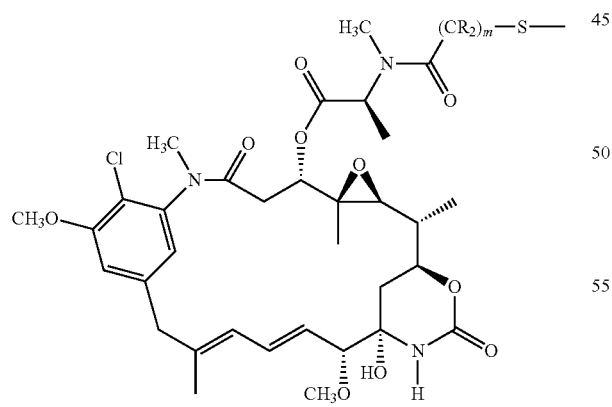

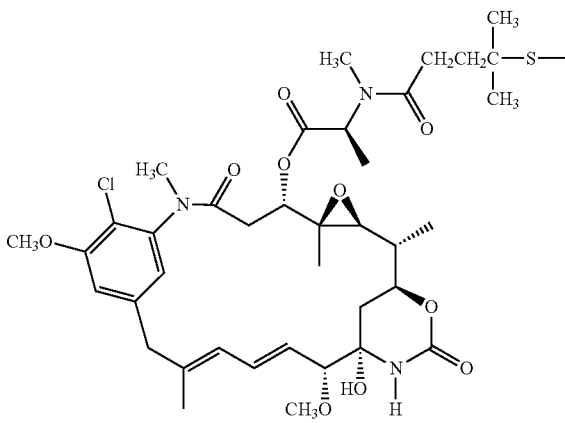

wherein the wavy line indicates the covalent attachment of the sulfur atom of the drug to a linker (L) of an antibody-drug conjugate.

Other exemplary maytansinoid antibody-drug conjugates have the following structures and abbreviations (wherein Ab is antibody and p is 1 to about 20. In some embodiments, p is 1 to 10, p is 1 to 7, p is 1 to 5, or p is 1 to 4):

Exemplary embodiments of maytansinoid drug moieties include, but are not limited to, DM1; DM3; and DM4, having the structures:

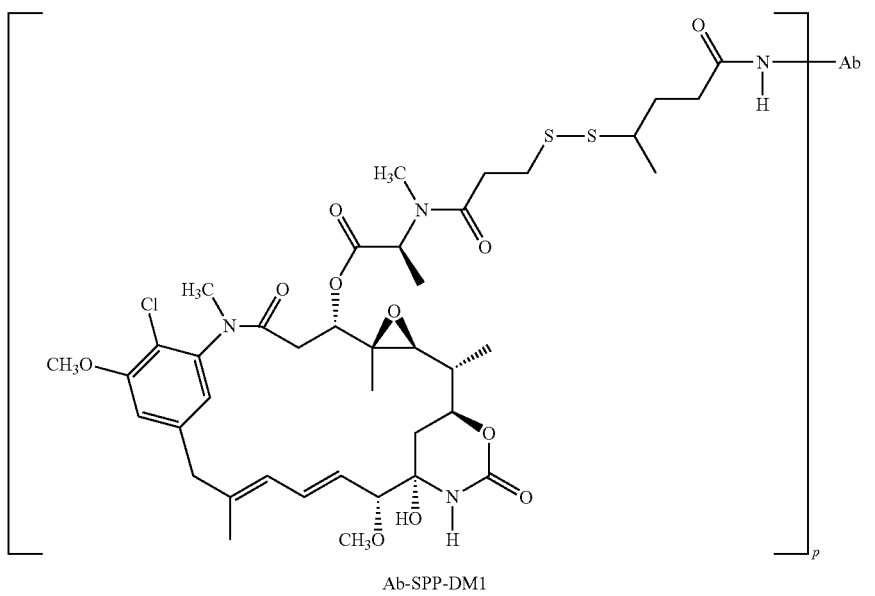
Ab-SPP-DM1
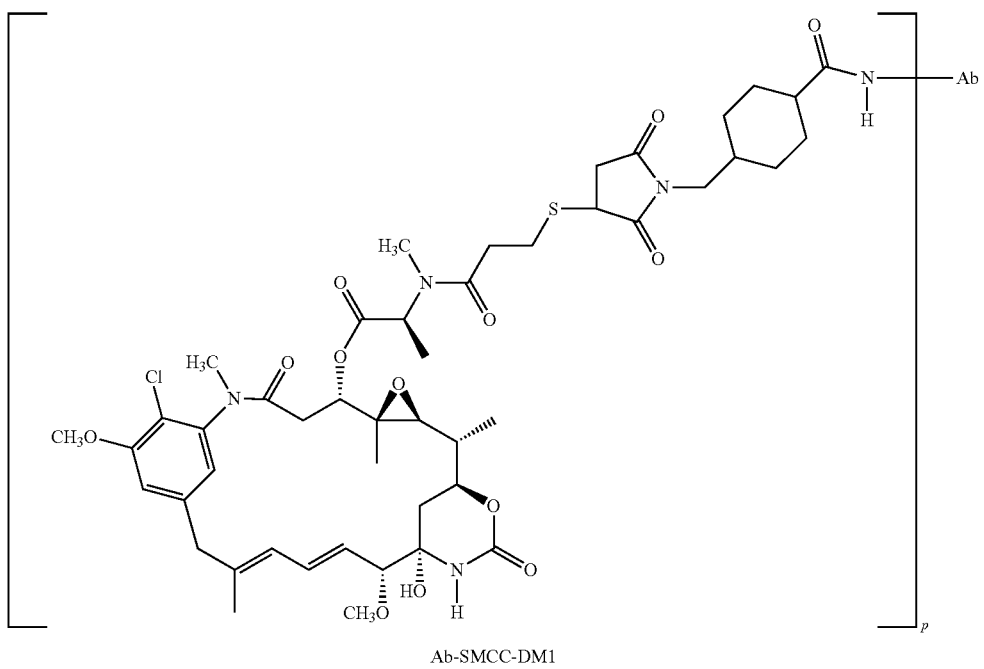
Ab-SMCC-DM1
Exemplary antibody-drug conjugates where DM1 is linked through a BMPEO linker to a thiol group of the antibody have the structure and abbreviation:

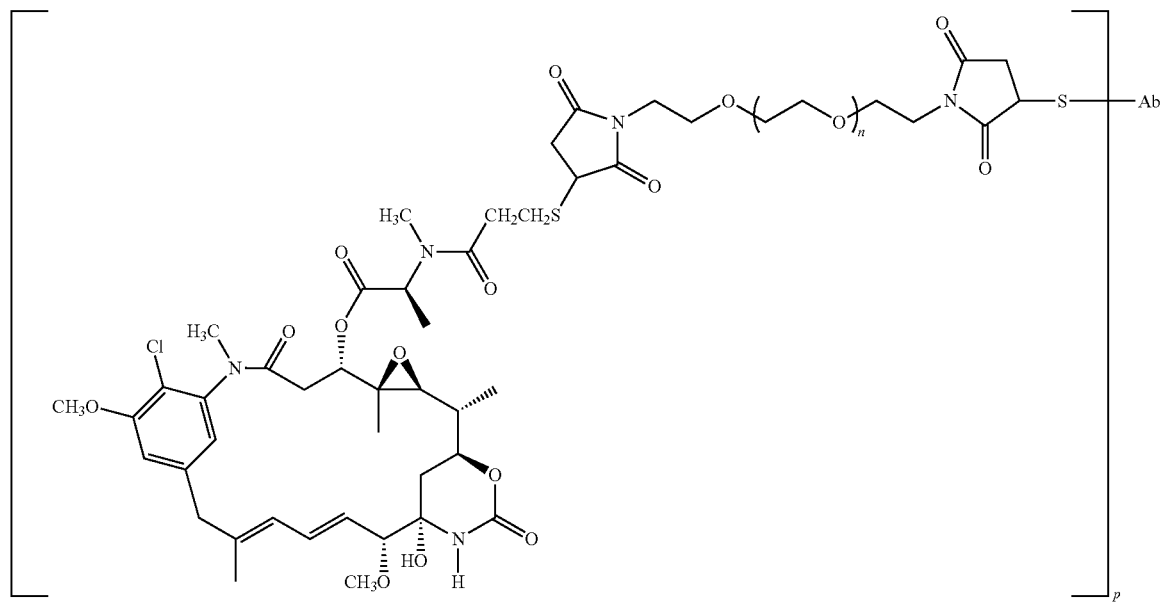

where Ab is antibody; n is 0, 1, or 2; and p is 1 to about 20. In some embodiments, p is 1 to 10, p is 1 to 7, p is 1 to 5, or p is 1 to 4.

Immunoconjugates containing maytansinoids, methods of making the same, and their therapeutic use are disclosed, for example, in U.S. Pat. Nos. 5,208,020 and 5,416,064; US 2005/0276812 A1; and European Patent EP 0 425 235 B1, the disclosures of which are hereby expressly incorporated by reference. See also Liu et al. Proc. Natl. Acad. Sci. USA 93:8618-8623 (1996); and Chari et al. Cancer Research 52:127-131 (1992).

In some embodiments, antibody-maytansinoid conjugates may be prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). In some embodiments, ADC with an average of 3-4 maytansinoid molecules conjugated per antibody molecule has shown efficacy in enhancing cytotoxicity of target cells without negatively affecting the function or solubility of the antibody. In some instances, even one molecule of toxin/antibody is expected to enhance cytotoxicity over the use of naked antibody.

Exemplary linking groups for making antibody-maytansinoid conjugates include, for example, those described herein and those disclosed in U.S. Pat. No. 5,208,020; EP Patent 0 425 235 B1; Chari et al. Cancer Research 52:127-131 (1992); US 2005/0276812 A1; and US 2005/016993 A1, the disclosures of which are hereby expressly incorporated by reference.

(2) Auristatins and Dolastatins

Drug moieties include dolastatins, auristatins, and analogs and derivatives thereof (U.S. Pat. No. 5,635,483; U.S. Pat. No. 5,780,588; U.S. Pat. No. 5,767,237; U.S. Pat. No. 6,124,431). Auristatins are derivatives of the marine mollusk compound dolastatin-10. While not intending to be bound by any particular theory, dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin/auristatin drug moiety may be attached to the antibody through the N (amino) terminus or the C (carboxyl) terminus of the peptidic drug moiety (WO 02/088172; Doronina et al (2003) Nature Biotechnology 21(7):778-784; Francisco et al (2003) Blood 102(4): 1458-1465).

Exemplary auristatin embodiments include the N-terminus linked monomethylauristatin drug moieties $D_E$ and $D_F$, disclosed in U.S. Pat. No. 7,498,298 and U.S. Pat. No. 7,659,241, the disclosures of which are expressly incorporated by reference in their entirety:

$D_E$

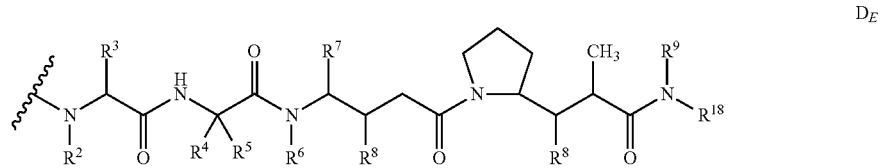

-continued $D_F$

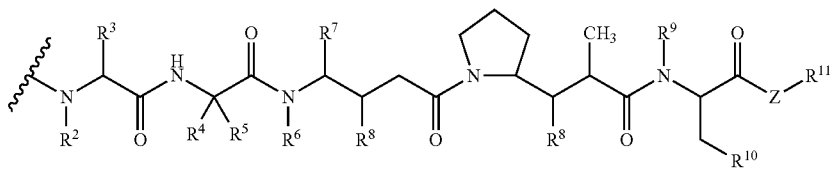

wherein the wavy line of $D_E$ and $D_F$ indicates the covalent attachment site to an antibody or antibody-linker component, and independently at each location:

$R^2$ is selected from H and $C_1$-$C_8$ alkyl;

$R^3$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

$R^{11}$ is selected from aryl or $C_3$-$C_8$ heterocycle;

Z is O, S, NH, or $NR^{12}$, wherein $R^{12}$ is $C_1$-$C_8$ alkyl;

$R^{11}$ is selected from H, $C_1$-$C_{20}$ alkyl, aryl, $C_3$-$C_8$ heterocycle, —$(R^{13}O)_m$—$R^{14}$, or —$(R^{13}O)_m$—$CH(R^{15})_2$;

m is an integer ranging from 1-1000;

$R^{13}$ is $C_2$-$C_8$ alkyl;

$R^{14}$ is H or $C_1$-$C_8$ alkyl;

each occurrence of $R^{15}$ is independently H, COOH, —$(CH_2)_n$—$N(R^{16})_2$, —$(CH_2)_n$—$SO_3H$, or —$(CH_2)_n$—$SO_3$—$C_1$-$C_8$ alkyl;

each occurrence of $R^{16}$ is independently H, $C_1$-$C_8$ alkyl, or —$(CH_2)$—COOH;

$R^{18}$ is selected from —$C(R^8)_2$—$C(R^8)_2$-aryl, —$C(R^8)_2$—$C(R^8)_2$—($C_3$-$C_8$ heterocycle), and —$C(R^8)_2$—$C(R^8)_2$—($C_3$-$C_8$ carbocycle); and n is an integer ranging from 0 to 6.

In one embodiment, $R^3$, $R^4$ and $R^7$ are independently isopropyl or sec-butyl and $R^5$ is —H or methyl. In an exemplary embodiment, $R^3$ and $R^4$ are each isopropyl, $R^5$ is —H, and $R^7$ is sec-butyl.

In yet another embodiment, $R^2$ and $R^6$ are each methyl, and $R^9$ is —H.

In still another embodiment, each occurrence of $R^8$ is —$OCH_3$.

In an exemplary embodiment, $R^3$ and $R^4$ are each isopropyl, $R^2$ and $R^6$ are each methyl, $R^5$ is —H, $R^7$ is sec-butyl, each occurrence of $R^8$ is —$OCH_3$, and $R^9$ is —H.

In one embodiment, Z is —O— or —NH—.

In one embodiment, $R^{10}$ is aryl.

In an exemplary embodiment, $R^{10}$ is -phenyl.

In an exemplary embodiment, when Z is —O—, $R^{11}$ is —H, methyl or t-butyl.

In one embodiment, when Z is —NH, $R^{11}$ is —$CH(R^{15})_2$, wherein $R^{15}$ is —$(CH_2)$—$N(R^{16})_2$, and $R^{16}$ is —$C_1$-$C_8$ alkyl or —$(CH_2)_n$—COOH.

In another embodiment, when Z is —NH, $R^{11}$ is —$CH(R^{15})_2$, wherein $R^{15}$ is —$(CH_2)$—$SO_3H$.

An exemplary auristatin embodiment of formula $D_E$ is MMAE, wherein the wavy line indicates the covalent attachment to a linker (L) of an antibody-drug conjugate:

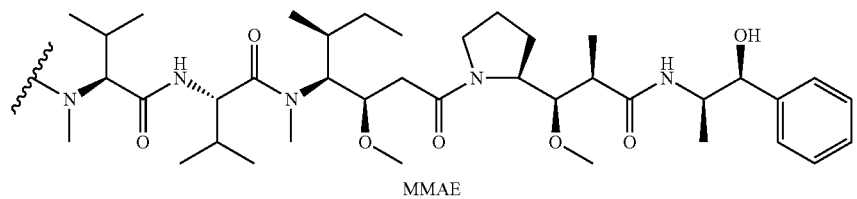 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

MMAE

An exemplary auristatin embodiment of formula $D_F$ is MMAF, wherein the wavy line indicates the covalent attachment to a linker (L) of an antibody-drug conjugate:

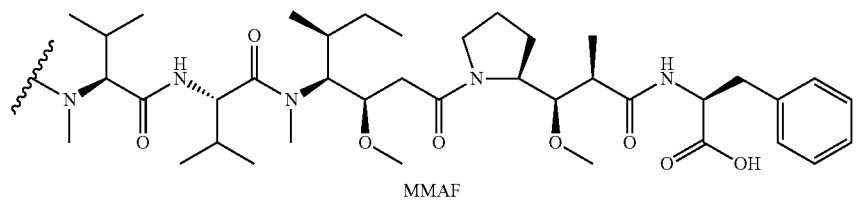

MMAF

Other exemplary embodiments include monomethylvaline compounds having phenylalanine carboxy modifications at the C-terminus of the pentapeptide auristatin drug moiety (WO 2007/008848) and monomethylvaline compounds having phenylalanine sidechain modifications at the C-terminus of the pentapeptide auristatin drug moiety (WO 2007/008603).

Nonlimiting exemplary embodiments of ADC of Formula I comprising MMAE or MMAF and various linker components have the following structures and abbreviations (wherein "Ab" is an antibody; p is 1 to about 8, "Val-Cit" is a valine-citrulline dipeptide; and "S" is a sulfur atom:

method (see, e.g., E. Schröder and K. Lübke, "The Peptides", volume 1, pp 76-136, 1965, Academic Press). Auristatin/dolastatin drug moieties may, in some embodiments, be prepared according to the methods of: U.S. Pat. No. 7,498,298; U.S. Pat. No. 5,635,483; U.S. Pat. No. 5,780,588; Pettit et al (1989) *J. Am. Chem. Soc.* 111:5463-5465; Pettit et al (1998) *Anti-Cancer Drug Design* 13:243-277; Pettit, G. R., et al. *Synthesis*, 1996, 719-725; Pettit et al (1996) *J. Chem. Soc. Perkin Trans.* 1 5:859-863; and Doronina (2003) *Nat. Biotechnol.* 21(7):778-784.

In some embodiments, auristatin/dolastatin drug moieties of formulas $D_E$ such as MMAE, and $D_F$, such as MMAF, and

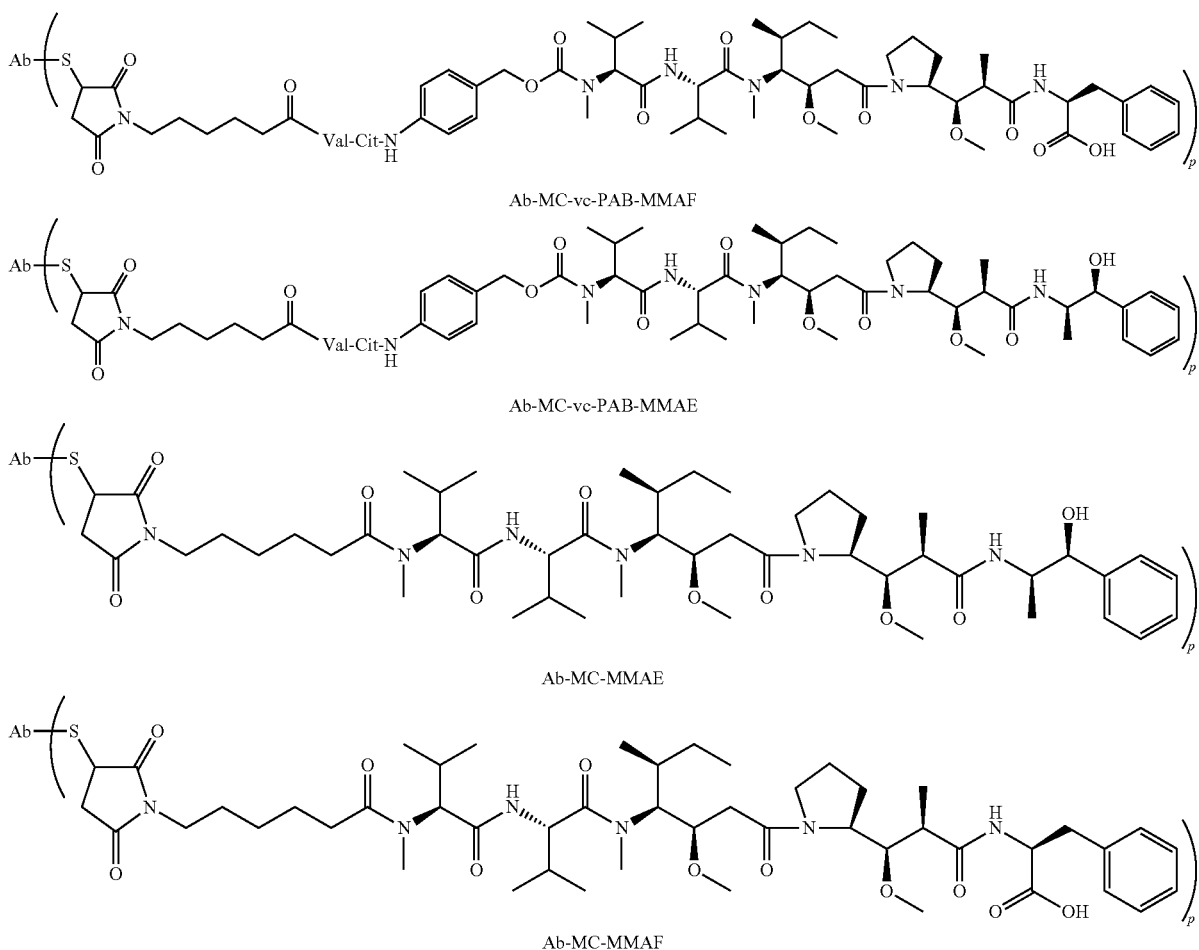

Ab-MC-vc-PAB-MMAF

Ab-MC-vc-PAB-MMAE

Ab-MC-MMAE

Ab-MC-MMAF

Nonlimiting exemplary embodiments of ADCs of Formula I comprising MMAF and various linker components further include Ab-MC-PAB-MMAF and Ab-PAB-MMAF. Immunoconjugates comprising MMAF attached to an antibody by a linker that is not proteolytically cleavable have been shown to possess activity comparable to immunoconjugates comprising MMAF attached to an antibody by a proteolytically cleavable linker (Doronina et al. (2006) *Bioconjugate Chem.* 17:114-124). In some such embodiments, drug release is believed to be effected by antibody degradation in the cell.

Typically, peptide-based drug moieties can be prepared by forming a peptide bond between two or more amino acids and/or peptide fragments. Such peptide bonds can be prepared, for example, according to a liquid phase synthesis drug-linker intermediates and derivatives thereof, such as MC-MMAF, MC-MMAE, MC-vc-PAB-MMAF, and MC-vc-PAB-MMAE, may be prepared using methods described in U.S. Pat. No. 7,498,298; Doronina et al. (2006) *Bioconjugate Chem.* 17:114-124; and Doronina et al. (2003) *Nat. Biotech.* 21:778-784 and then conjugated to an antibody of interest.

(3) Calicheamicin

In some embodiments, the immunoconjugate comprises an antibody conjugated to one or more calicheamicin molecules. The calicheamicin family of antibiotics, and analogues thereof, are capable of producing double-stranded DNA breaks at sub-picomolar concentrations (Hinman et al., (1993) *Cancer Research* 53:3336-3342; Lode et al., (1998) *Cancer Research* 58:2925-2928). Calicheamicin has intracellular sites of action but, in certain instances, does not readily cross the plasma membrane. Therefore, cellular uptake of these agents through antibody-mediated internalization may, in some embodiments, greatly enhances their cytotoxic effects. Nonlimiting exemplary methods of preparing antibody-drug conjugates with a calicheamicin drug moiety are described, for example, in U.S. Pat. No. 5,712,374; U.S. Pat. No. 5,714,586; U.S. Pat. No. 5,739,116; and U.S. Pat. No. 5,767,285.

(4) Pyrrolobenzodiazepines

In some embodiments, an ADC comprises a pyrrolobenzodiazepine (PBD). In some embodiments, PDB dimers recognize and bind to specific DNA sequences. The natural product anthramycin, a PBD, was first reported in 1965 (Leimgruber, et al., (1965) *J. Am. Chem. Soc.*, 87:5793-5795; Leimgruber, et al., (1965) *J. Am. Chem. Soc.*, 87:5791-5793). Since then, a number of PBDs, both naturally-occurring and analogues, have been reported (Thurston, et al., (1994) *Chem. Rev.* 1994, 433-465 including dimers of the tricyclic PBD scaffold (U.S. Pat. No. 6,884,799; U.S. Pat. No. 7,049,311; U.S. Pat. No. 7,067,511; U.S. Pat. No. 7,265,105; U.S. Pat. No. 7,511,032; U.S. Pat. No. 7,528,126; U.S. Pat. No. 7,557,099). Without intending to be bound by any particular theory, it is believed that the dimer structure imparts the appropriate three-dimensional shape for isohelicity with the minor groove of B-form DNA, leading to a snug fit at the binding site (Kohn, In Antibiotics III. Springer-Verlag, New York, pp. 3-11 (1975); Hurley and Needham-VanDevanter, (1986) *Acc. Chem. Res.*, 19:230-237). Dimeric PBD compounds bearing C2 aryl substituents have been shown to be useful as cytotoxic agents (Hartley et al (2010) *Cancer Res.* 70(17):6849-6858; Antonow (2010) *J. Med. Chem.* 53(7):2927-2941; Howard et al (2009) *Bioorganic and Med. Chem. Letters* 19(22):6463-6466).

In some embodiments, PBD compounds can be employed as prodrugs by protecting them at the N10 position with a nitrogen protecting group which is removable in vivo (WO 00/12507; WO 2005/023814).

PBD dimers have been conjugated to antibodies and the resulting ADC shown to have anti-cancer properties (US 2010/0203007). Nonlimiting exemplary linkage sites on the PBD dimer include the five-membered pyrrolo ring, the tether between the PBD units, and the N10-C11 imine group (WO 2009/016516; US 2009/304710; US 2010/047257; US 2009/036431; US 2011/0256157; WO 2011/130598).

Nonlimiting exemplary PBD dimer components of ADCs are of Formula A:

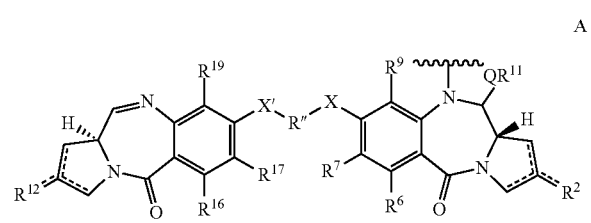

A and salts and solvates thereof, wherein:
the wavy line indicates the covalent attachment site to the linker;
the dotted lines indicate the optional presence of a double bond between C1 and C2 or C2 and C3;
$R^2$ is independently selected from H, OH, =O, =CH$_2$, CN, R, OR, =CH—R$^D$, =C(R$^D$)$_2$, O—SO$_2$—R, CO$_2$R and COR, and optionally further selected from halo or dihalo, wherein $R^D$ is independently selected from R, CO$_2$R, COR, CHO, CO$_2$H, and halo;

$R^6$ and $R^9$ are independently selected from H, R, OH, OR, SH, SR, NH$_2$, NHR, NRR', NO$_2$, Me$_3$Sn and halo;

$R^7$ is independently selected from H, R, OH, OR, SH, SR, NH$_2$, NHR, NRR', NO$_2$, Me$_3$Sn and halo;

Q is independently selected from O, S and NH;

$R^{11}$ is either H, or R or, where Q is O, SO$_3$M, where M is a metal cation;

R and R' are each independently selected from optionally substituted C$_{1-8}$ alkyl, C$_{1-12}$ alkyl, C$_{3-8}$ heterocyclyl, C$_{3-20}$ heterocycle, and C$_{5-20}$ aryl groups, and optionally in relation to the group NRR', R and R' together with the nitrogen atom to which they are attached form an optionally substituted 4-, 5-, 6- or 7-membered heterocyclic ring;

$R^{12}$, $R^{16}$, $R^{19}$ and $R^{17}$ are as defined for $R^2$, $R^6$, $R^9$ and $R^7$ respectively;

R" is a C$_{3-12}$ alkylene group, which chain may be interrupted by one or more heteroatoms, e.g. O, S, N(H), NMe and/or aromatic rings, e.g. benzene or pyridine, which rings are optionally substituted; and X and X' are independently selected from O, S and N(H).

In some embodiments, R and R' are each independently selected from optionally substituted C$_{1-12}$ alkyl, C$_{3-20}$ heterocycle, and C$_{5-20}$ aryl groups, and optionally in relation to the group NRR', R and R' together with the nitrogen atom to which they are attached form an optionally substituted 4-, 5-, 6- or 7-membered heterocyclic ring.

In some embodiments, $R^9$ and $R^{19}$ are H.

In some embodiments, $R^6$ and $R^{16}$ are H.

In some embodiments, $R^7$ are $R^{17}$ are both OR$^{7A}$, where $R^{7A}$ is optionally substituted C$_{1-4}$ alkyl.

In some embodiments, $R^{7A}$ is Me.

In some embodiments, X is O.

In some embodiments, $R^{11}$ is H.

In some embodiments, there is a double bond between C2 and C3 in each monomer unit.

In some embodiments, $R^2$ and $R^{12}$ are independently selected from H and R. In some embodiments, $R^2$ and $R^{12}$ are independently R. In some embodiments, $R^2$ and $R^{12}$ are independently optionally substituted C$_{5-20}$ aryl or C$_{5-7}$ aryl or C$_{8-10}$ aryl. In some embodiments, $R^2$ and $R^{12}$ are independently optionally substituted phenyl, thienyl, napthyl, pyridyl, quinolinyl, or isoquinolinyl. In some embodiments, $R^2$ and $R^{12}$ are independently selected from =O, =CH$_2$, =CH—R$^D$, and =C(R$^D$)$_2$. In some embodiments, $R^2$ and $R^{12}$ are =CH$_2$. In some embodiments, $R^2$ and $R^{12}$ are each H. In some embodiments, $R^2$ and $R^{12}$ are each =O. In some embodiments, $R^2$ and $R^{12}$ are each =CF$_2$. In some embodiments, $R^2$ and/or $R^{12}$ are independently =C(R$^D$)$_2$. In some embodiments, $R^2$ and/or $R^{12}$ are independently =CH—R$^D$.

In some embodiments, when $R^2$ and/or $R^{12}$ is =CH—R$^D$, each group may independently have either configuration shown below:

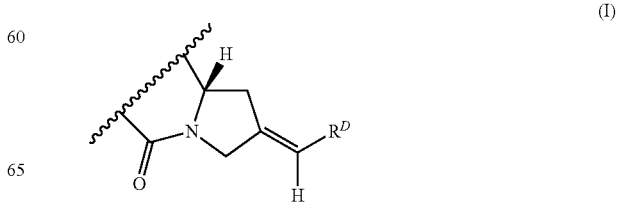

(I)

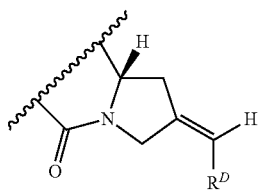
(II)

In some embodiments, a =CH—R$^D$ is in configuration (I).

In some embodiments, R" is a C$_3$ alkylene group or a C$_5$ alkylene group.

In some embodiments, an exemplary PBD dimer component of an ADC has the structure of Formula A(I):

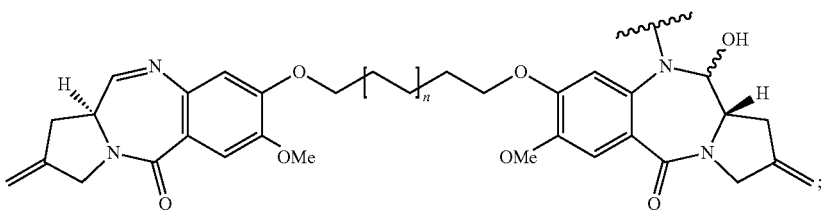

A(I)

wherein n is 0 or 1.

In some embodiments, an exemplary PBD dimer component of an ADC has the structure of Formula A(II):

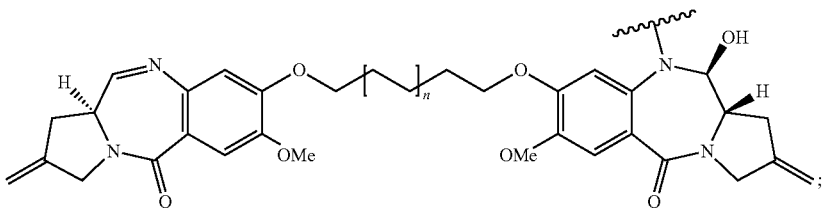

A(II)

wherein n is 0 or 1.

In some embodiments, an exemplary PBD dimer component of an ADC has the structure of Formula A(III):

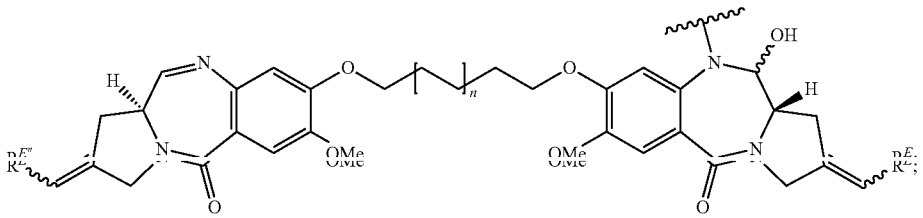

A(III)

wherein R$^E$ and R$^{E''}$ are each independently selected from H or R$^D$, wherein R$^D$ is defined as above; and wherein n is 0 or 1.

In some embodiments, n is 0. In some embodiments, n is 1. In some embodiments, R$^E$ and/or R$^{E''}$ is H. In some embodiments, R$^E$ and R$^{E''}$ are H. In some embodiments, R$^E$ and/or R$^{E''}$ is R$^D$, wherein R$^D$ is optionally substituted C$_{1-12}$ alkyl. In some embodiments, R$^E$ and/or R$^{E''}$ is R$^D$, wherein R$^D$ is methyl.

In some embodiments, an exemplary PBD dimer component of an ADC has the structure of Formula A(IV):

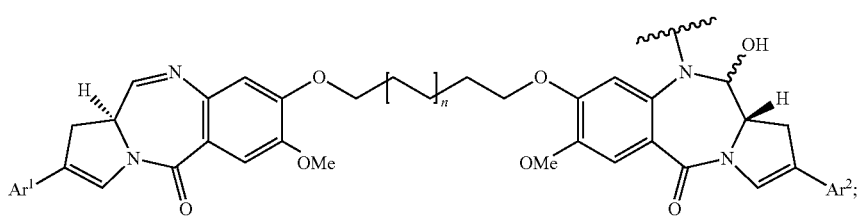

A(IV)

wherein Ar¹ and Ar² are each independently optionally substituted $C_{5-20}$ aryl; wherein Ar¹ and Ar² may be the same or different; and wherein n is 0 or 1.

In some embodiments, an exemplary PBD dimer component of an ADC has the structure of Formula A(V):

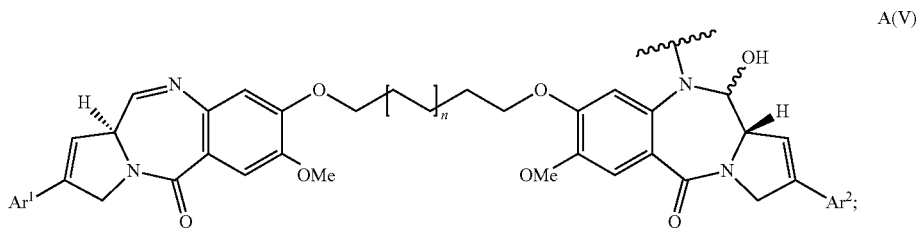

A(V)

wherein Ar¹ and Ar² are each independently optionally substituted $C_{5-20}$ aryl; wherein Ar¹ and Ar² may be the same or different; and wherein n is 0 or 1.

In some embodiments, Ar¹ and Ar² are each independently selected from optionally substituted phenyl, furanyl, thiophenyl and pyridyl. In some embodiments, Ar¹ and Ar² are each independently optionally substituted phenyl. In some embodiments, Ar¹ and Ar² are each independently optionally substituted thien-2-yl or thien-3-yl. In some embodiments, Ar¹ and Ar² are each independently optionally substituted quinolinyl or isoquinolinyl. The quinolinyl or isoquinolinyl group may be bound to the PBD core through any available ring position. For example, the quinolinyl may be quinolin-2-yl, quinolin-3-yl, quinolin-4yl, quinolin-5-yl, quinolin-6-yl, quinolin-7-yl and quinolin-8-yl. In some embodiments, the quinolinyl is selected from quinolin-3-yl and quinolin-6-yl. The isoquinolinyl may be isoquinolin-1-yl, isoquinolin-3-yl, isoquinolin-4-yl, isoquinolin-5-yl, isoquinolin-6-yl, isoquinolin-7-yl and isoquinolin-8-yl. In some embodiments, the isoquinolinyl is selected from isoquinolin-3-yl and isoquinolin-6-yl.

Further nonlimiting exemplary PBD dimer components of ADCs are of Formula B:

and salts and solvates thereof, wherein:

the wavy line indicates the covalent attachment site to the linker;

the wavy line connected to the OH indicates the S or R configuration;

$R^{V1}$ and $R^{V2}$ are independently selected from H, methyl, ethyl and phenyl (which phenyl may be optionally substituted with fluoro, particularly in the 4 position) and $C_{5-6}$ heterocyclyl; and n is 0 or 1.

In some embodiments, $R^{V1}$ and $R^{V2}$ are independently selected from H, phenyl, and 4-fluorophenyl.

In some embodiments, a linker may be attached at one of various sites of the PBD dimer drug moiety, including the N10 imine of the B ring, the C-2 endo/exo position of the C ring, or the tether unit linking the A rings (see structures C(I) and C(II) below).

Nonlimiting exemplary PBD dimer components of ADCs include Formulas C(I) and C(II):

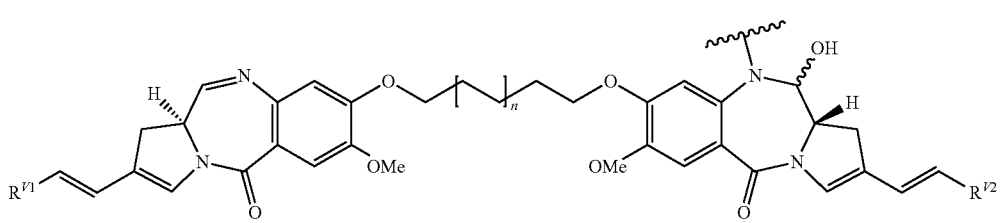

B

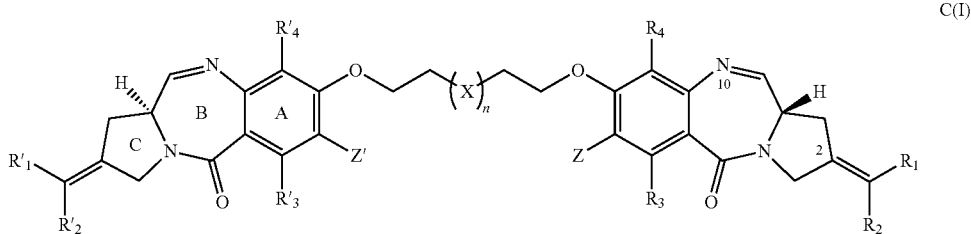

C(I)

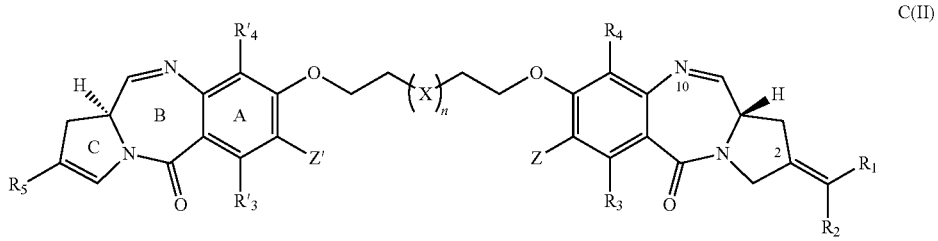

C(II)

Formulas C(I) and C(II) are shown in their N10-C11 imine form. Exemplary PBD drug moieties also include the carbinolamine and protected carbinolamine forms as well, as shown in the box below:

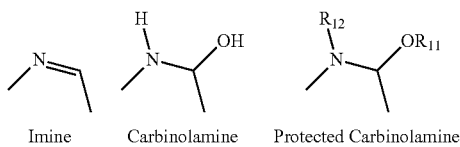

Imine    Carbinolamine    Protected Carbinolamine wherein:

X is $CH_2$ (n=1 to 5), N, or O;

Z and Z' are independently selected from OR and $NR_2$, where R is a primary, secondary or tertiary alkyl chain containing 1 to 5 carbon atoms;

$R_1$, $R'_1$, $R_2$ and $R'_2$ are each independently selected from H, $C_1$-$C_8$ alkyl, $C_2$-$C_8$ alkenyl, $C_2$-$C_8$ alkynyl, $C_{5-20}$ aryl (including substituted aryls), $C_{5-20}$ heteroaryl groups, —$NH_2$, —NHMe, —OH, and —SH, where, in some embodiments, alkyl, alkenyl and alkynyl chains comprise up to 5 carbon atoms;

$R_3$ and $R'_3$ are independently selected from H, OR, NHR, and $NR_2$, where R is a primary, secondary or tertiary alkyl chain containing 1 to 5 carbon atoms;

$R_4$ and $R'_4$ are independently selected from H, Me, and OMe;

$R_5$ is selected from $C_1$-$C_8$ alkyl, $C_2$-$C_8$ alkenyl, $C_2$-$C_8$ alkynyl, $C_{5-20}$ aryl (including aryls substituted by halo, nitro, cyano, alkoxy, alkyl, heterocyclyl) and $C_{5-20}$ heteroaryl groups, where, in some embodiments, alkyl, alkenyl and alkynyl chains comprise up to 5 carbon atoms;

$R_{11}$ is H, $C_1$-$C_8$ alkyl, or a protecting group (such as acetyl, trifluoroacetyl, t-butoxycarbonyl (BOC), benzyloxycarbonyl (CBZ), 9-fluorenylmethylenoxycarbonyl (Fmoc), or a moiety comprising a self-immolating unit such as valine-citrulline-PAB);

$R_{12}$ is H, $C_1$-$C_8$ alkyl, or a protecting group;

wherein a hydrogen of one of $R_1$, $R'_1$, $R_2$, $R'_2$, $R_5$, or $R_{12}$ or a hydrogen of the —$OCH_2CH_2(X)CH_2CH_2O$— spacer between the A rings is replaced with a bond connected to the linker of the ADC.

Exemplary PDB dimer portions of ADC include, but are not limited to (the wavy line indicates the site of covalent attachment to the linker):

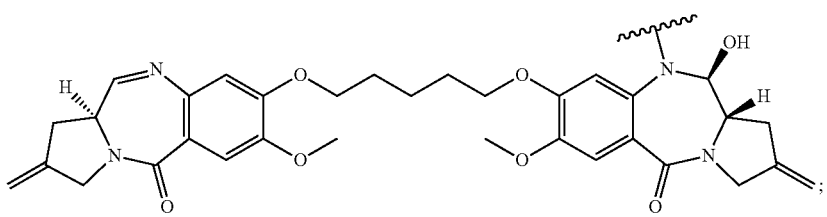

PBD dimer

Nonlimiting exemplary embodiments of ADCs comprising PBD dimers have the following structures:

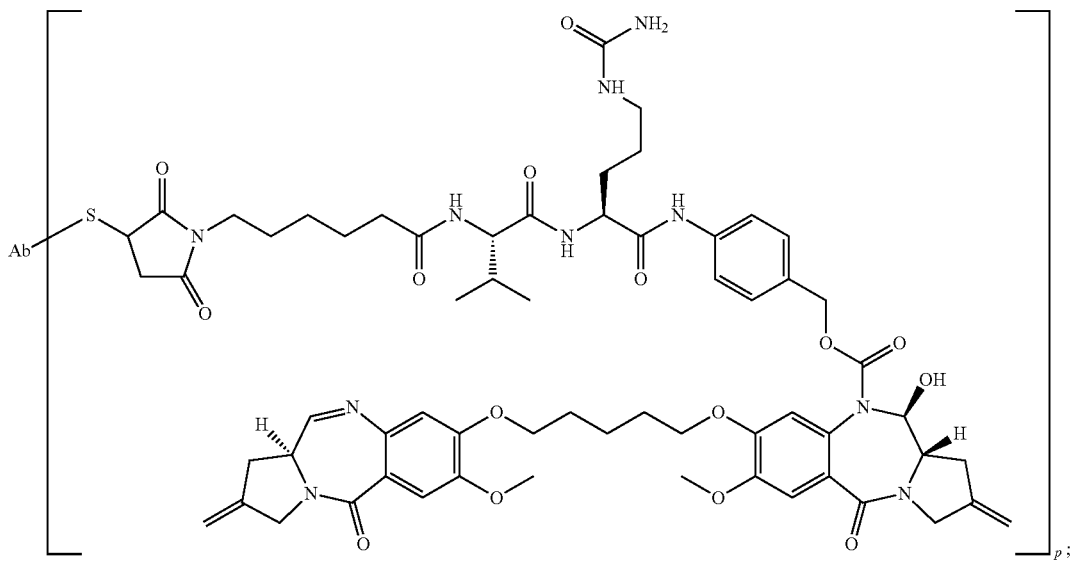
PBD dimer-val-cit-PAB-Ab

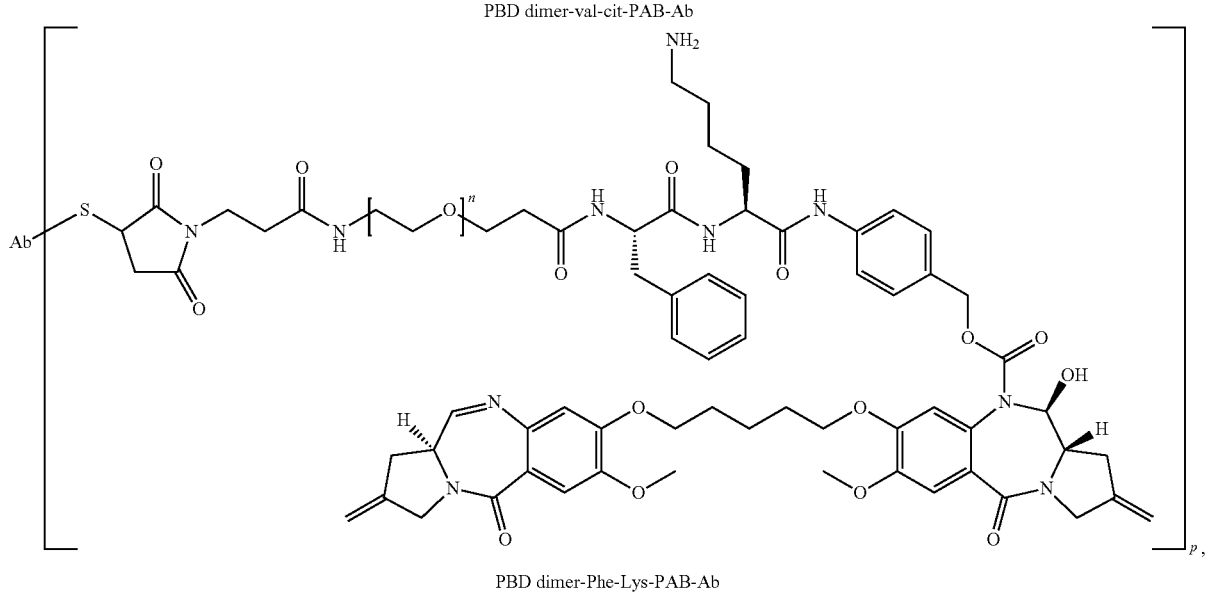
PBD dimer-Phe-Lys-PAB-Ab wherein:

n is 0 to 12. In some embodiments, n is 2 to 10. In some embodiments, n is 4 to 8. In some embodiments, n is selected from 4 and 8.

The linkers of PBD dimer-val-cit-PAB-Ab and the PBD dimer-Phe-Lys-PAB-Ab are protease cleavable, while the linker of PBD dimer-maleimide-acetal is acid-labile.

PBD dimers and ADC comprising PBD dimers may be prepared according to methods known in the art. See, e.g., WO 2009/016516; US 2009/304710; US 2010/047257; US 2009/036431; US 2011/0256157; WO 2011/130598.

(5) Anthracyclines

In some embodiments, an ADC comprising anthracycline. Anthracyclines are antibiotic compounds that exhibit cytotoxic activity. While not intending to be bound by any particular theory, studies have indicated that anthracyclines may operate to kill cells by a number of different mechanisms, including: 1) intercalation of the drug molecules into the DNA of the cell thereby inhibiting DNA-dependent nucleic acid synthesis; 2) production by the drug of free radicals which then react with cellular macromolecules to cause damage to the cells, and/or 3) interactions of the drug molecules with the cell membrane (see, e.g., C. Peterson et al., "Transport And Storage Of Anthracycline In Experimental Systems And Human Leukemia" in *Anthracycline Antibiotics In Cancer Therapy*; N. R. Bachur, "Free Radical Damage" id. at pp. 97-102). Because of their cytotoxic potential anthracyclines have been used in the treatment of numerous cancers such as leukemia, breast carcinoma, lung carcinoma, ovarian adenocarcinoma and sarcomas (see e.g., P. H Wiernik, in *Anthracycline: Current Status And New Developments* p 11).

Nonlimiting exemplary anthracyclines include doxorubicin, epirubicin, idarubicin, daunomycin, nemorubicin, and derivatives thereof. Immunoconjugates and prodrugs of daunorubicin and doxorubicin have been prepared and studied (Kratz et al (2006) *Current Med. Chem.* 13:477-523; Jeffrey et al (2006) *Bioorganic & Med. Chem. Letters* 16:358-362; Torgov et al (2005) *Bioconj. Chem.* 16:717-721; Nagy et al (2000) *Proc. Natl. Acad. Sci. USA* 97:829-834; Dubowchik et al (2002) *Bioorg. & Med. Chem. Letters* 12:1529-1532; King et al (2002) *J. Med. Chem.* 45:4336-4343; EP 0328147; U.S. Pat. No. 6,630,579). The antibody-drug conjugate BR96-doxorubicin reacts specifically with the tumor-associated antigen Lewis-Y and has been evaluated in phase I and II studies (Saleh et al (2000) *J. Clin. Oncology* 18:2282-2292; Ajani et al (2000) *Cancer Jour.* 6:78-81; Tolcher et al (1999) *J. Clin. Oncology* 17:478-484).

PNU-159682 is a potent metabolite (or derivative) of nemorubicin (Quintieri, et al. (2005) *Clinical Cancer Research* 11(4):1608-1617). Nemorubicin is a semisynthetic analog of doxorubicin with a 2-methoxymorpholino group on the glycoside amino of doxorubicin and has been under clinical evaluation (Grandi et al (1990) *Cancer Treat. Rev.* 17:133; Ripamonti et al (1992) *Brit. J. Cancer* 65:703), including phase II/III trials for hepatocellular carcinoma (Sun et al (2003) *Proceedings of the American Society for Clinical Oncology* 22, Abs1448; Quintieri (2003) *Proceedings of the American Association of Cancer Research*, 44: 1st Ed, Abs 4649; Pacciarini et al (2006) *Jour. Clin. Oncology* 24:14116).

A nonlimiting exemplary ADC comprising nemorubicin or nemorubicin derivatives is shown in Formula Ia:

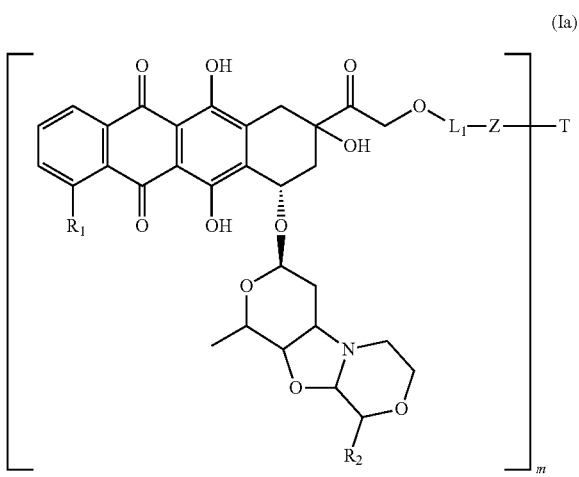
(Ia)

wherein $R_1$ is hydrogen atom, hydroxy or methoxy group and $R_2$ is a $C_1$-$C_5$ alkoxy group, or a pharmaceutically acceptable salt thereof;

$L_1$ and Z together are a linker (L) as described herein;

T is an antibody (Ab) as described herein; and m is 1 to about 20. In some embodiments, m is 1 to 10, 1 to 7, 1 to 5, or 1 to 4.

In some embodiments, $R_1$ and $R_2$ are both methoxy (—OMe).

A further nonlimiting exemplary ADC comprising nemorubicin or nemorubicin derivatives is shown in Formula Ib:

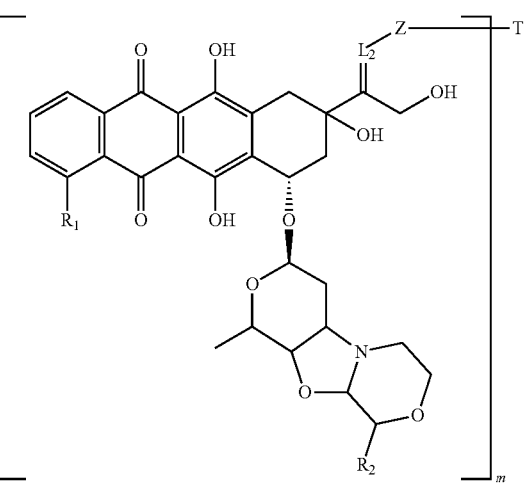
(Ib)

wherein $R_1$ is hydrogen atom, hydroxy or methoxy group and $R_2$ is a $C_1$-$C_5$ alkoxy group, or a pharmaceutically acceptable salt thereof;

$L_2$ and Z together are a linker (L) as described herein;

T is an antibody (Ab) as described herein; and m is 1 to about 20. In some embodiments, m is 1 to 10, 1 to 7, 1 to 5, or 1 to 4.

In some embodiments, $R_1$ and $R_2$ are both methoxy (—OMe).

In some embodiments, the nemorubicin component of a nemorubicin-containing ADC is PNU-159682. In some such embodiments, the drug portion of the ADC may have one of the following structures:

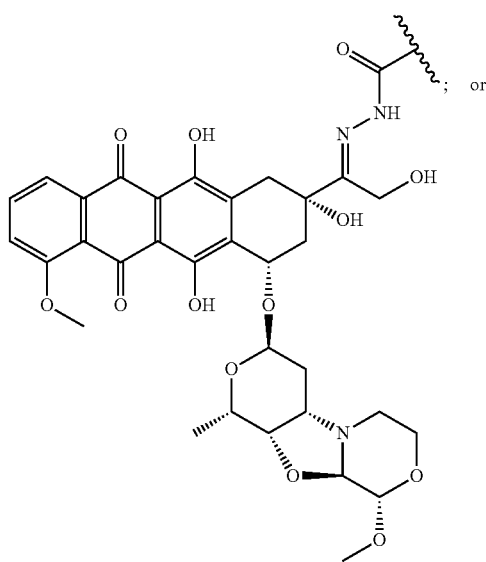

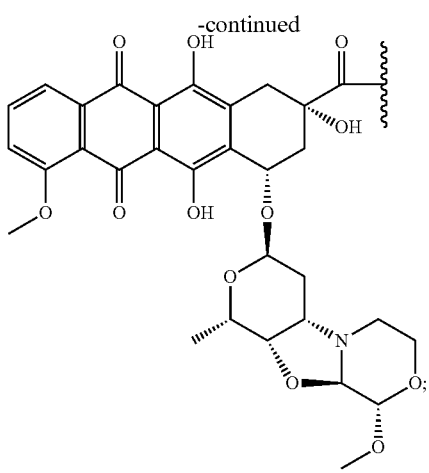

wherein the wavy line indicates the attachment to the linker (L).

Anthracyclines, including PNU-159682, may be conjugated to antibodies through several linkage sites and a variety of linkers (US 2011/0076287; WO2009/099741; US 2010/0034837; WO 2010/009124), including the linkers described herein.

Exemplary ADCs comprising a nemorubicin and linker include, but are not limited to:

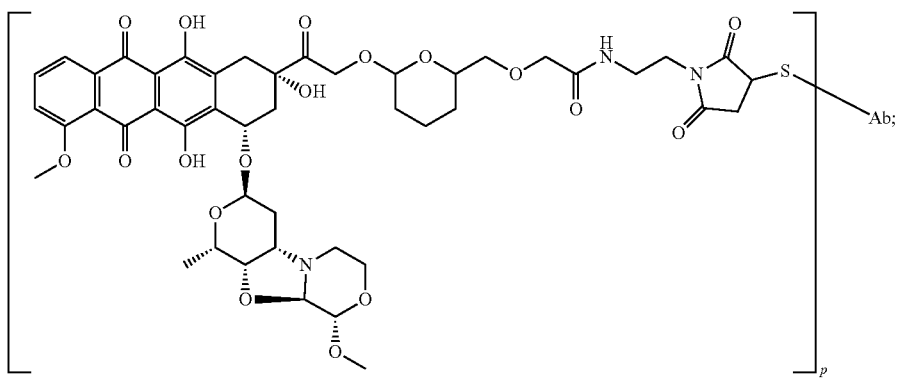

PNU-159682 maleimide acetal-Ab

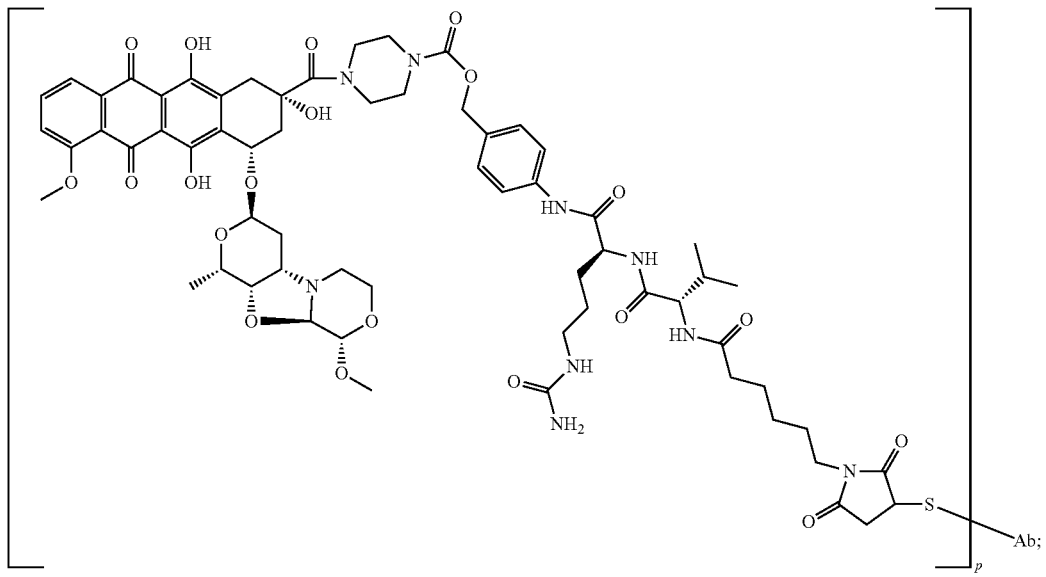

PNU-159682-val-cit-PAB-Ab

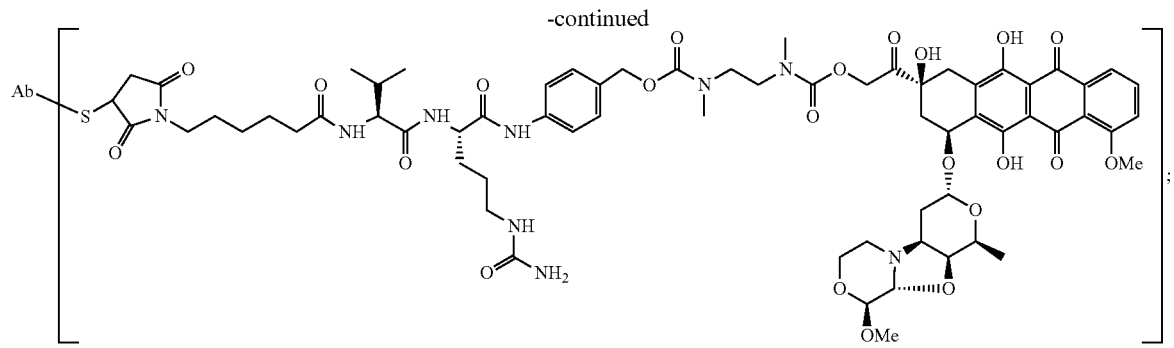

PNU-159682-val-cit-PAB-spacer-Ab

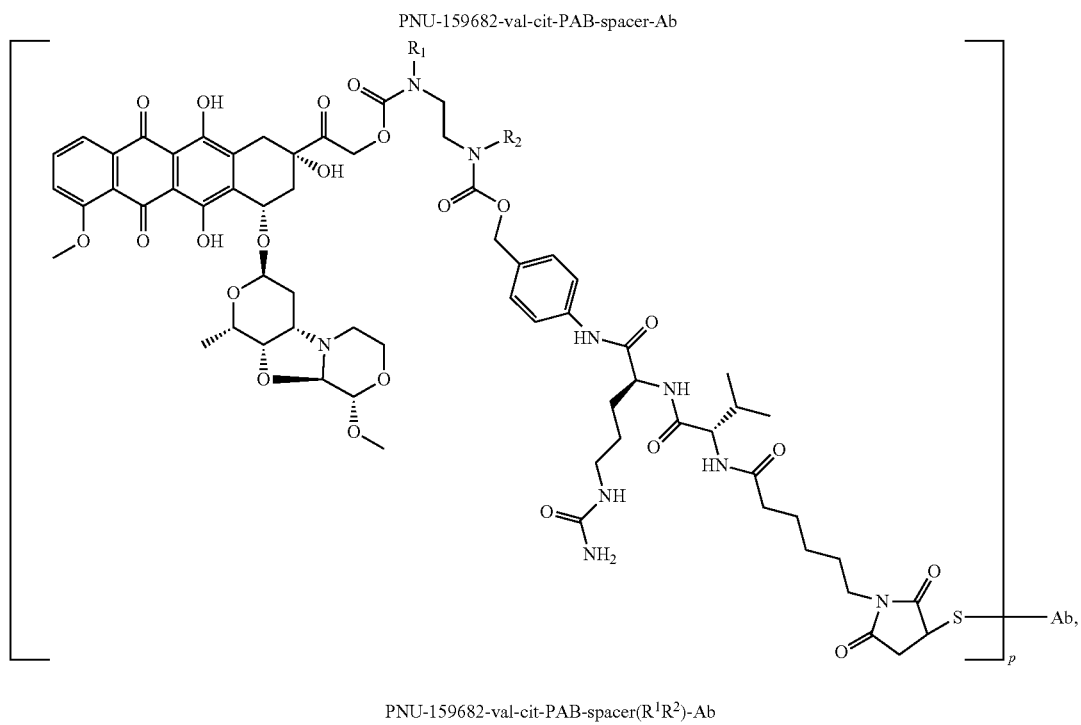

PNU-159682-val-cit-PAB-spacer($R^1R^2$)-Ab

PNU-159682-val-cit-PAB-spacer($R^1R^2$)-Ab, wherein:

$R_1$ and $R_2$ are independently selected from H and $C_1$-$C_6$ alkyl; and

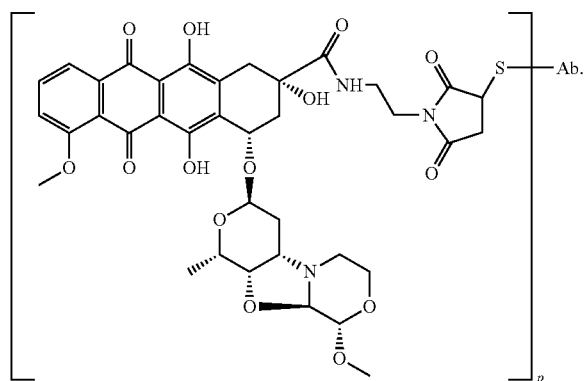

PNU-159682-maleimide-Ab

The linker of PNU-159682 maleimide acetal-Ab is acid-labile, while the linkers of PNU-159682-val-cit-PAB-Ab, PNU-159682-val-cit-PAB-spacer-Ab, and PNU-159682-val-cit-PAB-spacer($R^1R^2$)-Ab are protease cleavable.

(6) Other Drug Moieties

Drug moieties also include geldanamycin (Mandler et al (2000) *J. Nat. Cancer Inst.* 92(19):1573-1581; Mandler et al (2000) *Bioorganic & Med. Chen. Letters* 10:1025-1028; Mandler et al (2002) *Bioconjugate Chen.* 13:786-791); and enzymatically active toxins and fragments thereof, including, but not limited to, diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, e.g., WO 93/21232.

Drug moieties also include compounds with nucleolytic activity (e.g., a ribonuclease or a DNA endonuclease).

In certain embodiments, an immunoconjugate may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. In some embodiments, when an immunoconjugate is used for detection, it may comprise a radioactive atom for scintigraphic studies, for example $Tc^{99}$ or $I^{123}$, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983).

The radio- or other labels may be incorporated in the immunoconjugate in known ways. For example, a peptide may be biosynthesized or chemically synthesized using suitable amino acid precursors comprising, for example, one or more fluorine-19 atoms in place of one or more hydrogens. In some embodiments, labels such as $Tc^{99}$, $I^{123}$, $Re^{186}$, $Re^{188}$ and $In^{111}$ can be attached via a cysteine residue in the antibody. In some embodiments, yttrium-90 can be attached via a lysine residue of the antibody. In some embodiments, the IODOGEN method (Fraker et al (1978) *Biochem. Biophys. Res. Commun.* 80: 49-57 can be used to incorporate iodine-123. "Monoclonal Antibodies in Immunoscintigraphy" (Chatal, CRC Press 1989) describes certain other methods.

In certain embodiments, an immunoconjugate may comprise an antibody conjugated to a prodrug-activating enzyme. In some such embodiments, a prodrug-activating enzyme converts a prodrug (e.g., a peptidyl chemotherapeutic agent, see WO 81/01145) to an active drug, such as an anti-cancer drug. Such immunoconjugates are useful, in some embodiments, in antibody-dependent enzyme-mediated prodrug therapy ("ADEPT"). Enzymes that may be conjugated to an antibody include, but are not limited to, alkaline phosphatases, which are useful for converting phosphate-containing prodrugs into free drugs; arylsulfatases, which are useful for converting sulfate-containing prodrugs into free drugs; cytosine deaminase, which is useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), which are useful for converting peptide-containing prodrugs into free drugs; D-alanyl-carboxypeptidases, which are useful for converting prodrugs that contain D-amino acid substituents; carbohydrate-cleaving enzymes such as β-galactosidase and neuraminidase, which are useful for converting glycosylated prodrugs into free drugs; β-lactamase, which is useful for converting drugs derivatized with β-lactams into free drugs; and penicillin amidases, such as penicillin V amidase and penicillin G amidase, which are useful for converting drugs derivatized at their amine nitrogens with phenoxyacetyl or phenylacetyl groups, respectively, into free drugs. In some embodiments, enzymes may be covalently bound to antibodies by recombinant DNA techniques well known in the art. See, e.g., Neuberger et al., *Nature* 312:604-608 (1984).

c) Drug Loading

Drug loading is represented by p, the average number of drug moieties per antibody in a molecule of Formula I. Drug loading may range from 1 to 20 drug moieties (D) per antibody. ADCs of Formula I include collections of antibodies conjugated with a range of drug moieties, from 1 to 20. The average number of drug moieties per antibody in preparations of ADC from conjugation reactions may be characterized by conventional means such as mass spectroscopy, ELISA assay, and HPLC. The quantitative distribution of ADC in terms of p may also be determined. In some instances, separation, purification, and characterization of homogeneous ADC where p is a certain value from ADC with other drug loadings may be achieved by means such as reverse phase HPLC or electrophoresis.

For some antibody-drug conjugates, p may be limited by the number of attachment sites on the antibody. For example, where the attachment is a cysteine thiol, as in certain exemplary embodiments above, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the average drug loading for an ADC ranges from 1 to about 8; from about 2 to about 6; or from about 3 to about 5. Indeed, it has been shown that for certain ADCs, the optimal ratio of drug moieties per antibody may be less than 8, and may be about 2 to about 5 (U.S. Pat. No. 7,498,298).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, and for example, by: (i) limiting the molar excess of drug-linker intermediate or linker reagent relative to antibody, (ii) limiting the conjugation reaction time or temperature, and (iii) partial or limiting reductive conditions for cysteine thiol modification.

It is to be understood that where more than one nucleophilic group reacts with a drug-linker intermediate or linker reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography (see, e.g., McDonagh et al (2006) Prot. Engr. Design & Selection 19(7):299-307; Hamblett et al (2004) Clin. Cancer Res. 10:7063-7070; Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous ADC with a single loading value may be isolated from the conjugation mixture by electrophoresis or chromatography.

d) Certain Methods of Preparing Immunoconjugates

An ADC of Formula I may be prepared by several routes employing organic chemistry reactions, conditions, and reagents known to those skilled in the art, including: (1) reaction of a nucleophilic group of an antibody with a bivalent linker reagent to form Ab-L via a covalent bond, followed by reaction with a drug moiety D; and (2) reaction of a nucleophilic group of a drug moiety with a bivalent linker reagent, to form D-L, via a covalent bond, followed by reaction with a nucleophilic group of an antibody. Exemplary methods for preparing an ADC of Formula I via the latter route are described in U.S. Pat. No. 7,498,298, which is expressly incorporated herein by reference.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol) or tricarbonylethylphosphine (TCEP), such that the antibody is fully or partially reduced. Each cysteine bridge will thus form, theoretically, two reactive thiol nucleophiles. Additional nucleophilic groups can be introduced into antibodies through modification of lysine residues, e.g., by reacting lysine residues with 2-iminothiolane (Traut's reagent), resulting in conversion of an amine into a thiol. Reactive thiol groups may also be introduced into an antibody by introducing one, two, three, four, or more cysteine residues (e.g., by preparing variant antibodies comprising one or more non-native cysteine amino acid residues).

Antibody-drug conjugates of the invention may also be produced by reaction between an electrophilic group on an antibody, such as an aldehyde or ketone carbonyl group, with a nucleophilic group on a linker reagent or drug. Useful nucleophilic groups on a linker reagent include, but are not limited to, hydrazide, oxime, amino, hydrazine, thiosemicarbazone, hydrazine carboxylate, and arylhydrazide. In one embodiment, an antibody is modified to introduce electrophilic moieties that are capable of reacting with nucleophilic substituents on the linker reagent or drug. In another embodiment, the sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the antibody that can react with appropriate groups on the drug (Hermanson, Bioconjugate Techniques). In another embodiment, antibodies containing N-terminal serine or threonine residues can react with sodium meta-periodate, resulting in production of an aldehyde in place of the first amino acid (Geoghegan & Stroh, (1992) *Bioconjugate Chem.* 3:138-146; U.S. Pat. No. 5,362,852). Such an aldehyde can be reacted with a drug moiety or linker nucleophile.

Exemplary nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Nonlimiting exemplary cross-linker reagents that may be used to prepare ADC are described herein in the section titled "Exemplary Linkers." Methods of using such cross-linker reagents to link two moieties, including a proteinaceous moiety and a chemical moiety, are known in the art. In some embodiments, a fusion protein comprising an antibody and a cytotoxic agent may be made, e.g., by recombinant techniques or peptide synthesis. A recombinant DNA molecule may comprise regions encoding the antibody and cytotoxic portions of the conjugate either adjacent to one another or separated by a region encoding a linker peptide which does not destroy the desired properties of the conjugate.

In yet another embodiment, an antibody may be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a drug or radionucleotide).

E. Methods and Compositions for Diagnostics and Detection

In certain embodiments, any of the anti-LY6E antibodies provided herein is useful for detecting the presence of LY6E in a biological sample. The term "detecting" as used herein encompasses quantitative or qualitative detection. A "biological sample" comprises, e.g., a cell or tissue (e.g., biopsy material, including cancerous or potentially cancerous colon, colorectal, endometrial, pancreatic, or ovarian tissue).

In one embodiment, an anti-LY6E antibody for use in a method of diagnosis or detection is provided. In a further aspect, a method of detecting the presence of LY6E in a biological sample is provided. In certain embodiments, the method comprises contacting the biological sample with an anti-LY6E antibody as described herein under conditions permissive for binding of the anti-LY6E antibody to LY6E, and detecting whether a complex is formed between the anti-LY6E antibody and LY6E in the biological sample. Such method may be an in vitro or in vivo method. In one embodiment, an anti-LY6E antibody is used to select subjects eligible for therapy with an anti-LY6E antibody, e.g. where LY6E is a biomarker for selection of patients. In a further embodiment, the biological sample is a cell or tissue (e.g., biopsy material, including cancerous or potentially cancerous colon, colorectal, endometrial, pancreatic, or ovarian tissue).

In a further embodiment, an anti-LY6E antibody is used in vivo to detect, e.g., by in vivo imaging, A LY6E-positive cancer in a subject, e.g., for the purposes of diagnosing, prognosing, or staging cancer, determining the appropriate course of therapy, or monitoring response of a cancer to therapy. One method known in the art for in vivo detection is immuno-positron emission tomography (immuno-PET), as described, e.g., in van Dongen et al., *The Oncologist* 12:1379-1389 (2007) and Verel et al., *J. Nucl. Med.* 44:1271-1281 (2003). In such embodiments, a method is provided for detecting A LY6E-positive cancer in a subject, the method comprising administering a labeled anti-LY6E antibody to a subject having or suspected of having A LY6E-positive cancer, and detecting the labeled anti-LY6E antibody in the subject, wherein detection of the labeled anti-LY6E antibody indicates A LY6E-positive cancer in the subject. In certain of such embodiments, the labeled anti-LY6E antibody comprises an anti-LY6E antibody conjugated to a positron emitter, such as $^{68}$Ga, $^{18}$F, $^{64}$Cu, $^{86}$Y, $^{76}$Br, $^{89}$Zr, and $^{124}$I. In a particular embodiment, the positron emitter is $^{89}$Zr.

In further embodiments, a method of diagnosis or detection comprises contacting a first anti-LY6E antibody immobilized to a substrate with a biological sample to be tested for the presence of LY6E, exposing the substrate to a second anti-LY6E antibody, and detecting whether the second anti-LY6E is bound to a complex between the first anti-LY6E antibody and LY6E in the biological sample. A substrate may be any supportive medium, e.g., glass, metal, ceramic, polymeric beads, slides, chips, and other substrates. In certain embodiments, a biological sample comprises a cell or tissue (e.g., biopsy material, including cancerous or potentially cancerous colorectal, endometrial, pancreatic or ovarian tissue). In certain embodiments, the first or second anti-LY6E antibody is any of the antibodies described herein. In such embodiments, the second anti-LY6E antibody may be 6D3 or 7C9; or antibodies derived from 6D3 or 7C9 as described herein.

Exemplary disorders that may be diagnosed or detected according to any of the above embodiments include LY6E-positive cancers, such as LY6E-positive colorectal cancer (including adenocarcinoma), LY6E-positive ovarian cancer (including ovarian serous adenocarcinoma), LY6E-positive pancreatic cancer (including pancreatic ductal adenocarcinoma), and LY6E-positive endometrial cancer. In some embodiments, A LY6E-positive cancer is a cancer that receives an anti-LY6E immunohistochemistry (IHC) or in situ hybridization (ISH) score greater than "0," which corresponds to very weak or no staining in >90% of tumor cells, under the conditions described herein in Example B. In another embodiment, A LY6E-positive cancer expresses LY6E at a 1+, 2+ or 3+ level, as defined under the conditions described herein in Example B. In some embodiments, A LY6E-positive cancer is a cancer that expresses LY6E according to a reverse-transcriptase PCR (RT-PCR) assay that detects LY6E mRNA. In some embodiments, the RT-PCR is quantitative RT-PCR.

In certain embodiments, labeled anti-LY6E antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^3$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like. In another embodiment, a label is a positron emitter. Positron emitters include but are not limited to $^{68}$Ga, $^{18}$F, $^{64}$Cu, $^{86}$Y, $^{76}$Br, $^{89}$Zr, and $^{124}$I. In a particular embodiment, a positron emitter is $^{89}$Zr.

F. Pharmaceutical Formulations

Pharmaceutical formulations of an anti-LY6E antibody or immunoconjugate as described herein are prepared by mixing such antibody or immunoconjugate having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody or immunoconjugate formulations are described in U.S. Pat. No. 6,267,958. Aqueous antibody or immunoconjugate formulations include those described in U.S. Pat. No. 6,171,586 and WO2006/044908, the latter formulations including a histidine-acetate buffer.

The formulation herein may also contain more than one active ingredient as necessary for the particular indication being treated, preferably those with complementary activities that do not adversely affect each other. For example, in some instances, it may be desirable to further provide a platinum complex, e.g., for the treatment of LY6E-positive cancer such as, for example, a LY6E-positive breast cancer, or a LY6E-positive pancreatic cancer, or a LY6E-positive colon cancer, or a LY6E-positive colorectal cancer, or a LY6E-positive melanoma cancer, or a LY6E-positive ovarian cancer, or a LY6E-positive non-small cell lung cancer, or a LY6E-positive gastric cancer.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody or immunoconjugate, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-LY6E antibodies or immunoconjugates provided herein may be used in methods, e.g., therapeutic methods.

In one aspect, an anti-LY6E antibody or immunoconjugate provided herein is used in a method of inhibiting proliferation of a LY6E-positive cell, the method comprising exposing the cell to the anti-LY6E antibody or immunoconjugate under conditions permissive for binding of the anti-LY6E antibody or immunoconjugate to LY6E on the surface of the cell, thereby inhibiting the proliferation of the cell. In certain embodiments, the method is an in vitro or an in vivo method. In further embodiments, the cell is a breast cancer cell or a pancreatic cancer cell or a colon cancer cell, or a colorectal cancer cell, or a melanoma cancer cell, or an ovarian cancer cell, or a non-small cell lung cancer cell, or a gastric cancer cell.

Inhibition of cell proliferation in vitro may be assayed using the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al. (1993) *J. Immunol. Meth.* 160:81-88, U.S. Pat. No. 6,602,677. The assay may be conducted in 96- or 384-well format, making it amenable to automated high-throughput screening (HTS). See Cree et al. (1995) *AntiCancer Drugs* 6:398-404. The assay procedure involves adding a single reagent (CellTiter-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

In another aspect, an anti-LY6E antibody or immunoconjugate for use as a medicament is provided. In further aspects, an anti-LY6E antibody or immunoconjugate for use in a method of treatment is provided. In certain embodiments, an anti-LY6E antibody or immunoconjugate for use in treating LY6E-positive cancer is provided. In certain embodiments, the invention provides an anti-LY6E antibody or immunoconjugate for use in a method of treating an individual having a LY6E-positive cancer, the method comprising administering to the individual an effective amount of the anti-LY6E antibody or immunoconjugate. In one such embodiment, the method further comprises administering to the individual an effective amount of at least one additional therapeutic agent, e.g., as described below.

In a further aspect, the invention provides for the use of an anti-LY6E antibody or immunoconjugate in the manufacture or preparation of a medicament. In one embodiment, the medicament is for treatment of LY6E-positive cancer. In a further embodiment, the medicament is for use in a method of treating LY6E-positive cancer, the method comprising administering to an individual having LY6E-positive cancer an effective amount of the medicament. In one such embodiment, the method further comprises administering to the individual an effective amount of at least one additional therapeutic agent, e.g., as described below.

In a further aspect, the invention provides a method for treating LY6E-positive cancer. In one embodiment, the method comprises administering to an individual having such LY6E-positive cancer an effective amount of an anti-LY6E antibody or immunoconjugate. In one such embodiment, the method further comprises administering to the individual an effective amount of at least one additional therapeutic agent, as described below.

A LY6E-positive cancer according to any of the above embodiments may be, e.g., LY6E-positive breast cancer, or LY6E-positive pancreatic cancer, or LY6E-positive colon cancer, or LY6E-positive colorectal cancer, or LY6E-positive melanoma cancer, or LY6E-positive ovarian cancer, or LY6E-positive non-small cell lung cancer, or LY6E-positive gastric cancer. In some embodiments, a LY6E-positive cancer is a cancer that receives an anti-LY6E immunohistochemistry (IHC) or in situ hybridization (ISH) score greater than "0," which corresponds to very weak or no staining in >90% of tumor cells, under the conditions described herein. In another embodiment, a LY6E-positive cancer expresses LY6E at a 1+, 2+ or 3+ level, as defined under the conditions described herein. In some embodiments, a LY6E-positive cancer is a cancer that expresses LY6E according to a reverse-transcriptase PCR (RT-PCR) assay that detects LY6E mRNA. In some embodiments, the RT-PCR is quantitative RT-PCR.

An "individual" according to any of the above embodiments may be a human.

In a further aspect, the invention provides pharmaceutical formulations comprising any of the anti-LY6E antibodies or immunoconjugate provided herein, e.g., for use in any of the above therapeutic methods. In one embodiment, a pharmaceutical formulation comprises any of the anti-LY6E antibodies or immunoconjugates provided herein and a pharmaceutically acceptable carrier. In another embodiment, a pharmaceutical formulation comprises any of the anti-LY6E antibodies or immunoconjugates provided herein and at least one additional therapeutic agent, e.g., as described below.

Antibodies or immunoconjugates of the invention can be used either alone or in combination with other agents in a therapy. For instance, an antibody or immunoconjugate of the invention may be co-administered with at least one additional therapeutic agent. In certain embodiments, an additional therapeutic agent is a platinum complex, e.g., for the treatment of LY6E-positive cancer such as, for example, a LY6E-positive breast cancer, or a LY6E-positive pancreatic cancer, or a LY6E-positive colon cancer, or a LY6E-positive colorectal cancer, or a LY6E-positive melanoma cancer, or a LY6E-positive ovarian cancer, or a LY6E-positive non-small cell lung cancer, or a LY6E-positive gastric cancer.

Such combination therapies noted above encompass combined administration (where two or more therapeutic agents are included in the same or separate formulations), and separate administration, in which case, administration of the antibody or immunoconjugate of the invention can occur prior to, simultaneously, and/or following, administration of the additional therapeutic agent and/or adjuvant. Antibodies or immunoconjugates of the invention can also be used in combination with radiation therapy.

An antibody or immunoconjugate of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies or immunoconjugates of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody or immunoconjugate need not be, but is optionally formulated with one or more agents currently used to prevent or treat the disorder in question. The effective amount of such other agents depends on the amount of antibody or immunoconjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or immunoconjugate of the invention (when used alone or in combination with one or more other additional therapeutic agents) will depend on the type of disease to be treated, the type of antibody or immunoconjugate, the severity and course of the disease, whether the antibody or immunoconjugate is administered for preventive or therapeutic purposes, previous therapy, the patient's clinical history and response to the antibody or immunoconjugate, and the discretion of the attending physician. The antibody or immunoconjugate is suitably administered to the patient at one time or over a series of treatments. Depending on the type and severity of the disease, about 1 µg/kg to 15 mg/kg (e.g. 0.1 mg/kg-10 mg/kg) of antibody or immunoconjugate can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody or immunoconjugate would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using both an immunoconjugate of the invention and an anti-LY6E antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disorder and may have a sterile access port (for example the container may be an intravenous solution bag or a vial having a stopper pierceable by a hypodermic injection needle). At least one active agent in the composition is an antibody or immunoconjugate of the invention. The label or package insert indicates that the composition is used for treating the condition of choice. Moreover, the article of manufacture may comprise (a) a first container with a composition contained therein, wherein the composition comprises an antibody or immunoconjugate of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

I. Sequences of the Invention

In another aspect of the invention, the following sequences useful for the treatment, prevention and/or diagnosis of the disorders described above are provided.

| SEQ ID NO: | SEQUENCE | DESCRIPTION |
| --- | --- | --- |
| 1 | MKIFLPVLLAALLGVERASSLMCFSCLNQKSN LYCLKPTICSDQDNYCVTVSASAGIGNLVTFG HSLSKTCSPACPIPEGVNVGVASMGISCCQSFL CNFSAADGGLRASVTLLGAGLLLSLLPALLRFGP | HUMAN Ly6E amino acid sequence with signal sequence (amino acids 1-20, underlined) |
| 2 | MKIFLPVLLAALLGVERASSLMCFSCLNQKSN LYCLKPTICSDQDNYCVTVSTSAGIGNLVTFG HSLSKTCSPACPLPEGINVGVASMGISCCQSFL CNFSAADGGLRASATLLGAGLLLSLLPALLRFGP | CYNOMOLOGOUS Ly6E amino acid sequence with signal sequence (amino acids 1-20, underlined) |

| SEQ ID NO: | SEQUENCE | DESCRIPTION |
|---|---|---|
| 3 | DIQMTQSPSSLSASVGDRVTITCSASQGISNYLNW YQQKPGKTVKLLIYYTSNLHSGVPSRFSGSGSGT DYTLTISSLQPEDFATYYCQQYSELPWTFGQGTK VEIK | Humanized variable light chain amino acid sequence of anti-Ly6E antibody clone hu9B12 v12 |
| 4 | DIQMTQTTSSLSASLGDRVTISCSASQGISNYLNW YQQKPDGTVKLLIYYTSNLHSGVPSRFSGSGSGT DYSLTISNLEPEDIATYYCQQYSELPWTFGGGTK VEIK | Chimeric variable light chain amino acid sequence of anti-Ly6E antibody clone xLy6E mu9B12 |
| 5 | EVQLVESGPALVKPTQTLTLTCTVSGFSLTGYSVN WIRQPPGKALEWLGMIWGDGSTDYNSALKSRLTI SKDTSKNQVVLTMTNMDPVDTATYYCARDYYFN YASWFAYWGQGTLVTVSS | Humanized variable heavy chain amino acid sequence of anti-Ly6E antibody clone hu9B12 v12 |
| 6 | QVQLKESGPGLVAPSQSLSLTCTVSGFSLTGYSVN WVRQPPGKGLEWLGMIWGDGSTDYNSALKSRL TISKDNSKSQVFLKMNSLQTDDTARYYCARDYY FNYASWFAYWGPGTLVTVSA | Chimeric variable heavy chain amino acid sequence of anti-Ly6E antibody clone xLy6E mu9B12 |
| 7 | SASQGISNYLN | Humanized variable light chain CDR 1 amino acid sequence of anti-Ly6E antibody clone hu9B12 v12 |
| 8 | YTSNLHS | Humanized variable light chain CDR 2 amino acid sequence of anti-Ly6E antibody clone hu9B12 v12 |
| 9 | QQYSELPWT | Humanized variable light chain CDR 3 amino acid sequence of anti-Ly6E antibody clone hu9B12 v12 |
| 10 | GFSLTGYSVN | Humanized variable heavy chain CDR 1 amino acid sequence of anti-Ly6E antibody clone hu9B12 v12 |
| 11 | MIWGDGSTDYNSALKS | Humanized variable heavy chain CDR 2 amino acid sequence of anti-Ly6E antibody clone hu9B12 v12 |
| 12 | DYYFNYASWFAY | Humanized variable heavy chain CDR 3 amino acid sequence of anti-Ly6E antibody clone hu9B12 v12 |
| 13 | SASQGISNYLN | Chimeric variable light chain CDR 1 amino acid sequence of anti-Ly6E antibody clone xLy6E mu9B12 |
| 14 | YTSNLHS | Chimeric variable light chain CDR 2 amino acid sequence of anti-Ly6E antibody clone xLy6E mu9B12 |
| 15 | QQYSELPWT | Chimeric variable light chain CDR 3 amino acid sequence of anti-Ly6E antibody clone xLy6E mu9B12 |
| 16 | GFSLTGYSVN | Chimeric variable heavy chain CDR 1 amino acid sequence of anti-Ly6E antibody clone xLy6E mu9B12 |
| 17 | MIWGDGSTDYNSALKS | Chimeric variable heavy chain CDR 2 amino acid sequence of anti-Ly6E antibody clone xLy6E mu9B12 |

-continued

| SEQ ID NO: | SEQUENCE | DESCRIPTION |
| --- | --- | --- |
| 18 | DYYFNYASWFAY | Chimeric variable heavy chain CDR 3 amino acid sequence of anti-Ly6E antibody clone xLy6E mu9B12 |
| 19 | DIQMTQSPSSLSASVGDRVTITC | Humanized variable light chain FW 1 amino acid sequence of anti-Ly6E antibody clone hu9B12 v12 |
| 20 | WYQQKPGKTVKLLIY | Humanized variable light chain FW 2 amino acid sequence of anti-Ly6E antibody clone hu9B12 v12 |
| 21 | GVPSRFSGSGSGTDYTLTISSLQPEDFATYYC | Humanized variable light chain FW 3 amino acid sequence of anti-Ly6E antibody clone hu9B12 v12 |
| 22 | FGQGTKVEIK | Humanized variable light chain FW 4 amino acid sequence of anti-Ly6E antibody clone hu9B12 v12 |
| 23 | EVQLVESGPALVKPTQTLTLTCTVS | Humanized variable heavy chain FW 1 amino acid sequence of anti-Ly6E antibody clone hu9B12 v12 |
| 24 | WIRQPPGKALEWLG | Humanized variable heavy chain FW 2 amino acid sequence of anti-Ly6E antibody clone hu9B12 v12 |
| 25 | RLTISKDTSKNQVVLTMTNMDPVDTATYYCAR | Humanized variable heavy chain FW 3 amino acid sequence of anti-Ly6E antibody clone hu9B12 v12 |
| 26 | WGQGTLVTVSS | Humanized variable heavy chain FW 4 amino acid sequence of anti-Ly6E antibody clone hu9B12 v12 |
| 27 | DIQMTQTTSSLSASLGDRVTISC | Chimeric variable light chain FW 1 amino acid sequence of anti-Ly6E antibody clone xLy6E mu9B12 |
| 28 | WYQQKPDGTVKLLIY | Chimeric variable light chain FW 2 amino acid sequence of anti-Ly6E antibody clone xLy6E mu9B12 |
| 29 | GVPSRFSGSGSGTDYSLTISNLEPEDIATYYC | Chimeric variable light chain FW 3 amino acid sequence of anti-Ly6E antibody clone xLy6E mu9B12 |
| 30 | FGGGTKVEIK | Chimeric variable light chain FW 4 amino acid sequence of anti-Ly6E antibody clone xLy6E mu9B12 |
| 31 | QVQLKESGPGLVAPSQSLSLTCTVS | Chimeric variable heavy chain FW 1 amino acid sequence of anti-Ly6E antibody clone xLy6E mu9B12 |
| 32 | WVRQPPGKGLEWLG | Chimeric variable heavy chain FW 2 amino acid sequence of anti-Ly6E antibody clone xLy6E mu9B12 |

-continued

| SEQ ID NO: | SEQUENCE | DESCRIPTION |
| --- | --- | --- |
| 33 | RLTISKDNSKSQVFLKMNSLQTDDTARYYCAR | Chimeric variable heavy chain FW 3 amino acid sequence of anti-Ly6E antibody clone xLy6E mu9B12 |
| 34 | WGPGTLVTVSA | Chimeric variable heavy chain FW 4 amino acid sequence of anti-Ly6E antibody clone xLy6E mu9B12 |
| 35 | <u>MKIFLPVLLAALLGVERASS</u>LMCFSCLNQKSNL YCLKPTICSDQDNYCVTVSTSAGIGNLVTFGHS LSKTCSPACPLPEGINVGVASMGISCCQSFLCNF SAADGGLRASATLLGAGLLLSLLPALLRFGP | RHESUS Ly6E amino acid sequence with signal sequence (amino acids 1-20, underlined) |
| 36 | <u>MSATSNMRVFLPVLLAALLGMEQVHS</u>LMCFSC TDQKNNINCLWPVSCQEKDHYCITLSAAAGFG NVNLGYTLNKGCSPICPSENVNLNLGVASVNSY CCQSSFCNFSAAGLGLRASIPLLGLGLLLSLLALL QLSP | MOUSE Ly6E amino acid sequence with signal sequence (amino acids 1-26, underlined) |
| 37 | <u>MSAASSMRVFLPVLLAALLGVEQVHS</u>LMCFSCTD QKNNINCLWPVSCSSTDNYCITLSAAAGFGNVNL GYTLNKGCSPTCPRENININLGVASVNSYCCQSSF CNFSTAGLGLRASIPLLGLGLLLSLLAVLRLSP | RAT Ly6E amino acid sequence with signal sequence (amino acids 1-26, underlined) |
| 38 | LMCFSCLNQKSNLYCLKPTICSDQDNYCVTVSA SAGIGNLVTFGHSLSKTCSPACPIPEGVNVGVAS MGISCCQSFLCNFSAADGGLRASVTLLGAGLLL SLLPALLRFGP | Mature HUMAN Ly6E amino acid sequence (without signal sequence) |
| 39 | LMCFSCLNQKSN LYCLKPTICSDQDNYCVTVSTSAGIGNLVTFG HSLSKTCSPACPLPEGINVGVASMGISCCQSFL CNFSAADGGLRASATLLGAGLLLSLLPALLRFGP | Mature CYNOMOLOGOUS Ly6E amino acid sequence (without signal sequence) |
| 40 | LMCFSCLNQKSNL YCLKPTICSDQDNYCVTVSTSAGIGNLVTFGHS LSKTCSPACPLPEGINVGVASMGISCCQSFLCNF SAADGGLRASATLLGAGLLLSLLPALLRFGP | Mature RHESUS Ly6E amino acid sequence (without signal sequence) |
| 41 | LMCFSC TDQKNNINCLWPVSCQEKDHYCITLSAAAGFG NVNLGYTLNKGCSPICPSENVNLNLGVASVNSY CCQSSFCNFSAAGLGLRASIPLLGLGLLLSLLALL QLSP | Mature MOUSE Ly6E amino acid sequence (without signal sequence) |
| 42 | LMCFSCTD QKNNINCLWPVSCSSTDNYCITLSAAAGFGNVNL GYTLNKGCSPTCPRENININLGVASVNSYCCQSSF CNFSTAGLGLRASIPLLGLGLLLSLLAVLRLSP | Mature RAT Ly6E amino acid sequence (without signal sequence) |
| 43 | EVQLVESGGGLVQPGGSLRLSCAASGFSLTGYSVN WVRQAPGKGLEWVGMIWDGSTDYNSALKSRFT ISRDNSKNTLYLQMNSLRAEDTAVYYCARDYYFN YASWFAYWGQGTLVTVSS | Humanized variable heavy chain amino acid sequence of hu9B12 VH3 graft |
| 44 | QVQLKESGPGLVAPSQSLSLTCTVSGFSLTGYSVN WVRQPPGKGLEWLGMIWDGSTDYNSALKSRLT ISKDNSKSQVFLKMNSLQTDDTARYYCARDYYFN YASWFAYWGPGTLVTVSA | Chimeric variable heavy chain amino acid sequence of xLy6E mu9B12 in VH3 graft |
| 45 | DIQMTQSPSSLSASVGDRVTITCRASQGISSYLAWY QQKPGKAPKLLIYAASSLQSGVPSRFSGSGSGTDFT LTISSLQPEDFATYYCQQYYSYPFTFGQGTKVEIK | Human kappa I consensus light chain variable amino acid sequence |
| 46 | EVQLVESGPALVKPTQTLTLTCTFSGFSLSTSGVG VSWIRQPPGKALEWLALIDWNDDKRYSTSLKSRL TISKDTSKNQVVLTMTNMDPVDTATYYCARDTA AYFDYWGQGTLVTVSS | Human VH2 consensus heavy chain variable amino acid sequence |
| 47 | EVQLVESGGGLVQPGGSLRLSCAASGFTFSSYAMS WVRQAPGKGLEWVGAISSSGSSTYYADSVKGRFT ISRDNSKNTLYLQMNSLRAEDTAVYYCARFDYWG QGTLVTVSS | Human VH3 consensus heavy chain variable amino acid sequence |

III. Examples

The following are examples of methods and compositions of the invention. It is understood that various other embodiments may be practiced, given the general description provided above.

Example 1—Human Ly6E Gene Expression

GeneLogic Profile: For the analysis of Ly6E mRNA expression in multiple human tumor and normal biopsy samples, the Affymetrix data were obtained from Gene Logic Inc. The analysis shown for probe set ID 202145_at was carried out using the HGU133 Plus v2 GeneChip on 3,879 normal human tissue samples (green symbols), 1,605 human cancer tissue samples (red symbols: 1,291 primary and 314 metastatic), and 3,872 human noncancer disease tissue samples (blue symbols). Microarray data were normalized using the Affymetrix MAS (Microarray Analysis Suite) version 5.0 software, with sample expression values scaled to a trimmed mean of 500.

This analysis showed that Ly6E was specifically overexpressed in breast, pancreatic, colon, lung and ovarian cancers with low/no detection of Ly6E in normal tissues (FIG. 2).

In Situ Hybridization (ISH): In situ hybridization was performed on ovarian cancer tissue microarray (TMA) for evaluating prevalence of Ly6E per methods established in Methods Mol Biol. 2006; 326:255-64.

```
Forward primer
                                      SEQ ID NO: 48
GTG CCT GAT CTG TGC CCT TGG Reverse primer
                                      SEQ ID NO: 49
CCC GGA AGT GGC AGA AAC CC Probe sequence:
                                      SEQ ID NO: 50
GTGCCTGATCTGTGCCCTTGGTCCCAGGTCAGGCCCACCCCCTGCACCTC

CACCTGCCCCAGCCCCTGCCTCTGCCCAAGTGGGCCAGCTGCCCTCACTT

CTGGGGTGGATGATGTGACCTTCCTTGGGGGACTGCGGAAGGGACGAGGG

TTCCCTGGAGTCTTACGGTCCAACATCAGACCAAGTCCCATGGACATGCT

GACAGGGTCCCCAGGGAGACCGTGTCAGTAGGGATGTGTGCCTGGCTGTG

TACGTGGGTGTGCAGTGCACGTGAGAGCACGTGGCGGCTTCTGGGGGCCA

TGTTTGGGGAGGGAGGTGTGCCAGCAGCCTGGAGAGCCTCAGTCCCTGTA

GCCCCCTGCCCTGGCACAGCTGCATGCACTTCAAGGGCAGCCTTTGGGGG

TTGGGGTTTCTGCCACTTCCGGG.
```

The results indicated that 47/65 (72%) of ovarian tumors analyzed showed Ly6E expression (data not shown).

Immunohistochemistry (IHC): Immunohistochemistry was performed on 4 μm thick formalin-fixed paraffin embedded (FFPE) tissue sections mounted on glass slides. Slides were deparaffinized in xylene and rehydrated through graded alcohols to distilled water. Slides were pretreated with Target Retrieval solution (Dako, Carpinteria, Calif., USA) for 20 minutes at 99° C. Slides were then treated with KPL blocking solution (Kierkegaard and Perry Laboratories, Gaithersburg, Md., USA) and avidin/biotin block (Vector Laboratories, Burlingame, Calif., USA) respectively. Nonspecific IgG binding was blocked with 10% horse serum (Life Technologies, Carlsbad, Calif., USA) in 3% bovine serum albumin (Roche, Basel, Switzerland) in phosphate buffered saline. Primary antibody, mouse anti-Ly6E, clone 10G7.7.8 (see Example 3) was diluted 10 μg/mL and incubated on slides for 60 minutes at room temperature.

Slides were rinsed, incubated with horse anti-mouse IgG biotinylated secondary (Vector Labs) followed by incubation in Vectastain ABC Elite reagent (Vector Labs). Slides were then incubated in Pierce metal enhanced DAB (Thermo Scientific; Fremont, Calif.), counterstained, dehydrated and coverslipped.

From IHC studies, the prevalence of Ly6E was detected at 27-36% in breast cancer, ~40% in pancreatic cancer, ~26% in colon cancer, 17-26% in melanoma, ~29% in NSCLC (data not shown).

Immunohistochemistry on Normal Tissues: On a panel of normal human and cynomolgus monkey tissues, low and moderate Ly6E expression is detected in the stomach and salivary glands of both human and cynomolgus monkey, low to moderate Ly6E expression is detected in a subpopulation of cells in the adrenal cortex in cynomolgus monkey and to a lesser extent in human specimens and moderate expression of Ly6E is detected in the transitional epithelium of the urinary bladder (only cynomolgus monkey was examined). Table 2 below tabulates immunohistochemical (IHC) expression of Ly6E in a comprehensive human and cynomolgus monkey normal tissue panel. Low (LOW) to moderate (MOD) Ly6E expression is limited to the underlined tissues (adrenal cortex, cervix, salivary glands, stomach and urinary bladder). ND=not done. NO=no expression.

TABLE 2

| Normal Tissue | Human | Cyno |
| --- | --- | --- |
| Abdominal Cavity | ND | NO |
| Adrenal | LOW (1/3) | MOD |
| Bone Marrow | NO | NO |
| Brain | NO | NO |
| Breast | NO | NO |
| Cervix | MOD (1/3) | NO |
| Colon | NO | NO |
| Esophagus | NO | NO |
| Eye | NO | NO |
| Heart | NO | NO |
| Intestine Small | NO | NO |
| Kidney | NO | NO |
| Larynx | NO | NO |
| Liver | NO | NO |
| Lung | NO | NO |
| Pancreas | NO | NO |
| Parathyroid | NO | ND |
| Pituitary | ND | NO |
| Prostate | NO | NO |
| Salivary Gland | MOD | MOD |
| Skeletal Muscle | NO | NO |
| Skin | NO | NO |
| Spleen | NO | NO |
| Stomach | LOW | LOW |
| Testis | NO | NO |
| Thymus | NO | NO |
| Thyroid | NO | NO |
| Tonsil | NO | NO |
| Urinary Bladder | ND | MOD |
| Uterus | NO | NO |

Example 2—Quantitative PCR (QRT PCR)

Human major tissue qPCR Array containing 1st strand DNA from a panel of 48 normal tissues from Origene, Rockville, Md. (HMRT 102) was assayed for Ly6E RNA expression. Ly6E expression in a panel of select cancer cell lines and tissues (breast and pancreatic) were assayed in parallel. Taqman assays were set up using reagents, instrumentation and software from Applied Biosystems (ABI, Foster City, Calif.). Primer-probe sets were designed with primers flanking a fluorogenic probe dual labeled with Reporter dye FAM and quencher dye TAMRA.

```
Primer-probe set for RPL19:
Forward primer-
                                    (SEQ ID NO: 51)
5' AGC GGA TTC TCA TGG AAC A;

Reverse primer-
                                    (SEQ ID NO: 52)
5' CTG GTC AGC CAG GAG CTT
and probe-
                                    (SEQ ID NO: 53)
5' TCC ACA AGC TGA AGG CAG ACA AGG.

Primer-probe set for Ly6E:
Forward primer-
                                    (SEQ ID NO: 54)
5' AGA AGG CGT CAA TGT TGG T;

Reverse primer-
                                    (SEQ ID NO: 55)
5' CAC TGA AAT TGC ACA GAA AGC
and probe-
                                    (SEQ ID NO: 56)
5' TTC CAT GGG CAT CAG CTG CTG.
```

Figure 3:
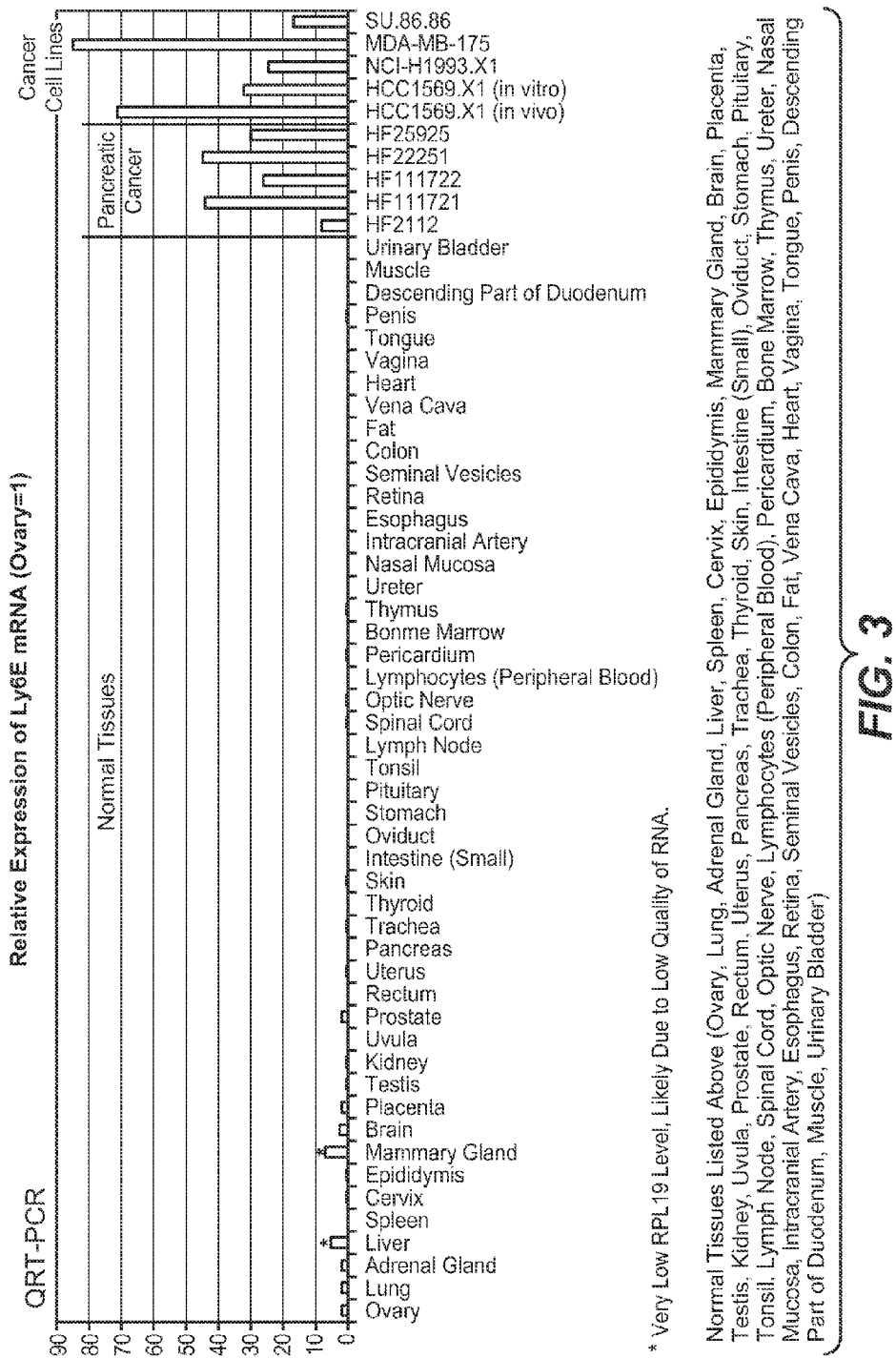
FIG. 3 a depicts QRT-PCR relative fold change in Ly6E transcript expression normalized to expression of RPL19 control gene in a panel of normal human tissues and select cancer cell lines and tissues as described in Example 2. The results indicate that the Ly6E transcript expression in normal tissues is low compared to expression of Ly6E in breast and pancreatic cancers.
Figure 7A:
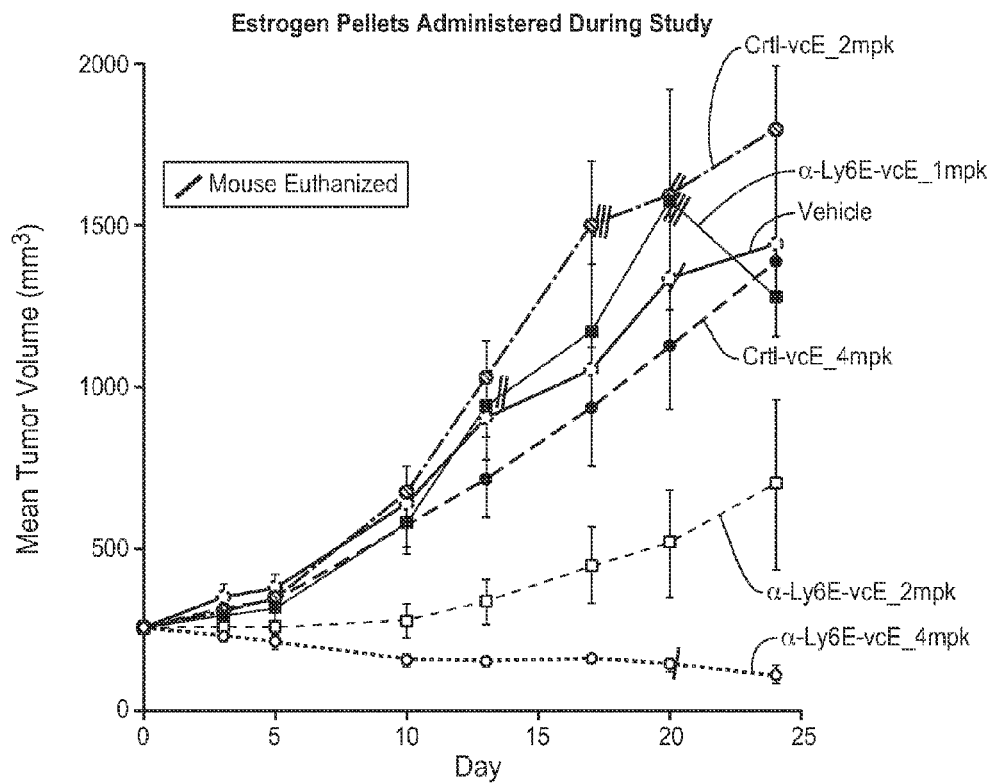
FIG. 7 the in vivo efficacy of an anti-Ly6E ADC in a xenograft mouse model as described in Example 7. Panel A shows subcutaneous tumors established in immunodeficient mice inoculated with HCC1569 X2 breast cancer cells. When tumor volumes reached approximately 100-250 mm³ (day 0), animals were given a single IV injection of either control ADC (Control-vc-MMAE) or a humanized anti-Ly6E (hu9B12 v12) ADC (MC-vc-PAB-MMAE) at the indicated doses. Average tumor volumes with standard deviations were determined from 9 animals per groups (indicated on graph). Panel B shows surface Ly6E protein expression in live HCC1569 X2 cells as seen by flow cytometry, where the gray peak indicates cells treated to secondary detection reagent alone and the black peak indicates cells treated with 3 µg/mL Ly6E antibody (hu9B12 v12) ADC followed by treatment with Alexafluor 488 conjugated to Human IgG as a secondary detection reagent. Expression of Ly6E as a GeoMean value is shown to the right of the histogram. Panel C shows cell killing by hu9B12 v12 ADC titration for the breast cancer cell line HCC1569 X2. The indicated concentrations of hu9B12 v12 ADC, control IgG-vc-MMAE, or equivalent amount of PBS vehicle control were incubated with cells for 5 days and relative cell viability (y-axis) assessed using CellTiter-Glo.
Figure 7B:
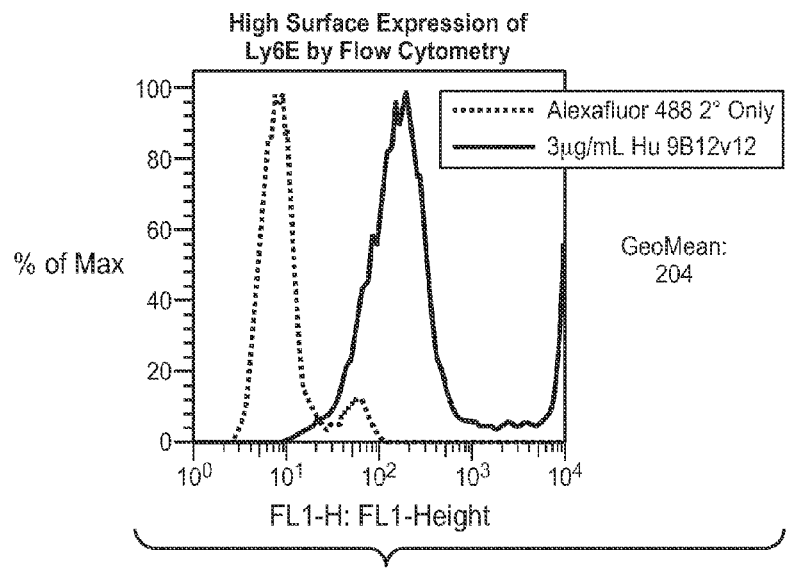
Figure 7C:
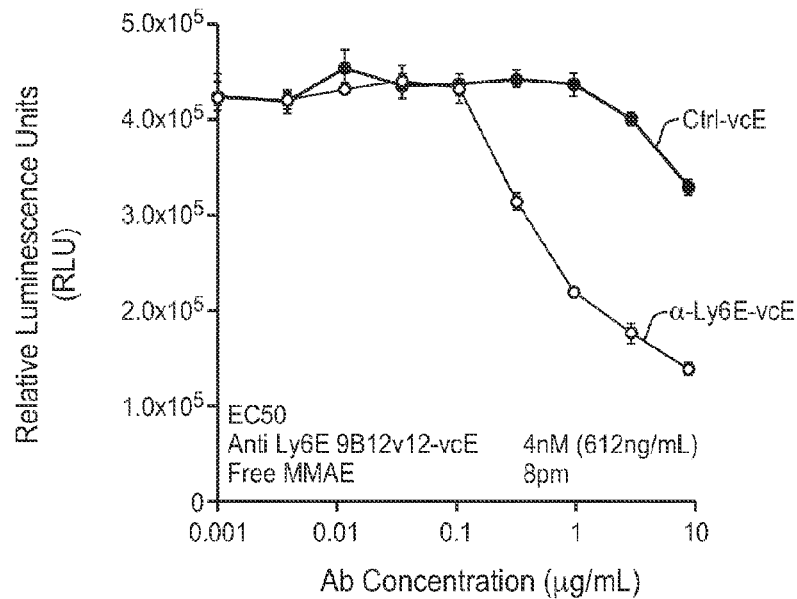
Figure 8A:
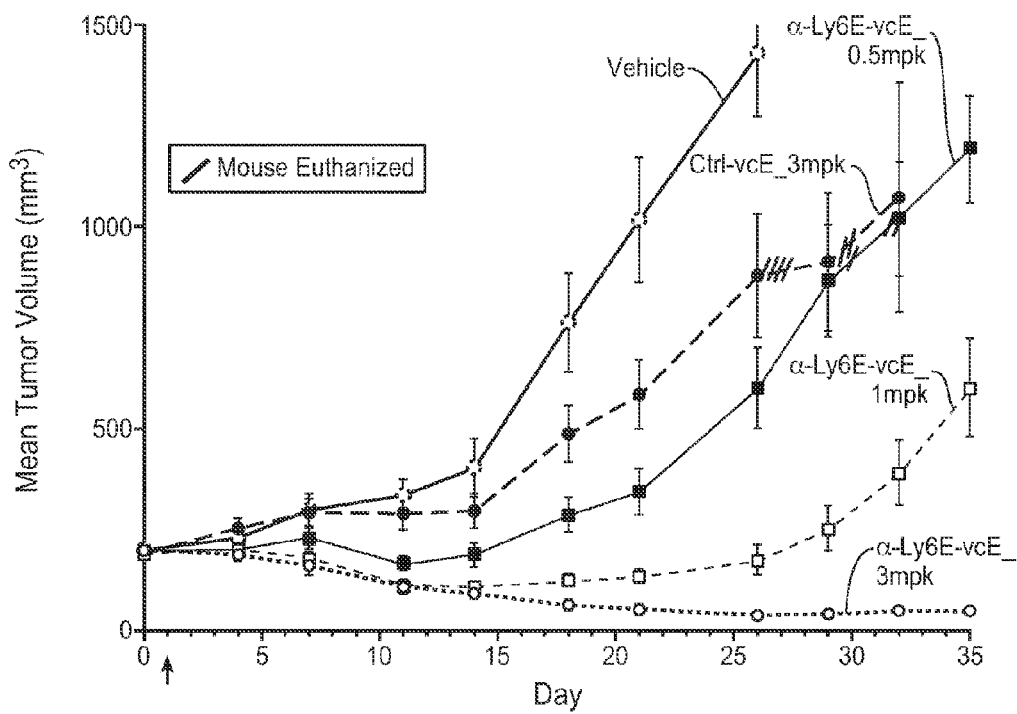
FIG. 8 shows the in vivo efficacy of an anti-Ly6E ADC in a xenograft mouse model. Panel A shows subcutaneous tumors established in immunodeficient mice inoculated with SU.86.86 pancreatic cancer cells. When tumor volumes reached approximately 100-250 mm³ (day 0), animals were given a single IV injection of either control ADC (Control-vc-MMAE) or anti-Ly6E ADC at the indicated doses. Average tumor volumes with standard deviations were determined from 9 animals per groups (indicated on graph). Panel B compares total Ly6E protein expression in HCC1569 X1 and SU.86.86 cell lysates by immunoblotting. Total β-Actin protein levels were measured in parallel to serve as loading controls. Panel C shows cell killing by anti-Ly6E ADC titration for the pancreatic cancer cell line SU.86.86. The indicated concentrations of anti-Ly6E ADC, control IgG-vc-MMAE, or equivalent amount of PBS vehicle control were incubated with cells for 5 days and relative cell viability (y-axis) assessed using CellTiter-Glo. Panel D shows 1+Ly6E staining on SU.86.86 cell pellet by immunohistochemistry.
Figure 9A:
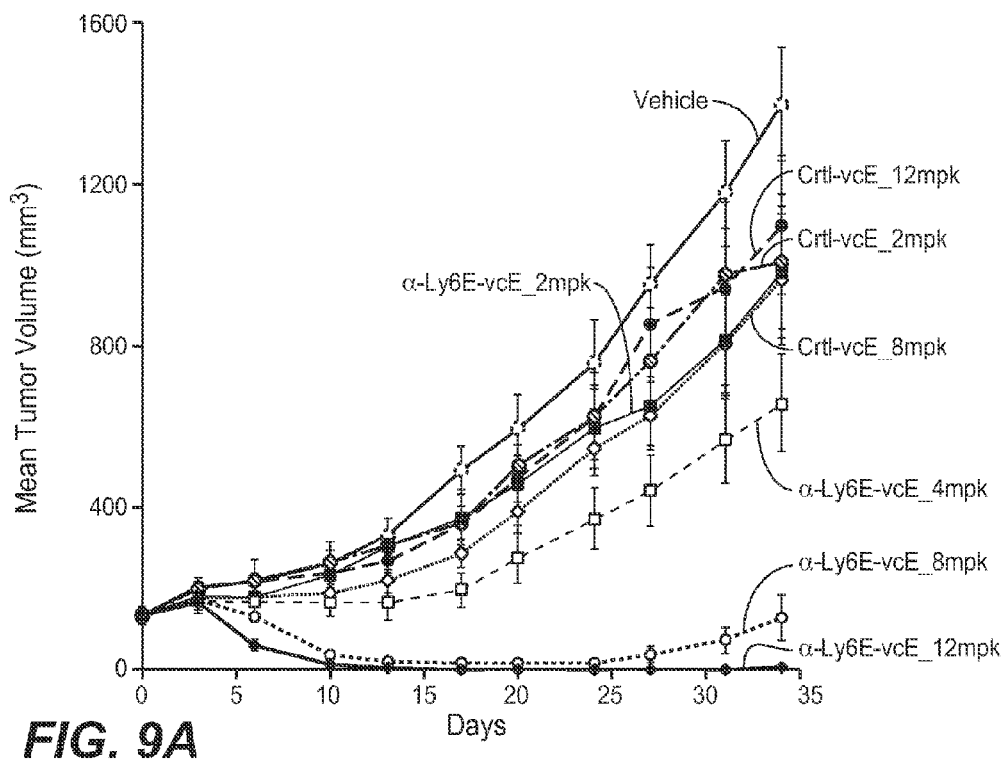
FIG. 9 shows the in vivo efficacy of anti-Ly6E ADC in primary breast cancer tumor xenograft model HBCx-9 established at XenTech (Evry, France). Panel A shows subcutaneous tumors established in immunodeficient mice implanted with patient derived breast cancer tumor material. When tumor volumes reached approximately 100-250 mm³ (day 0), animals were given a single IV injection of either control ADC (Control-vc-MMAE) or anti-Ly6E ADC at the indicated doses. Average tumor volumes with standard deviations were determined from 9 animals per groups (indicated on graph). Panel B compares total Ly6E protein expression in various XenTech primary tumor models and in HCC1569 X1 and SU.86.86 cell lysates by immunoblotting. Total β-Actin protein levels were measured in parallel to serve as loading controls. Panel C shows Ly6E staining on HBCx-9 tumors by immunohistochemistry. Independent staining of multiple tumor samples showed heterogeneous staining patterns. The percent of tumor cells staining at a 1+ level for Ly6E is indicated.
Figure 9B:
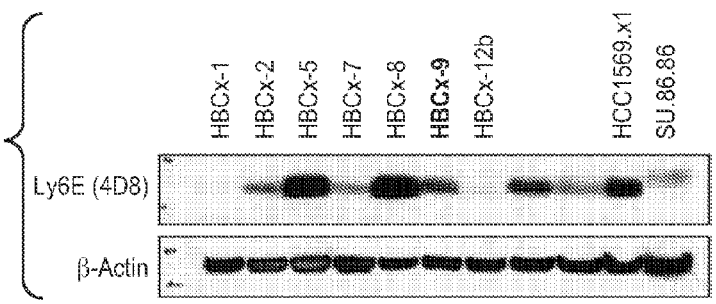
Figure 9C:
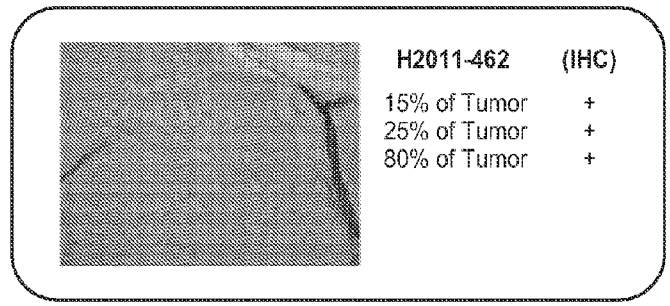
Figure 10A:
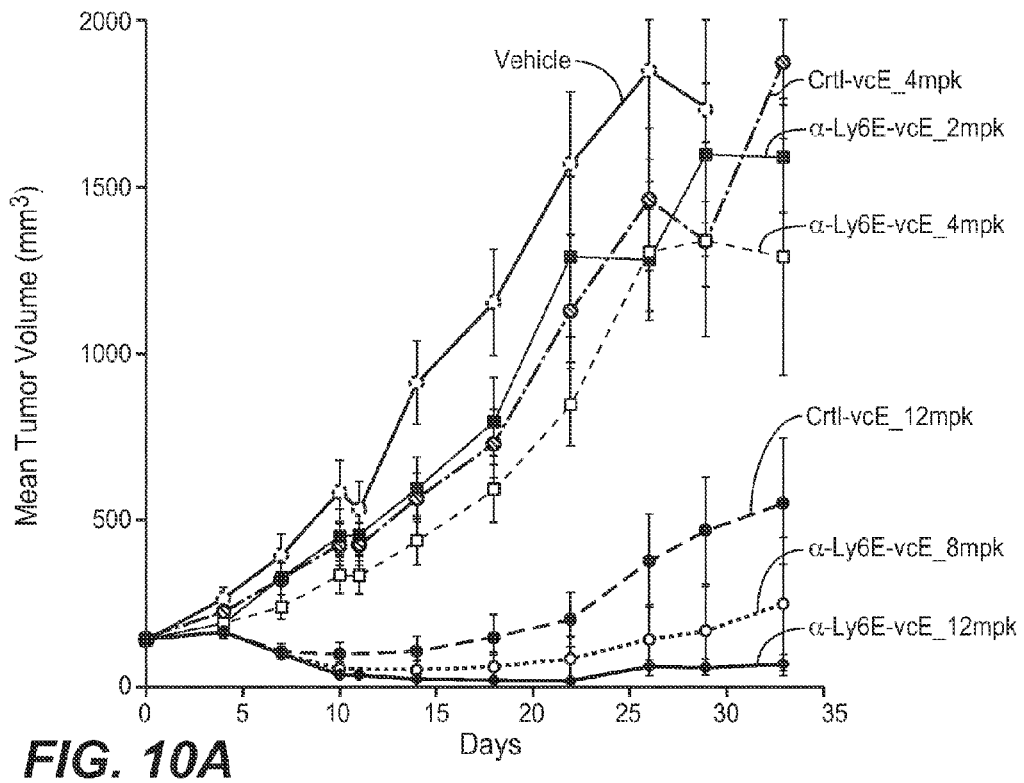
FIG. 10 shows the in vivo efficacy of anti-Ly6E ADC in primary breast cancer tumor xenograft model HBCx-8 established at XenTech (Evry, France). Panel A shows subcutaneous tumors established in immunodeficient mice implanted with patient derived breast cancer tumor material. When tumor volumes reached approximately 100-250 mm³ (day 0), animals were given a single IV injection of either control ADC (Control-vc-MMAE) or anti-Ly6E ADC at the indicated doses. Average tumor volumes with standard deviations were determined from 10 animals per groups (indicated on graph). Panel B compares total Ly6E protein expression in various XenTech primary tumor models and in HCC1569 X1 and SU.86.86 cell lysates by immunoblotting. Total β-Actin protein levels were measured in parallel to serve as loading controls. Panel C shows Ly6E staining on HBCx-8 tumors by immunohistochemistry. Independent staining of multiple tumor samples showed heterogeneous staining patterns at a 1+ or 2+ level.
Figure 10B:
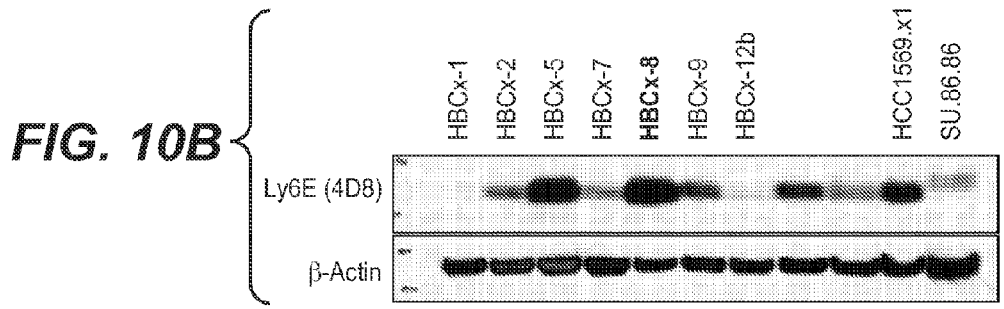
Figure 10C:
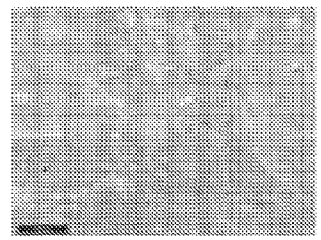
Figure 11A:
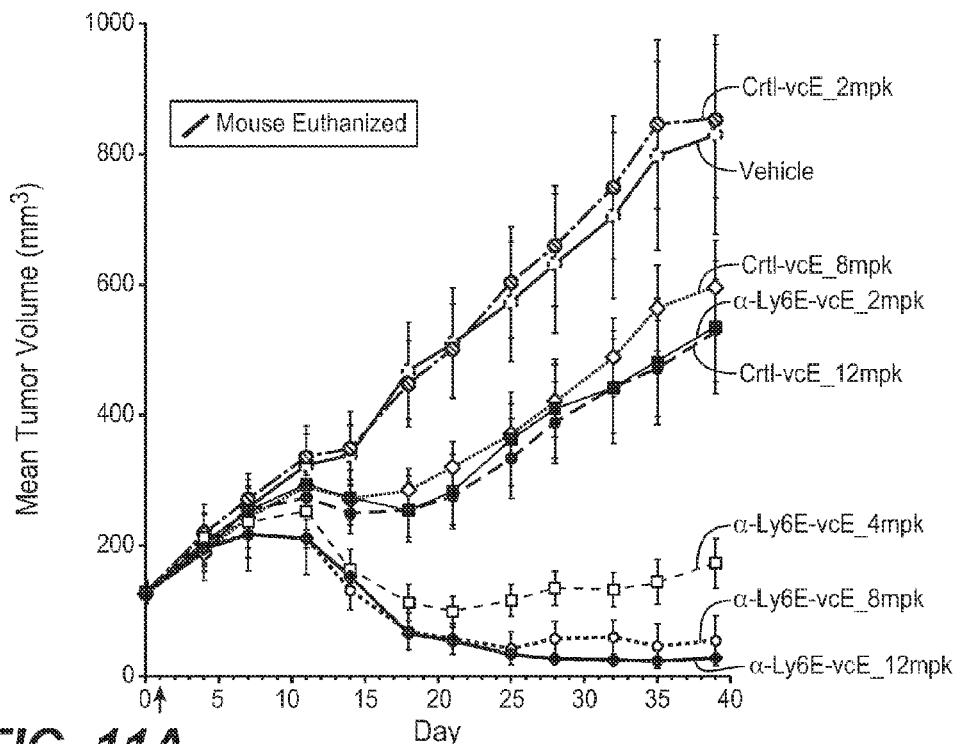
FIG. 11 shows: the in vivo efficacy of anti-Ly6E ADC in primary breast cancer tumor xenograft model MAXF-1162 established at Oncotest GmbH (Freiburg, Germany). Panel A shows subcutaneous tumors established in immunodeficient mice implanted with patient derived breast cancer tumor material. When tumor volumes reached approximately 100-250 mm³ (day 0), animals were given a single IV injection of either control ADC (Control-vc-MMAE) or anti-Ly6E ADC at the indicated doses. Average tumor volumes with standard deviations were determined from 10 animals per groups (indicated on graph). Panel B compares total Ly6E protein expression in various Oncotest primary tumor models and cell lysates by immunoblotting. Total GAPDH protein levels were measured in parallel to serve as loading controls. Panel C shows Ly6E staining on MAXF-1162 tumors by immunohistochemistry. Independent staining of multiple tumor samples showed heterogeneous staining patterns. The percent of tumor cells staining at a 1+ or 2+ level for Ly6E is indicated.
Figure 11B:
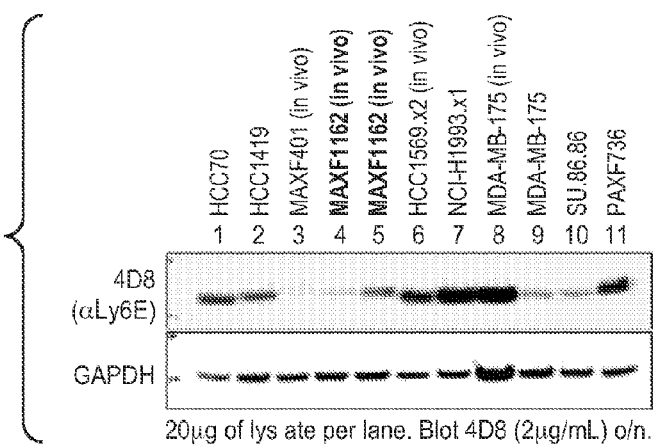
Figure 11C:
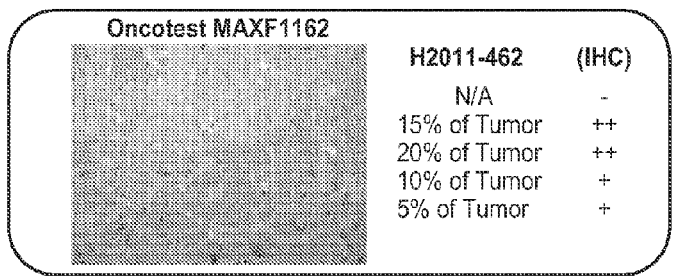
Figure 12A:
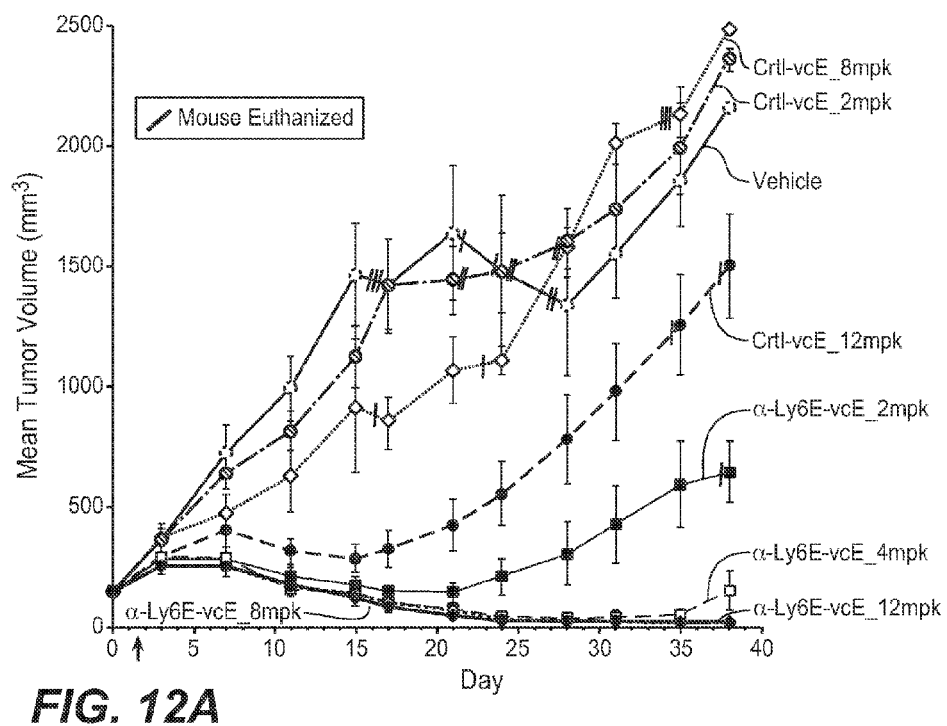
FIG. 12 shows the in vivo efficacy of anti-Ly6E ADC in primary pancreatic cancer tumor xenograft model PAXF-1657 established at Oncotest GmbH (Freiburg, Germany). Panel A shows subcutaneous tumors established in immunodeficient mice with patient derived pancreatic cancer tumor explants. When tumor volumes reached approximately 100-250 mm³ (day 0), animals were given a single IV injection of either control ADC (Control-vc-MMAE) or anti-Ly6E ADC at the indicated doses. Average tumor volumes with standard deviations were determined from 10 animals per groups (indicated on graph). Panel B compares total Ly6E protein expression in various Oncotest primary tumor models and cell lysates by immunoblotting. Total GAPDH protein levels were measured in parallel to serve as loading controls. Panel C shows Ly6E staining on PAXF-1657 tumors by immunohistochemistry. Independent staining of multiple tumor samples showed heterogeneous staining patterns. The percent of tumor cells staining at a very weak (+/−) level for Ly6E is indicated.
Figure 12B:
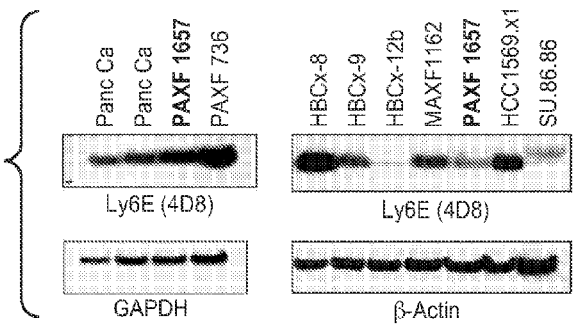
Figure 12C:
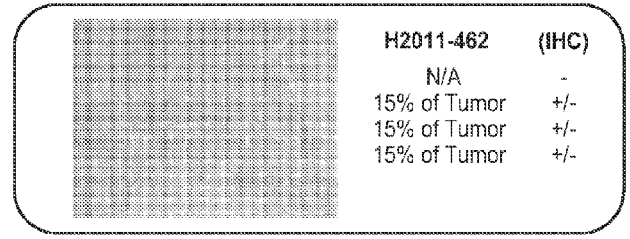
Figure 13A:
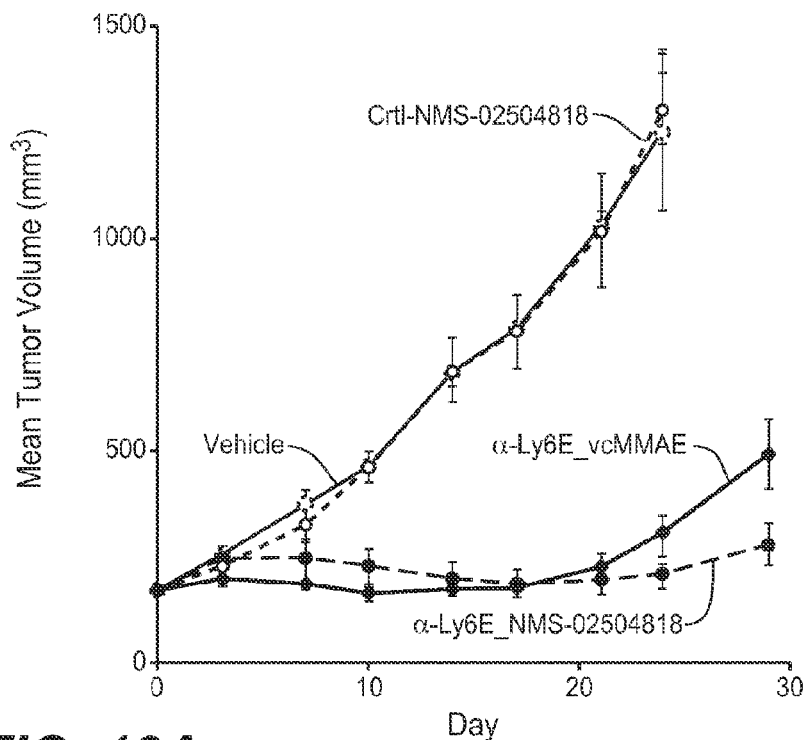
FIG. 13 compares the in vivo efficacy of various anti-Ly6E ADC conjugates in mouse xenograft model. Panels A, B and C all show subcutaneous tumors established in immunodeficient mice with pancreatic cancer cell line SU.86.86. When tumor volumes reached approximately 100-250 mm³ (day 0), animals were given a single IV injection of 1 mpk of either control ADC or anti-Ly6E ADC as indicated on the graphs. Average tumor volumes with standard deviations were determined from 10 animals per groups (indicated on graphs). Panel D shows 1+Ly6E staining on SU.86.86 cell pellet by immunohistochemistry.
Figure 13B:
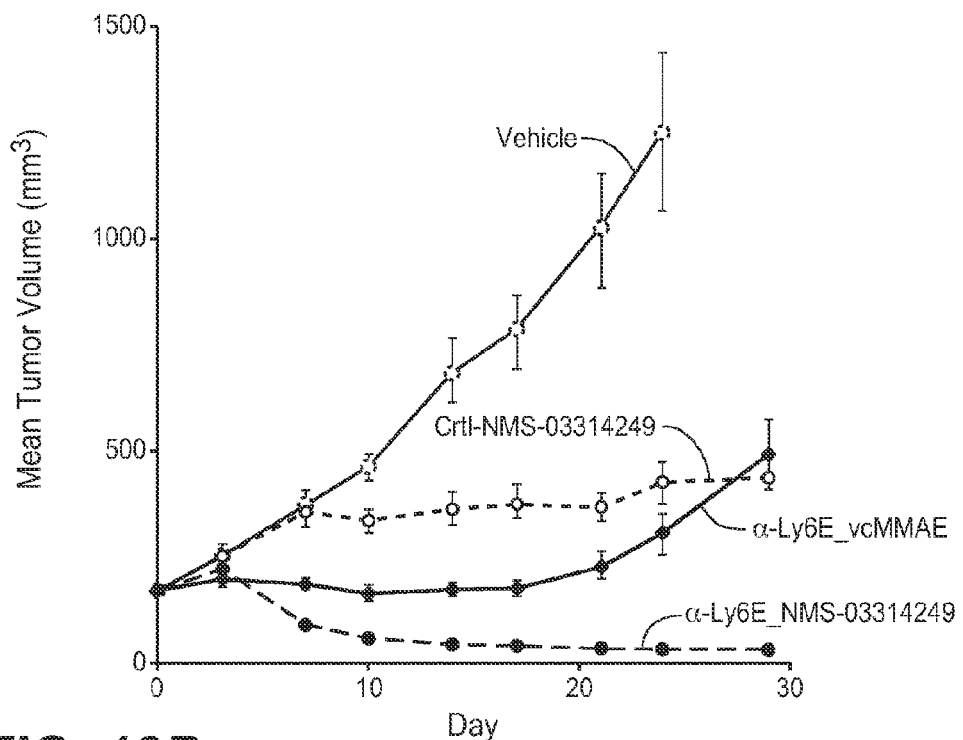
Figure 13C:
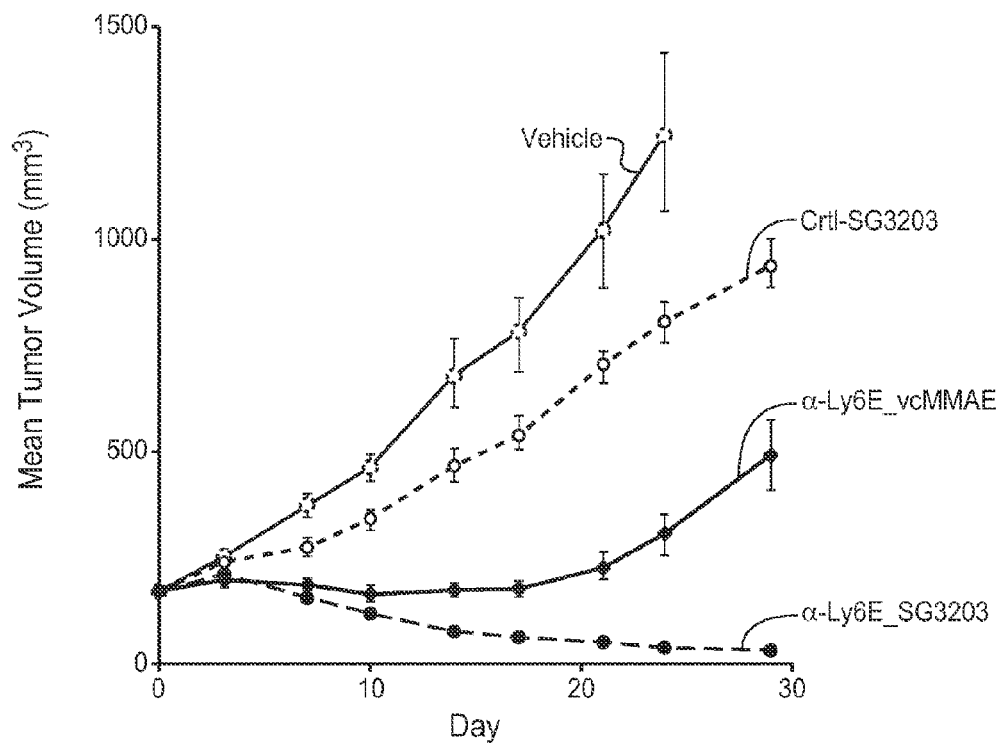
Figure 13D:
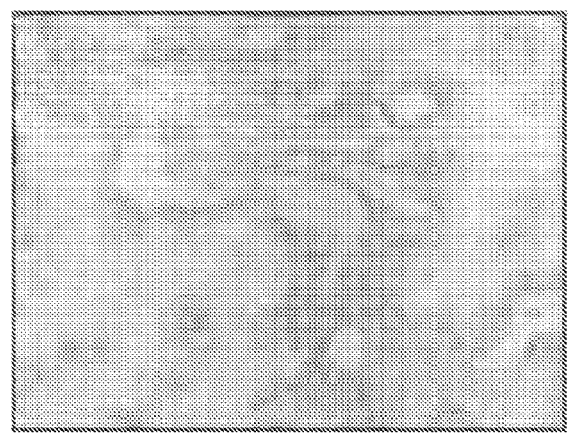

The results indicate that the Ly6E transcript expression in normal tissues is low compared to expression of Ly6E in breast and pancreatic cancers (FIG. 3).

Example 3—Antibody Generation and Humanization

For production of anti-Ly6E monoclonal antibodies, clones 4D8, 10G7 and 9B12, 5 female BALB/c mice were immunized with either bacterial (*Escherichia Coli*) generated His tagged Ly6E or mammalian (CHO-K1 S) generated C-Term myc 6× His tagged Ly6E protein as follows: Generation of Human Ly6E cDNA: Human Ly6E from Origene, Rockville, Md. and Cynomolgus monkey Ly6E cDNA from Open Biosystems, Lafayette, Colo. were cloned into a retroviral N-terminal gD-tagged vector. These constructs were used to generate pools of PC3 cells stably expressing human and Cynomolgus monkey Ly6E, respectively.

In addition, His tag Human Ly6E was cloned into a CMV promoter driven mammalian expression system and into a bacterial expression system to generate secreted protein from CHO-K1 suspension cells and from *Escherichia Coli*.

Immunization of Mice: Mice were immunized with 6 bi-weekly foot pad injections of 2 µg protein re-suspended in monophosphoryl lipid A/trehalose dicorynomycolate adjuvant (Ribi Immunochemicals). Three days after the final boost, popliteal lymph node cells were fused with cells derived from the murine myeloma cell line P3X63AgU.1 (CRL1597; American Type Culture Collection) using 50% polyethylene glycol. Hybridomas were selected using hypoxanthineaminopterin-thymidine (HAT) medium in 96-well plates. Ten to 14 days later, culture supernatants were collected and screened by direct ELISA against the immunogen and by flow cytometric analysis for binding to Ly6E on HT1080 transfected cell lines and then sub-cloned by limiting dilution.

Generation of hu9B16 CDR Grafts—

Several CDR grafts of murine 9B12 (mu9B12) were generated by Kunkel mutagenesis, using a separate oligonucleotide for each hypervariable region. The constructs were made in the context of transient IgG expression vectors. Correct clones were assessed by DNA sequencing. IgG was expressed and purified as described (See Liang, W.-C. et al. Function blocking antibodies to neuropilin-1 generated from a designed human synthetic antibody phage library. *Journal of Molecular Biology* 366, 815-829 (2007)).

Cell-Based Ly6E Competitive Binding Assay—

Cultured human Ly6E transfected PC3 cells were harvested with 5 mM EDTA containing PBS. Cells were washed with PBS and added onto a 384-well high binding plate (Meso Scale Discovery Technology (MSD); Gaithersburg, Md.). The plate was kept at room temperature for 1 hr to allow cells to adhere to the plate as described (See Lu, Y., Wong, W. L. & Meng, Y. G. A high throughput electrochemiluminescent cell-binding assay for therapeutic anti-CD20 antibody selection. *Journal of Immunological Methods* 314, 74-79 (2006)). The plate with cells was blocked with fetal bovine serum containing PBS for 1 hr and then cooled on ice. Serially diluted antibody variant samples were mixed with equal volume of fixed concentration of mouse 9B12 Ab. The mixtures were added onto the plates and incubated at 4° C. with gentle shaking for 1 hr.

The plate was then washed with cold PBS and an anti-mouse IgG Fc specific Ab (Jackson ImmunoReserach; West Grove, Pa.) labeled with sulfo-ruthenium tag was added to the plate as the detection reagent. The plate was incubated at 4° C. with gentle shaking for 1 hr. After incubation the plate was washed again, and MSD read buffer (MSD; Gaithersburg, Md.) was added onto the wells. The plate was read with a MSD SectorÒ imager 6000. The data was graphed and analyzed using KaleidaGraph software (Synergy Software; Reading, Pa.) to determine $IC_{50}$ values.

SPR Affinity Determination—

Affinity determinations were performed by surface plasmon resonance using single cycle kinetics on a BIAcore™-T100. Hu Ly6E was immobilized via EDC/NHS chemistry according to supplier's instructions (~20 response units (RU)) on a CM5 chip. For kinetic measurement, three-fold serial dilution of anti-Ly6E IgG (5 to 405 nM) in PBST were injected with 200 s for association & 300 s for dissociation at a flow rate of 30 ul/min at 25° C. Binding response was corrected by subtracting both the RU from a blank flow cell and from buffer run on the same flow cell. A 1:1 Languir model of simultaneous fitting of $k_{on}$ and $k_{off}$ was used to measure the apparent KD.

Humanization of 9B12 (Anti-Ly6E)

In order to humanize murine 9B12, the hypervariable regions (HVRs) were grafted into either a kappa I-$VH_2$ or kappa I-$VH_3$ consensus framework to generate several CDR grafts containing different combinations of potential vernier positions. Variable domain sequences of 9B12 variants aligned with human consensus (FIG. 4) kappa I and (FIG. 5) $VH_2$ or (FIG. 6) $VH_3$ variable domain frameworks. Amino acid positions that differ from the human consensus frameworks are highlighted in grey; regions that were transferred to generate the CDR graft are boxed. Positions are numbered according to Kabat (See Kabat, E. A., Wu, T. T., Perry, H. M., Gottesman, K. S. & Foeller, C. Sequences of proteins of immunological interest, Edn. 5th. (Public Health Service, National Institutes of Health, Bethesda, Md.; 1991). The HVR regions used in the VL domain were: positions 24-34 (L1), 50-56 (L2) and 89-97 (L3) (FIG. 4). In the VH domain, positions 26-35 (H1), 50-65 (H2) and 95-102 (H3) were grafted (FIGS. 5 and 6).

Several positions that potentially influence HVR conformation (vernier positions) in the new human framework were reverted to the mouse sequence in an effort to explore their role on Ly6E binding affinity. In the kappa I domain, combinations of positions 43, 44, and 71 were included. In the VH$_2$ domain, combinations of positions 24, 37, 49, 73 and 76 were explored while in the VH$_3$ domain, combinations of positions 24, 48, 67, 71, 76 and 78 were tested. All together 25 variants were constructed and expressed as IgG (Table 3). Purtified IgG were then screened in a cell-based Ly6E competitive binding assay. Most HVR constructs bound to Ly6E regardless of whether the consensus VH$_2$ or VH$_3$ variable heavy domain was used. The best clone with the fewest additional changes, hu9B12.v12, was obtained using the VH$_2$ domain and contained 3 vernier positions in kappa I (43, 44 and 71) and 2 in VH$_2$ (24 and 49). Table 3 shows a matrix of humanized HVR framework-repair variants that were constructed and assessed using the cell-based Ly6E competitive binding assay.

column and had a range of specific activity of 11.14-16.01 µCi/µg. Competition reaction mixtures of 50 µL containing a fixed concentration of iodinated antibody and decreasing concentrations of unlabeled antibody were placed into 96-well plates. The PC3 cells stably transduced with retrovirus to express either recombinant human or Cynomolgus monkey gD tagged Ly6E were detached from flasks using Sigma Cell Dissociation Solution and were washed with binding buffer (DMEM with 2% FBS, 50 mM HEPES, pH 7.2, and 0.1% sodium azide). The washed cells were added at an approximate density of 200,000 cells in 0.2 mL of binding buffer to the 96-well plates containing the 50-µL competition reaction mixtures. The final concentration of the iodinated antibody in each competition reaction with cells was 200 pM and the final concentration of the unlabeled antibody in the competition reaction with cells varied, starting at 500 nM and then decreasing by 1:2-fold dilution for ten concentrations, and included a zero-added, buffer-only sample. Competition reactions with cells for each concentration of unlabeled antibody were assayed in triplicate. Competition reactions with cells were incubated for 2 hours at room temperature. After the 2-hour incubation, the competition reactions were transferred to a Millipore Mul-

TABLE 3

| | | | | | | | | | | | Light Chain | | | |
| --- | --- | --- | --- | --- | --- | --- | --- | --- | --- | --- | --- | --- | --- | --- |
| | | | | | | | | | | | k1 graft | k1 graft 43 + 44 | k1 graft 43 + 44 + 71 | k1 graft + 71 |
| Heavy Chain | VH2 graft | | | | | | | | | | | | | |
| | VH2 graft | | | | | + | 49 | | | | v1 (no binding) | v6 (no binding) | v11 (no binding) | |
| | VH2 graft | + | 24 | | | + | 49 | | | | v2 (28, 37 nM) | v7 (24, 36 nM) | v12 (15, 16 nM) | |
| | VH2 graft | + | 24 | + | 37 | + | 49 | | | | | | v16 (27 nM) | v21 (82 nM) |
| | VH2 graft | + | 24 | | | + | 49 | + | 73 | | | | v17 (29 nM) | v22 (59 nM) |
| | VH2 graft | + | 24 | | | + | 49 | + | 73 | + 76 | | | v18 (22 nM) | v23 (54 nM) |
| | VH2 graft | + | 24 | + | 37 | + | 49 | + | 73 | + 76 | | | v19 (28 nM) | v24 (53 nM) |
| | VH3 graft | | | | | | | | | | v3 (no binding) | v8 (no binding) | v13 (no binding) | |
| | VH3 graft | + | 24 | | | | | | | | v4 (98, 70 nM) | v9 (30, 44 nM) | v14 (39, 56 nM) | |
| | VH3 graft | + | | | | | | | 71 | + 78 | v5 (70 nM) | v10 (61 nM) | v15 (42, 52 nM) | |
| | VH3 graft | + | 24 | + | 48 | + | 67 | − | 71 | + 76 + 78 | | | v20 (26 nM) | v25 (56 nM) | chimeric 9B12 (3, 6, 5 nM)

This clone had about 3-5-fold reduce affinity for human Ly6E in the cell-based Ly6E competitive binding assay but similar affinity by SPR and scatchard analysis (Table 4), where ch9B12 denotes the chimeric variant and 9B12.v12 denotes the humanized variant.

TABLE 4

| | Scatchard Analysis | | Biacore | cell-based Ly6E competitive binding assay | |
| --- | --- | --- | --- | --- | --- |
| | hu Ly6E KD (nM) | cyno Ly6E KD (nM) | hu Ly6E KD (nM) | hu Ly6E KD (nM) | cyno Ly6E KD (nM) |
| Ch 9B12 | 4 | 4 | 6 | 3-6 | 5-7 |
| 9B12.v12 | 4 | 14 | 7 | 15-19 | 16-40 |

Example 4—Binding of Anti-Ly6E Antibody to Human and Cynomologous Ly6E

A scatchard analysis was performed to determine affinity and binding sites per cell for the antibodies. Hu.9B12v12 antibody was iodinated several times using the Iodogen method. The radiolabeled Hu.9B12v12 antibody was purified from free $^{125}$I—Na by gel filtration using a NAP-5 tiscreen filter plate and washed four times with binding buffer to separate the free from bound iodinated antibody. The filters were counted on a Wallac Wizard 1470 gamma counter (PerkinElmer Life and Analytical Sciences; Wellesley, Mass.). The binding data were evaluated using New Ligand software (Genentech), which uses the fitting algorithm of Munson and Rodbard (1980) to determine the binding affinity of the antibody. As shown in FIG. 6, Panel A and B and in Table 5, the binding affinity of Hu9B12v12 on human and cynomolgus monkey was estimated at 4.0 nM and 7.9 nM respectively.

TABLE 5

| Antibody | Species | Affinity | Sites/Cell |
| --- | --- | --- | --- |
| Ch.9B12 | Human | 2 nM | 7000 |
| | Cyno | 2.9 nM | 16,000 |
| Hu.9B12.v12 | Human | 4 nM | 7000 |
| | Cyno | 7.9 nM | 16,000 |
| gD | Human | 1.1 nM | 13,000 |
| | Cyno | 2 nM | 53,000 |

Example 5—Generation of Antibody Drug Conjugates

For larger scale antibody production, antibodies were produced in CHO cells. Vectors coding for VL and VH were transfected into CHO cells and IgG was purified from cell culture media by protein A affinity chromatography.

Generation of vcMMAE ADC: Anti-Ly6E antibody-drug conjugates (ADCs) were produced by conjugating hu9B12.v12 or control anti gD ADCs were conjugated to the drug-linker moiety MC-vc-PAB-MMAE, which is depicted herein. For convenience, the drug-linker moiety MC-vc-PAB-MMAE is sometimes referred to in these Examples and in the Figures as "vcMMAE" or "VCE." Prior to conjugation, the antibodies were partially reduced with TCEP using standard methods in accordance with the methodology described in WO 2004/010957 A2. The partially reduced antibodies were conjugated to the drug-linker moiety using standard methods in accordance with the methodology described, e.g., in Doronina et al. (2003) Nat. Biotechnol. 21:778-784 and US 2005/0238649 A1. Briefly, the partially reduced antibodies were combined with the drug-linker moiety to allow conjugation of the drug-linker moiety to reduced cysteine residues of the antibody. The conjugation reactions were quenched, and the ADCs were purified. The drug load (average number of drug moieties per antibody) for each ADC was determined and was between 3.3 and 4.0 for the anti-Ly6E antibodies and anti-gD control antibodies.

Example 6—Binding of Humanized Anti-Ly6E ADC to Human and Cyno Ly6E

In vitro killing assay: To assess the effects of Hu9B12v12-ADC on cell viability, cells were plated at 1,500 per well in 50 µL of normal growth medium in 96-well clear-bottom black plates. Twenty-four hours later, an additional 50 µL of culture medium with serial dilutions of Hu9B12v12-ADC concentrations was added to triplicate wells. Five days later, cell survival was determined using CellTiter-Glo Luminescent Cell Viability Reagent (G7572; Promega Corporation) and with an EnVision 2101 Mutilabel Reader (Perkin-Elmer). For the two cell lines tested, in vitro killing efficacy appeared proportional to the expression of Ly6E on the cell surface (FIG. 6, Panels A and B).

Flow Cytometry: For fluorescence-activated cell sorting (FACS), cells were harvested in PBS with 2.5 mmol/L EDTA and washed in PBS buffer containing 1% FBS. All subsequent steps were carried out at 4° C. Cells were incubated for 1 hour each with 3 to 5 µg/mL primary antibodies, followed by the appropriate secondary antibodies. Cells were then analyzed with a FACS Calibur flow cytometer (BD Biosciences) and GeoMean values were obtained. Primary antibodies, Hu.9B12v12 for Ly6E cell surface detection, in-house generated anti-gD mAb for N-Term gD tag detection were used. Alexa 488-conjugated anti-mouse or anti-human IgG fluorescent detection reagent (A11017, A11013; Invitrogen) were used.

Example 7—In Vivo Efficacy of Anti-Ly6E ADC in Xenograft Mouse Model

Breast cancer cell line, HCC1569 (CRL-2330), pancreatic cancer cell line SU.86.86 (CRL-1837), Chinese Hamster ovary cell line, CHO-K1 (CC1-61) and prostatic cancer cell line PC3 (CRL-1435) were obtained from American Type Culture Collection (ATCC, Manassas, Va.). CHO-K1S is a suspension cell line derivative of CHO-K1. The HCC1569 X2 cell line is a derivative of the parental HCC1569 cell line (ATCC, CRL-2330) optimized for growth in vivo. Parental HCC1569 cells were injected subcutaneously in the right flank of female Taconic NCr nude mice, one tumor was harvested, minced and grown in vitro resulting in the HCC1569 X1 cell line. The HCC1569 X1 line was injected again subcutaneously in the right flank of female Taconic NCr nude mice in an effort to improve the growth of the cell line. A tumor from this study was collected and again adapted for in vitro growth to generate the HCC1569 X2 cell line. This cell line and tumors derived from this line express Ly6E.

Xenograft models: Efficacy of anti-Ly6E antibody drug conjugates (ADCs) was evaluated in xenograft models derived from cell lines described above or in primary patient derived tumor models, the latter experiments were conducted at Oncotest, Freiburg, Germany and in XenTech, Genopole, France.

All studies conducted at Genentech, South San Francisco, Calif. were in accordance with the Guide for the Care and Use of Laboratory Animals (Ref: Institute of Laboratory Animal Resources (NIH publication no. 85-23), Washington, D.C.: National Academies Press; 1996). All experiments conducted at Oncotest were approved by the local authorities, and are conducted according to the guidelines of the German Animal Welfare Act (Tierschutzgesetz). The authorization to use animals in the CERFE facilities of XenTech was obtained by The Direction des Services Vétérinaires, Ministère de l'Agriculture et de la Peche, France (agreement No. A 91-228-107). The animal care and housing are in accordance with European Convention STE 123. All experiments at XenTech will be performed in accordance with French legislation concerning the protection of laboratory animals and in accordance with a currently valid license for experiments on vertebrate animals, issued by the French Ministry for Agriculture and Fisheries to Dr. Truong-An TRAN (No. A 91-541 dated 21 Dec. 2010; validity: 5 years). 6- to 9-week old female immunodeficient mice were inoculated subcutaneously in the dorsal right flank and average tumor volumes with SDs were determined from 9-10 mice per group.

For efficacy studies with xenografts derived from cell lines, NCR nude mice from Taconic were inoculated with 5 million cells in HBSS with Matrigel or C.B-17 SCID (inbred) mice From Charles River were inoculated with 2 million cells in HBSS with Matrigel. 0.36 mg estrogen implants were used for the HCC1569 X2 xenograft model. For efficacy studies with tumor explants at XenTech and Oncotest, athymic nude or NMRI nu/nu mice from Harlan or Charles River were implanted with primary breast or pancreatic cancer patient derived materials from models HBCx-8, HBCx-9, MAXF-1162 and PAXF-1657. When tumor volumes reached approximately 80-200 mm3 (day 0), animals were randomized into groups of 9-10 each and administered a single intravenous (IV) injection of either vehicle control or the ADC at the appropriate dose. Tumor volumes were measured twice per week until study end.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An isolated monoclonal antibody that binds to Ly6E, wherein the antibody comprises (a) HVR-H1 comprising the amino acid sequence of SEQ ID NO:10; (b) HVR-H2 comprising the amino acid sequence of SEQ ID NO:11; (c) HVR-H3 comprising the amino acid sequence of SEQ ID NO:12; (d) HVR-L1 comprising the amino acid sequence of SEQ ID NO:7; (e) HVR-L2 comprising the amino acid sequence of SEQ ID NO:8; and (f) HVR-L3 comprising the amino acid sequence of SEQ ID NO:9.

2. The antibody of claim 1, which is a humanized or chimeric antibody.

3. The antibody of claim 1, wherein the antibody is internalized in a Ly6E-expressing cell upon binding to Ly6E.

4. The antibody of claim 1, which is an antibody fragment that binds to an epitope within amino acids 21-131 of SEQ ID NO:1.

5. The antibody of claim 1, further comprising a light chain variable domain framework FR2 sequence of SEQ ID NO:20 or light chain variable domain framework FR3 of SEQ ID NO:21 or heavy chain variable domain framework FR1 or SEQ ID NO:23, or heavy chain variable domain framework FR2 of SEQ ID NO:24.

6. The antibody of claim 1, comprising (a) a VH sequence having at least 95% sequence identity to the amino acid sequence of SEQ ID NO:5; (b) a VL sequence having at least 95% sequence identity to the amino acid sequence of SEQ ID NO:3; or (c) a VH sequence as in (a) and a VL sequence as in (b).

7. The antibody of claim 1, comprising a VH sequence of SEQ ID NO:5.

8. The antibody of claim 1, comprising a VL sequence of SEQ ID NO:3.

9. The antibody of claim 1, wherein the antibody is a cysteine engineered antibody.

10. The antibody of claim 9, wherein the cysteine engineered antibody comprises a cysteine substitution in a light chain constant domain.

11. The antibody of claim 9, wherein the cysteine engineered antibody comprises a cysteine substitution in a heavy chain constant domain.

12. An isolated monoclonal antibody that binds to Ly6E comprising a VH sequence of SEQ ID NO:5 and a VL sequence of SEQ ID NO:3.

13. The antibody of claim 12, which is an IgG1, IgG2a, or IgG2b antibody.

14. An immunoconjugate comprising the antibody of claim 1 and a cytotoxic agent.

15. The immunoconjugate of claim 14 having the formula Ab-(L-D)p, wherein:

(a) Ab is the antibody;

(b) L is a linker;

(c) D is a cytotoxic agent selected from a maytansinoid, an auristatin, a calicheamicin, a pyrrolobenzodiazepine, and a nemorubicin derivative; and (d) p ranges from 1-8.

16. The immunoconjugate of claim 14, wherein the cytotoxic agent is an auristatin.

17. The immunoconjugate of claim 15, wherein D has formula $D_E$

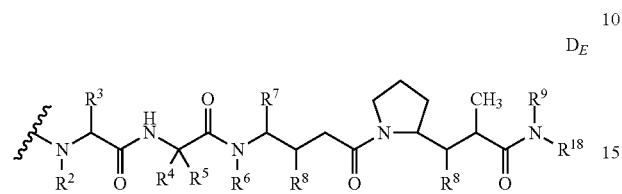

$D_E$ and wherein $R^2$ and $R^6$ are each methyl, $R^3$ and $R^4$ are each isopropyl, $R^5$ is H, $R^7$ is sec-butyl, each $R^8$ is independently selected from $CH_3$, $O-CH_3$, OH, and H; $R^9$ is H; and $R^{18}$ is $-C(R^8)_2-C(R^8)_2$-aryl.

18. The immunoconjugate of claim 14, wherein the cytotoxic agent is MMAE.

19. The immunoconjugate of claim 14, wherein the cytotoxic agent is a pyrrolobenzodiazepine.

20. The immunoconjugate of claim 15, wherein D is a pyrrolobenzodiazepine of
Formula A:

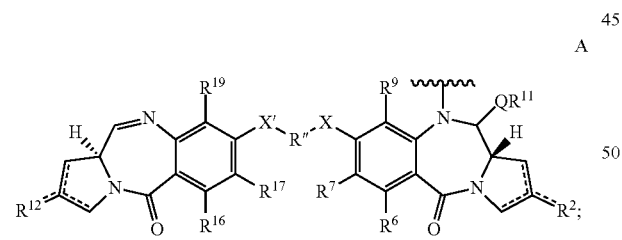

A wherein the dotted lines indicate the optional presence of a double bond between C1 and C2 or C2 and C3;

$R^2$ is independently selected from H, OH, =O, =$CH_2$, CN, R, OR, =CH—$R^D$, =C($R^D$)$_2$, O—$SO_2$—R, $CO_2$R and COR, and optionally further selected from halo or dihalo, wherein $R^D$ is independently selected from R, $CO_2$R, COR, CHO, $CO_2$H, and halo;

$R^6$ and $R^9$ are independently selected from H, R, OH, OR, SH, SR, $NH_2$, NHR, NRR', $NO_2$, $Me_3$Sn and halo;

$R^7$ is independently selected from H, R, OH, OR, SH, SR, $NH_2$, NHR, NRR', $NO_2$, $Me_3$Sn and halo;

Q is independently selected from O, S and NH;

$R^{11}$ is either H, or R or, where Q is O, $SO_3$M, where M is a metal cation;

R and R' are each independently selected from optionally substituted $C_{1-8}$ alkyl, $C_{3-8}$ heterocyclyl and $C_{5-20}$ aryl groups, and optionally in relation to the group NRR', R and R' together with the nitrogen atom to which they are attached form an optionally substituted 4-, 5-, 6- or 7-membered heterocyclic ring;

$R^{12}$, $R^{16}$, $R^{19}$ and $R^{17}$ are as defined for $R^2$, $R^6$, $R^9$ and $R^7$ respectively;

R" is a $C_{3-12}$ alkylene group, which chain may be interrupted by one or more heteroatoms and/or aromatic rings that are optionally substituted; and X and X' are independently selected from O, S and N(H).

21. The immunoconjugate of claim 15, wherein D has the structure:

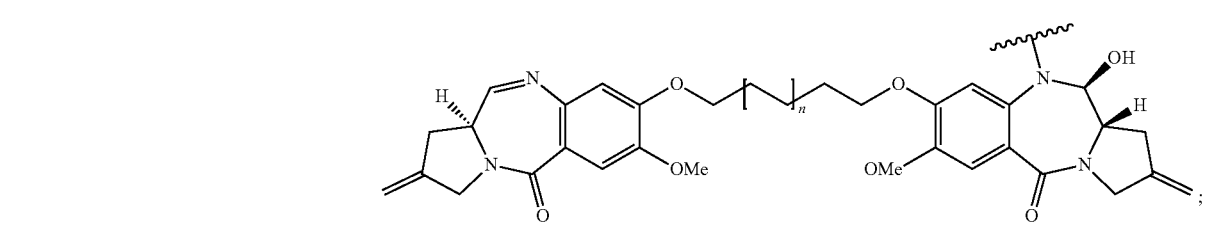

wherein n is 0 or 1.

22. The immunoconjugate of claim 14, wherein the cytotoxic agent is a nemorubicin derivative.

23. The immunoconjugate of claim 15, wherein D has a structure selected from:

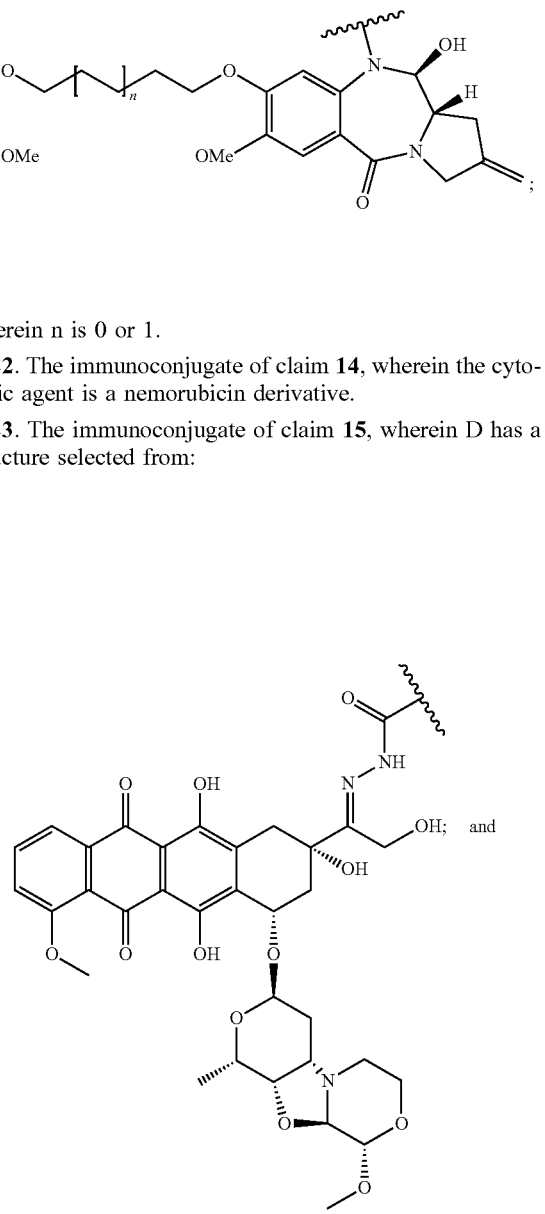

-continued

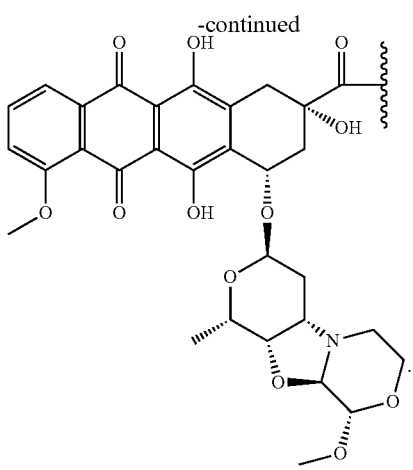

24. The immunoconjugate of claim 15, wherein the linker is cleavable by a protease.

25. The immunoconjugate of claim 15, wherein the linker comprises a valine-citrulline, alanine-phenylalanine, phenylalanine-lysine, phenylalanine-homolysine, or N-methyl-valine-citrulline dipeptide.

26. The immunoconjugate of claim 15, wherein the linker is acid-labile.

27. The immunoconjugate of claim 26, wherein the linker comprises hydrazone.

28. The immunoconjugate of claim 15 having the formula:

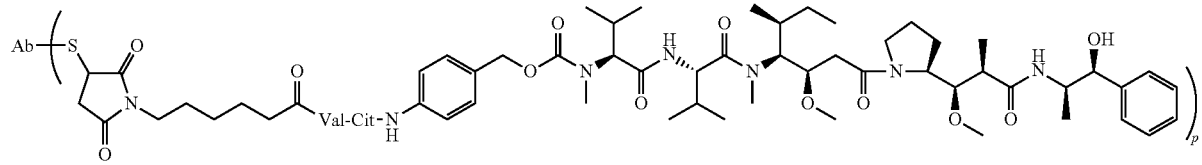

wherein S is a sulfur atom.

29. The immunoconjugate of claim 15 having the formula:

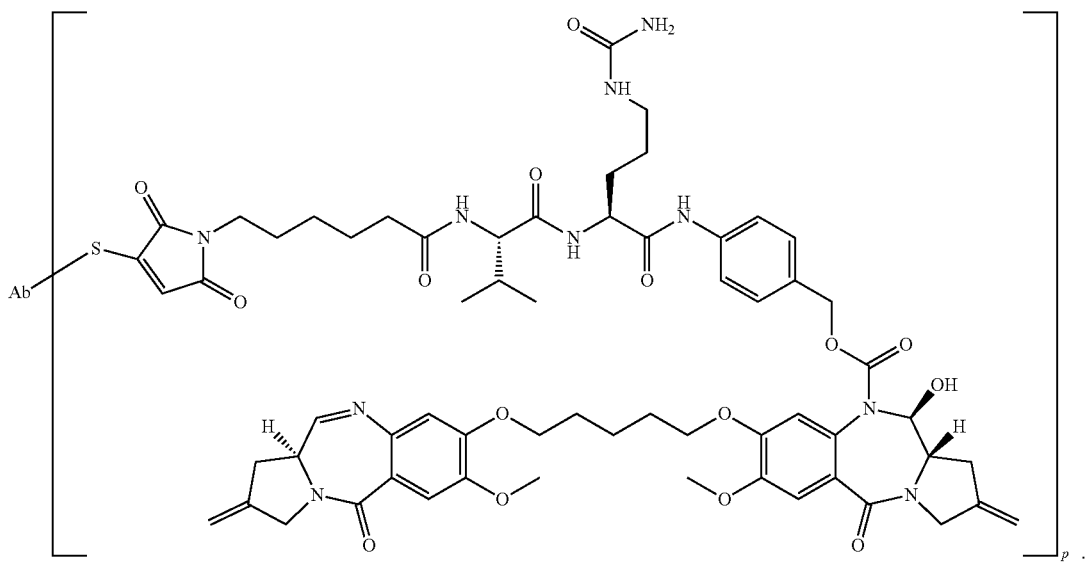

30. The immunoconjugate of claim 15 having a formula selected from:
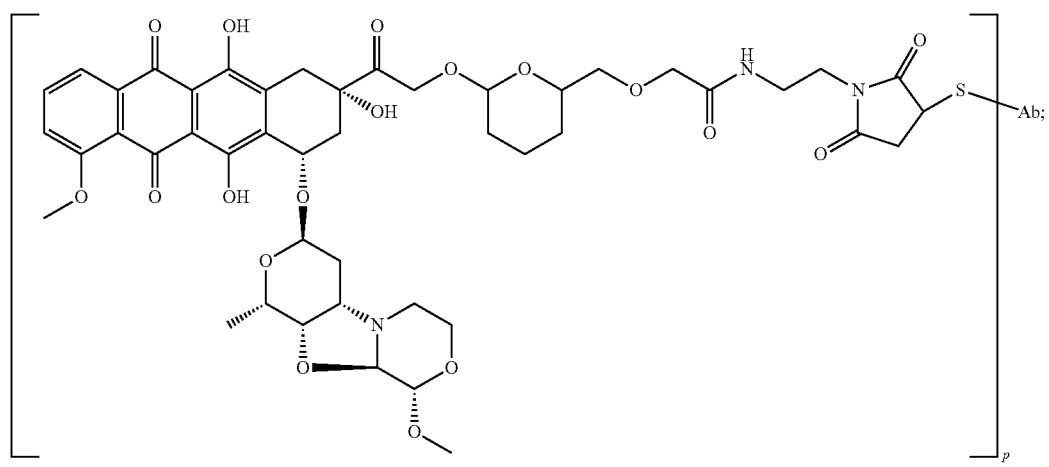
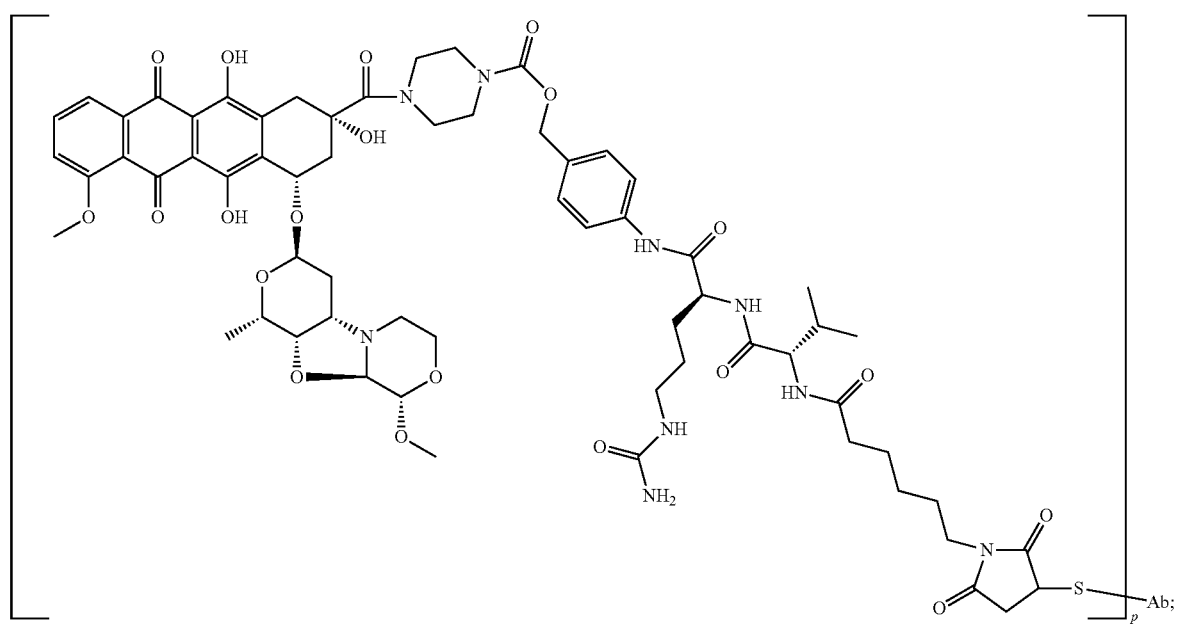
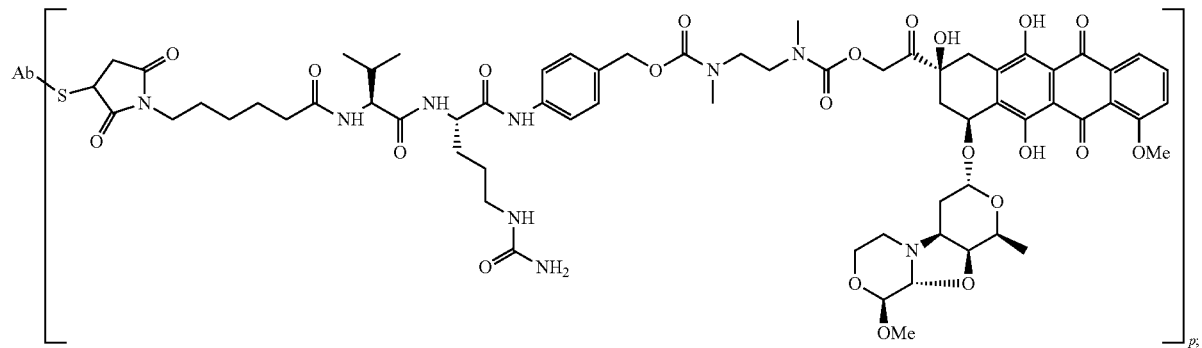

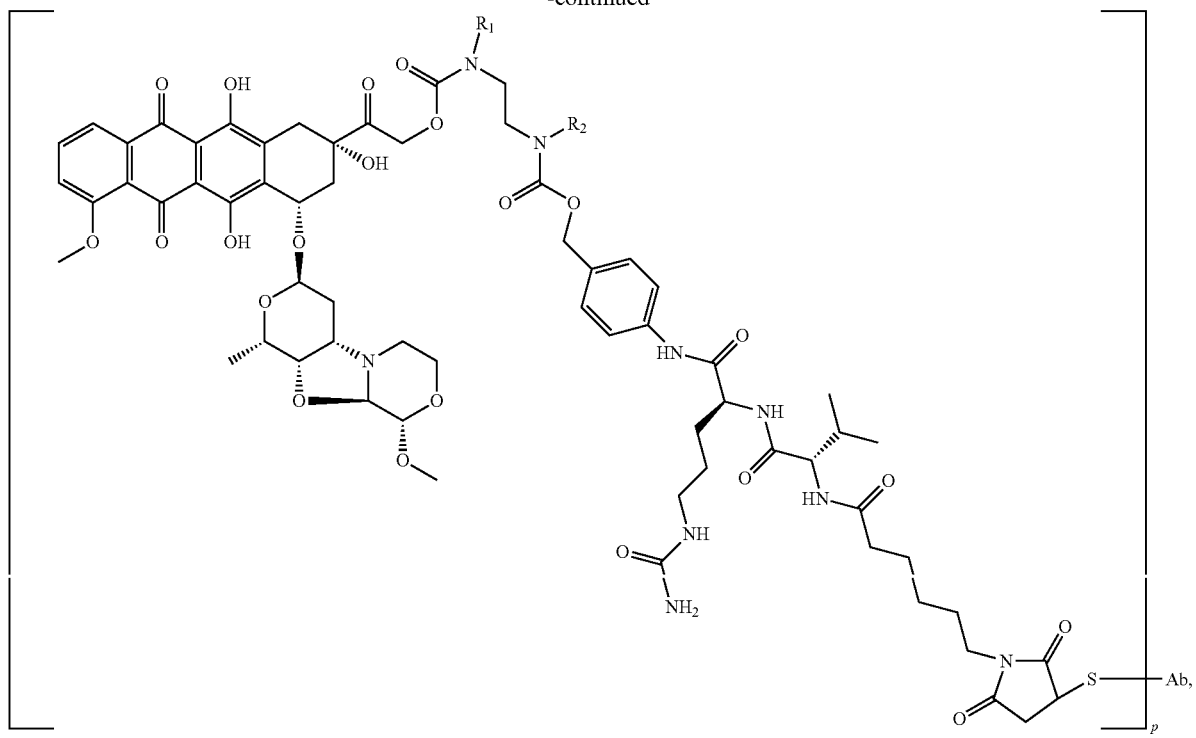

wherein $R_1$ and $R_2$ are independently selected from H and $C_1$-$C_6$ alkyl; and

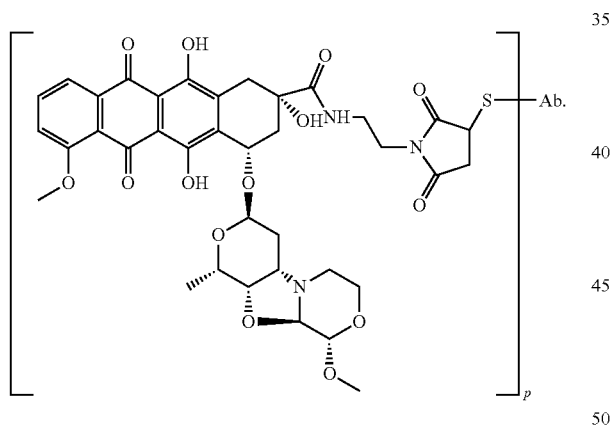

31. The immunoconjugate of claim 15, wherein p ranges from 2-5.

32. The immunoconjugate of claim 28, wherein the antibody comprises a VH sequence of SEQ ID NO:5 and a VL sequence of SEQ ID NO:3.

33. A pharmaceutical formulation comprising the immunoconjugate of claim 15 and a pharmaceutically acceptable carrier.

34. The pharmaceutical formulation of claim 33, further comprising an additional therapeutic agent.

35. The pharmaceutical formulation of claim 34, wherein the additional therapeutic agent is a platinum complex.

36. An immunoconjugate having the formula:

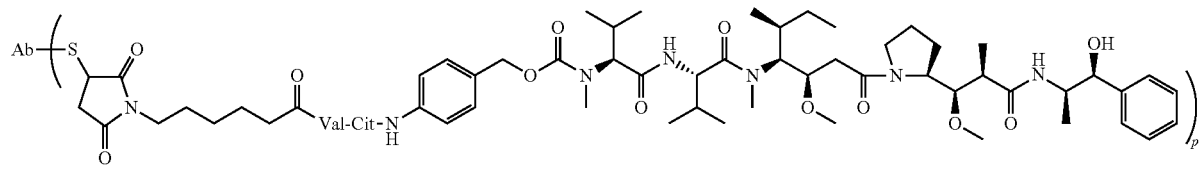

wherein
a) Ab is a monoclonal antibody that binds to Ly6E, wherein said antibody comprises (i) HVR-H1 comprising the amino acid sequence of SEQ ID NO:10; (ii) HVR-H2 comprising the amino acid sequence of SEQ ID NO:11; (iii) HVR-H3 comprising the amino acid sequence of SEQ ID NO:12; (iv) HVR-L1 comprising the amino acid sequence of SEQ ID NO:7; (v) HVR-L2 comprising the amino acid sequence of SEQ ID NO:8; (vi) HVR-L3 comprising the amino acid sequence of SEQ ID NO:9;
b) S is a sulfur atom; and
c) p ranges from 2-5.

37. The antibody of claim 36, wherein the antibody comprises a VH sequence of SEQ ID NO:5 and a VL sequence of SEQ ID NO:3.

38. A labeled antibody comprising the antibody of claim 1 conjugated to a label.

39. The labeled antibody of claim 38, wherein the label is a positron emitter.

40. The labeled antibody of claim 39, wherein the positron emitter is $^{89}$Zr.

* * * * *